(12) United States Patent
Halpern et al.

(10) Patent No.: US 12,201,431 B2
(45) Date of Patent: **\*Jan. 21, 2025**

(54) BLOOD GLUCOSE STATES BASED ON SENSED BRAIN ACTIVITY

(71) Applicant: SynchNeuro, Inc., Philadelphia, PA (US)

(72) Inventors: Casey Halpern, Philadelphia, PA (US); Emily Mirro, Pacifica, CA (US); Cammie Rolle, Novato, CA (US); Emmanuel Dumont, New York, NY (US)

(73) Assignee: SynchNeuro, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/593,846

(22) Filed: Mar. 1, 2024

(65) Prior Publication Data

US 2024/0293083 A1    Sep. 5, 2024

Related U.S. Application Data

(60) Provisional application No. 63/503,345, filed on May 19, 2023, provisional application No. 63/487,880, (Continued)

(51) Int. Cl.
*A61B 5/291* (2021.01)
*A61B 5/00* (2006.01)
(Continued)

(52) U.S. Cl.
CPC ............ *A61B 5/291* (2021.01); *A61B 5/0006* (2013.01); *A61B 5/14532* (2013.01);
(Continued)

(58) Field of Classification Search
CPC ..... A61B 5/6815; A61B 5/0006; A61B 5/256; A61B 5/591; A61B 5/374; A61B 5/7264;
(Continued)

(56) References Cited

U.S. PATENT DOCUMENTS 6,572,542 B1   6/2003   Houben et al.
8,118,741 B2   2/2012   Beck-Nielsen
(Continued)

FOREIGN PATENT DOCUMENTS

WO   WO2018/064225 A1   4/2018
WO   WO2022/212891 A1   10/2022
(Continued)

OTHER PUBLICATIONS

Cranwell; Utilizing brain activity to non-invasively predict blood glucose levels; Master Thesis; East Carolina University; 260 pages; retrieved from the internet (https://thescholarship.ecu.edu/bitstream/handle/10342/6046/CRANWELL-MASTERSTHESIS-2016.pdf?sequence=1&isAllowed=y) on Apr. 17, 2024.
(Continued)

*Primary Examiner* — Chu Chuan Liu
(74) *Attorney, Agent, or Firm* — Shay Glenn LLP; Thomas M. Zlogar

(57) ABSTRACT

Blood glucose states based at least on sensed brain activity data. Blood glucose states may be predicted states using prediction models, and may be real-time or future glucose states. One or more wearable sensors, optionally adapted for use in either single channel or dual channel sensing, can record brain activity signals and communicate brain activity signal data to a remote device.

26 Claims, 46 Drawing Sheets

Related U.S. Application Data filed on Mar. 1, 2023, provisional application No. 63/487,845, filed on Mar. 1, 2023, provisional application No. 63/487,870, filed on Mar. 1, 2023.

(51) Int. Cl.
| | | |
|---|---|---|
| *A61B 5/145* | (2006.01) | |
| *A61B 5/256* | (2021.01) | |
| *A61B 5/257* | (2021.01) | |
| *A61B 5/369* | (2021.01) | |
| *A61B 5/374* | (2021.01) | |

(52) U.S. Cl.
CPC ............. *A61B 5/256* (2021.01); *A61B 5/257* (2021.01); *A61B 5/369* (2021.01); *A61B 5/374* (2021.01); *A61B 5/6814* (2013.01); *A61B 5/6815* (2013.01); *A61B 5/7264* (2013.01); *A61B 5/7275* (2013.01); *A61B 5/742* (2013.01); *A61B 5/7455* (2013.01); *A61B 2562/164* (2013.01)

(58) Field of Classification Search
CPC .... A61B 5/7275; A61B 5/145; A61B 5/14532
See application file for complete search history.

(56) References Cited

U.S. PATENT DOCUMENTS

| | | | |
|---|---|---|---|
| 8,201,330 | B1 | 6/2012 | Rood et al. |
| 8,577,440 | B2 | 11/2013 | Afanasewicz et al. |
| 8,870,766 | B2 | 10/2014 | Stivoric et al. |
| 9,585,607 | B2 | 3/2017 | Kamath et al. |
| 10,327,656 | B2 | 6/2019 | Madsen et al. |
| 10,827,956 | B2 | 11/2020 | Brister et al. |
| 11,020,035 | B2 | 6/2021 | Dudek et al. |
| 11,064,917 | B2 | 7/2021 | Simpson et al. |
| 11,229,406 | B2 | 1/2022 | Zhong et al. |
| 11,445,974 | B2 | 9/2022 | Jensen et al. |
| 11,672,422 | B2 | 6/2023 | Brister et al. |
| 11,744,943 | B2 | 9/2023 | Dobbles et al. |
| 2008/0243022 | A1 | 10/2008 | Donnett et al. |
| 2008/0306353 | A1 | 12/2008 | Douglas et al. |
| 2012/0029336 | A1* | 2/2012 | Terada ................. A61B 5/6843 600/383 |
| 2012/0302858 | A1 | 11/2012 | Kidmose et al. |
| 2013/0018249 | A1 | 1/2013 | Storm |
| 2014/0012511 | A1 | 1/2014 | Mensinger et al. |
| 2014/0371802 | A1 | 12/2014 | Mashiachl et al. |
| 2015/0313498 | A1 | 11/2015 | Coleman et al. |
| 2016/0081623 | A1 | 3/2016 | Lunner |
| 2016/0256086 | A1 | 9/2016 | Byrd et al. |
| 2017/0164878 | A1 | 6/2017 | Connor |
| 2017/0215759 | A1 | 8/2017 | Dudek et al. |
| 2019/0223747 | A1 | 7/2019 | Chou |
| 2019/0246982 | A1 | 8/2019 | Mackellar et al. |
| 2020/0138300 | A1 | 5/2020 | Fleischer et al. |
| 2020/0297256 | A1 | 9/2020 | Seo |
| 2021/0038897 | A1 | 2/2021 | Molnar et al. |
| 2021/0228134 | A1 | 7/2021 | Trapero Martin et al. |
| 2022/0061728 | A1 | 3/2022 | Goldstein |
| 2022/0117503 | A1 | 4/2022 | Wang et al. |
| 2022/0265178 | A1 | 8/2022 | Tran |
| 2022/0313172 | A1 | 10/2022 | Nie et al. |
| 2022/0338792 | A1 | 10/2022 | Elwood et al. |
| 2023/0225659 | A1 | 7/2023 | Azemi et al. |

FOREIGN PATENT DOCUMENTS

| | | |
|---|---|---|
| WO | WO2023/034820 A1 | 3/2023 |
| WO | WO2023/183798 A2 | 9/2023 |
| WO | WO2024/077303 A2 | 4/2024 |
| WO | WO2024/182777 A2 | 9/2024 |

OTHER PUBLICATIONS

Huang et al.; Spectro-spatial features in distributed human intracranial activity proactively encode peripheral metabolic activity; Nature Communications; 14(1); doi.org/10.1038/s41467-023-38253-7; 11 pages; May 2023.
Trihealth, Medications that affect blood sugar; 4 pages; retrieved from the internet (https://www.trihealth.com/services/diabetes/living-with-diabetes/medications/medications-that-affect-blood-sugar) on Apr. 18, 2024.
Apollo et al.; U.S. Appl. No. 18/593,843 entitled "Blood glucose states based on sensed brain activity," filed Mar. 1, 2024.
Halpern et al.; U.S. Appl. No. 18/593,845 entitled "Blood glucose states based on sensed brain activity," filed Mar. 1, 2024.
Halpern et al.; U.S. Appl. No. 18/593,847 entitled "Blood glucose states based on sensed brain activity," filed Mar. 1, 2024.

* cited by examiner

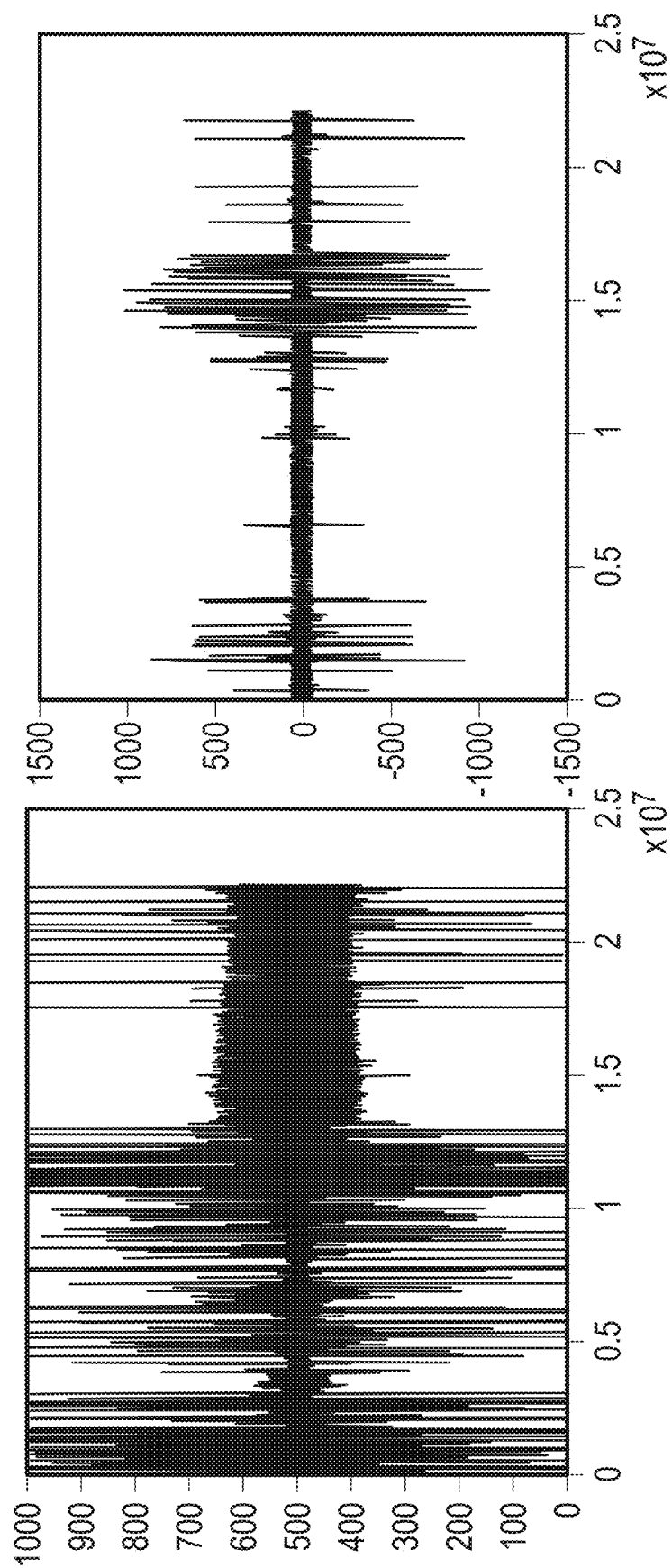

Summary

| Brain region | Band | High/Negative correlation |
|---|---|---|
| O1 | 1-12 Hz | Positive |
| O2 | Theta (5-8 Hz) | Positive |
| F7 | 5-12 Hz | Positive |
| F8 | 5-12 Hz | Positive |
| M1 | 9-12 Hz | Negative |
| M2 | 9-12 Hz | Negative |

FIG. 23A

Channels Which Have Significant Correlation in Each Time Window

| Minute | T1 = -13 | -12 | -11 | -10 | -9 | -8 | -7 | -6 |
|---|---|---|---|---|---|---|---|---|
| T2 = -12 | O1/O2 | | | | | | | |
| -11 | O1/O2 | O1 | | | | | | |
| -10 | O1/O2/M2 | O1/O2 | O1/O2/M1 | | | | | |
| -9 | O1/O2/M2 | O1/O2/M2 | O1/O2 | O1 | | | | |
| -8 | O1/O2 | O1/O2 | O1/O2 | O1/O2 | O2 | | | |
| -7 | O1/O2/M1/M2 | O1/O2/M1/M2 | O1/O2/M1/M2 | O1/O2 | O1/O2 | O1/O2 | | |
| -6 | O1/O2/M1/M2/F7/F8 | O1/O2/M1/M2/F7/F8 | O1/O2/M1/M2/F7/F8 | O1/O2/M1/M2/F7/F8 | O1/O2/M1/M2/FT10/F8 | O1/O2/M2 | O1/O2/M2 O1 | |
| -5 | O1/O2/M1/M2/F7/F8 | O1/O2/M1/M2/F7/F8 | O1/O2/M1/M2/F7/F8 | O1/O2/M1/F8 | O1/O2/M1 | O1/O2/M1 | O1/O2/M2 O1/O2 | O1/O2 |

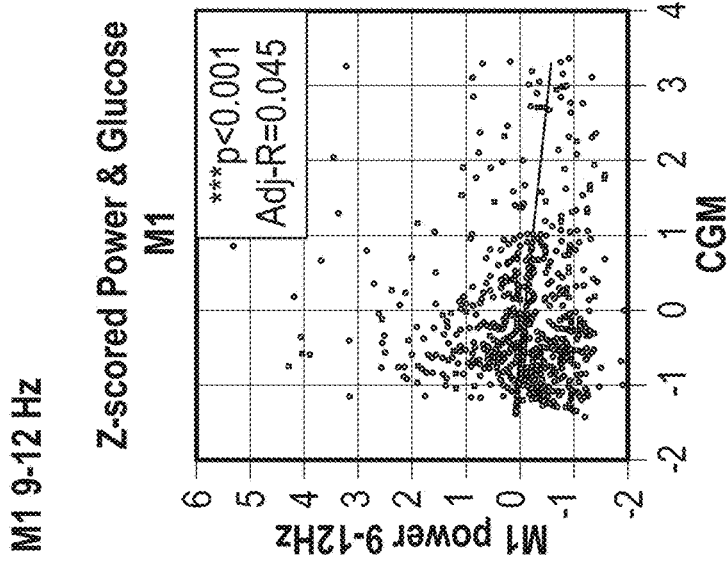
FIG. 25B
FIG. 25A
Example When EEG Time Window is T1=-11min/T2=-6min

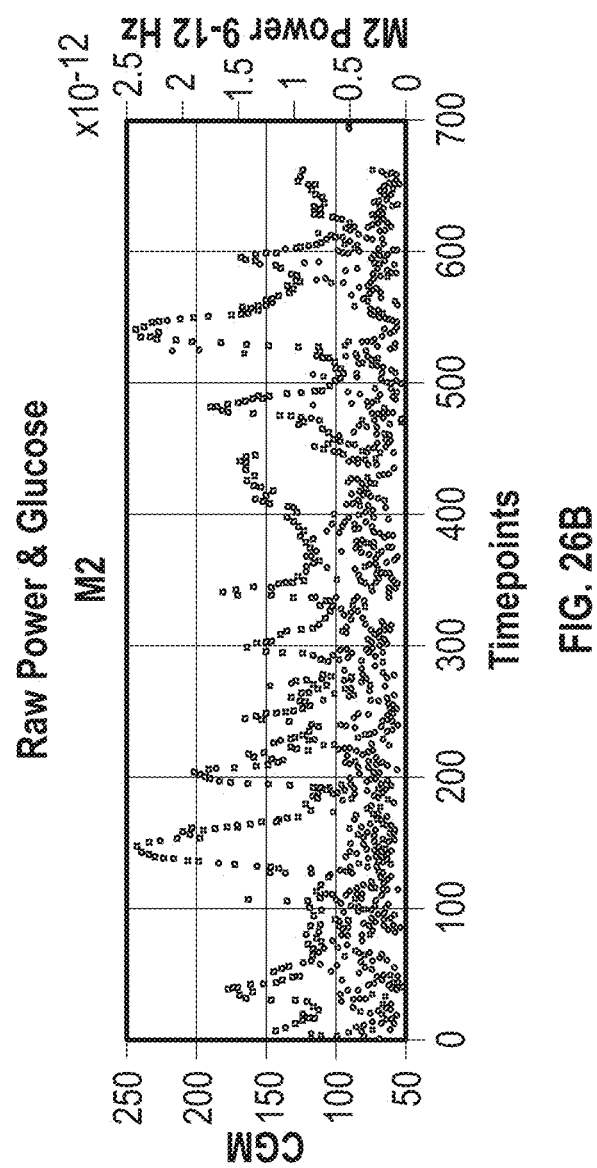
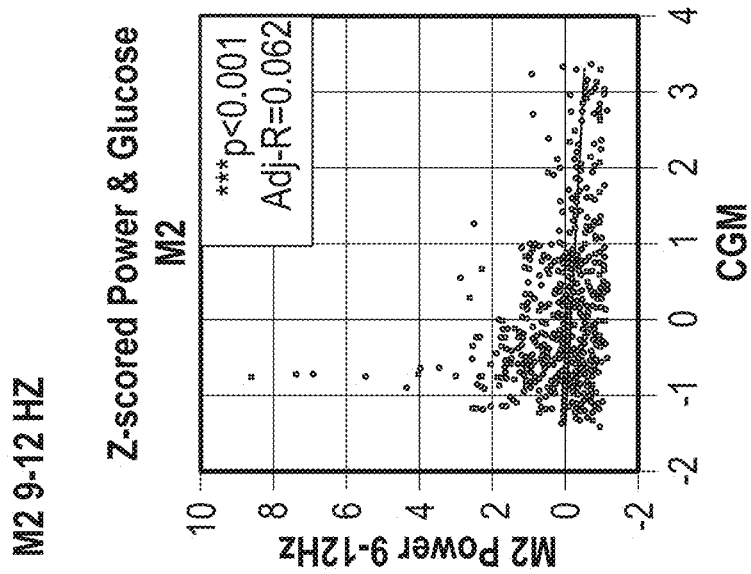
FIG. 26A
FIG. 26B

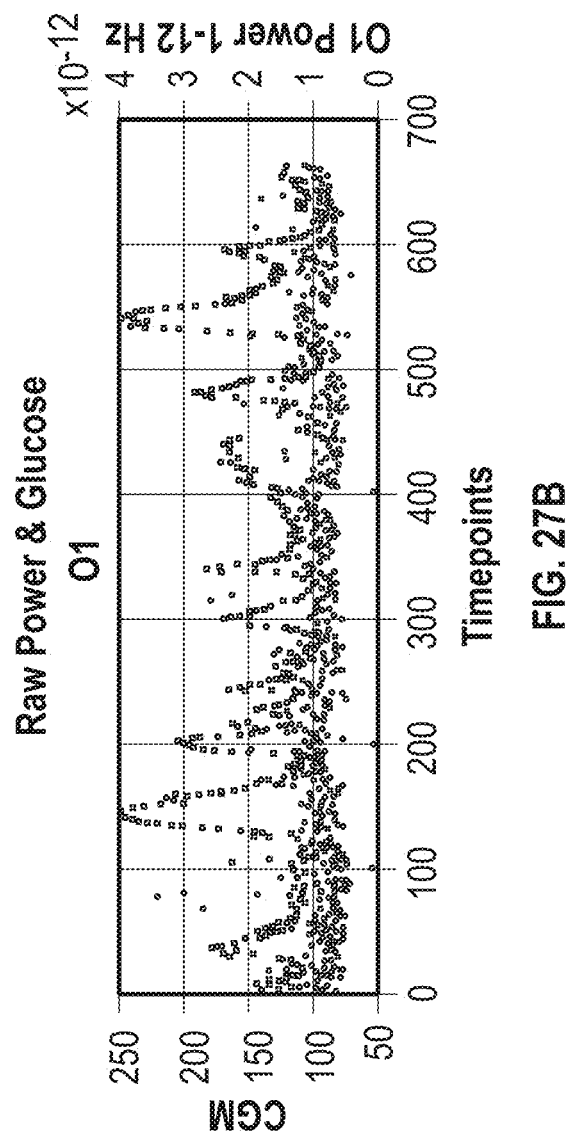
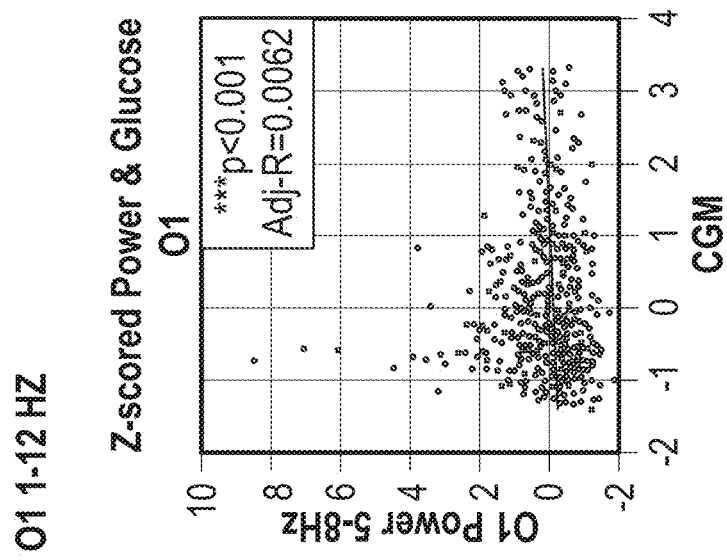
FIG. 27B
FIG. 27A
Example When EEG Time Window is
T1=-11min/T2=-6min

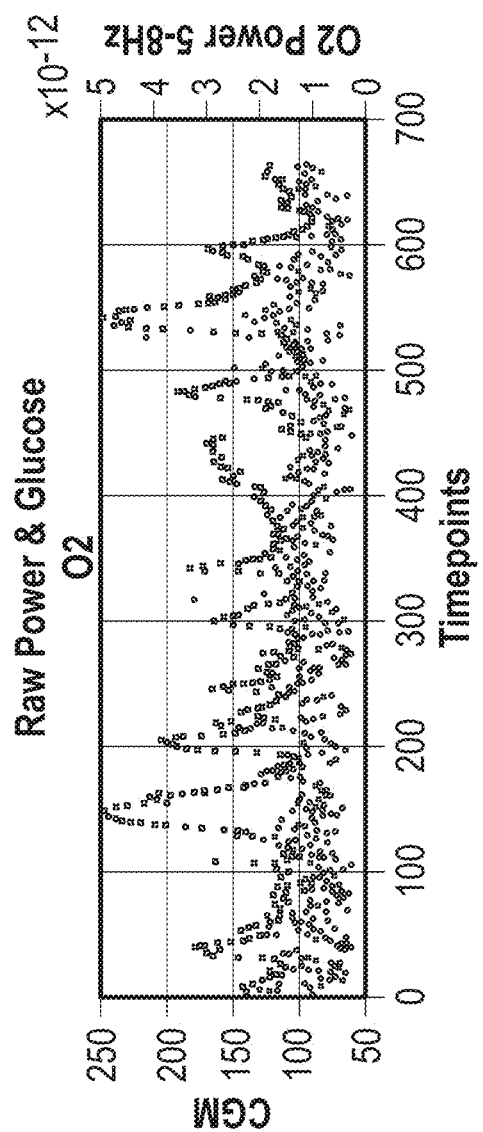
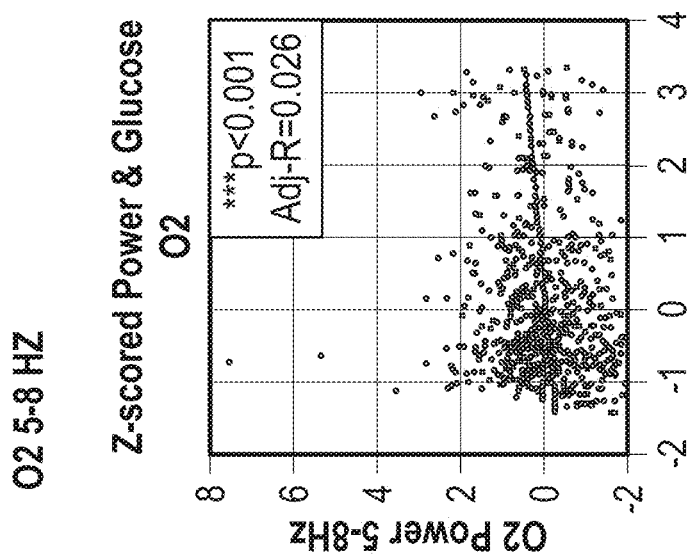
FIG. 28A
FIG. 28B

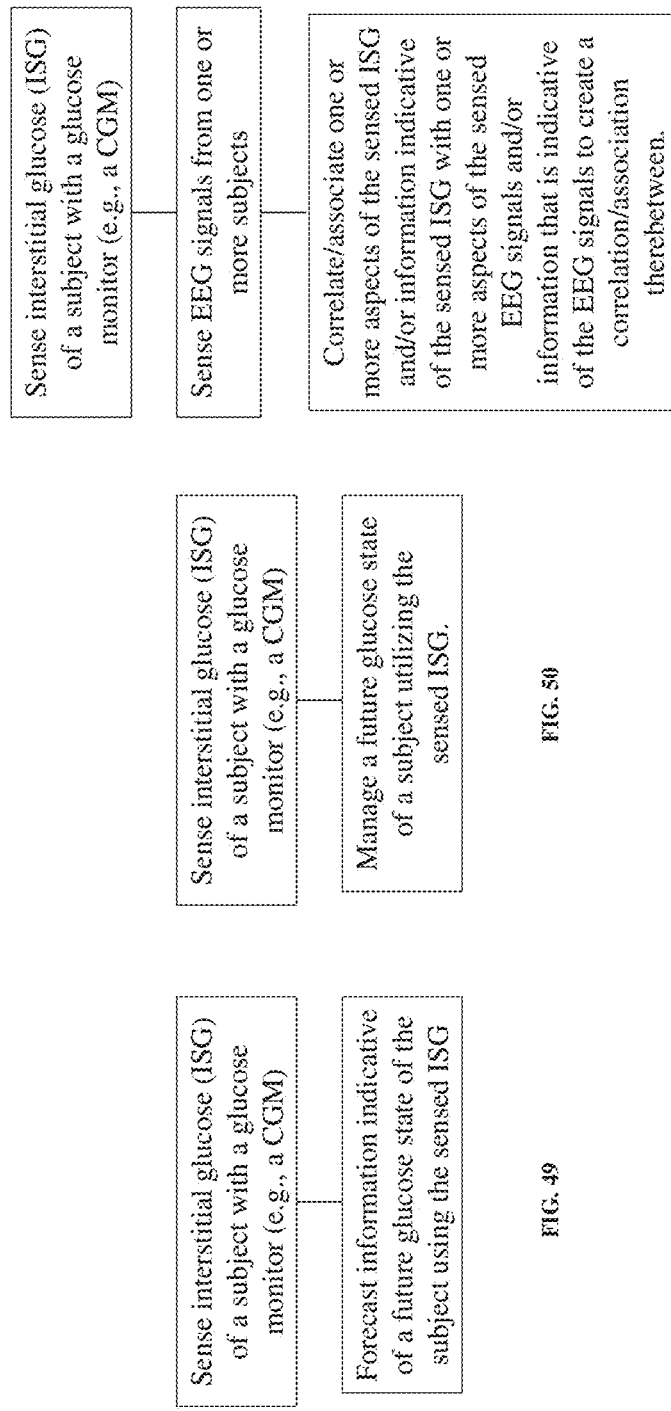

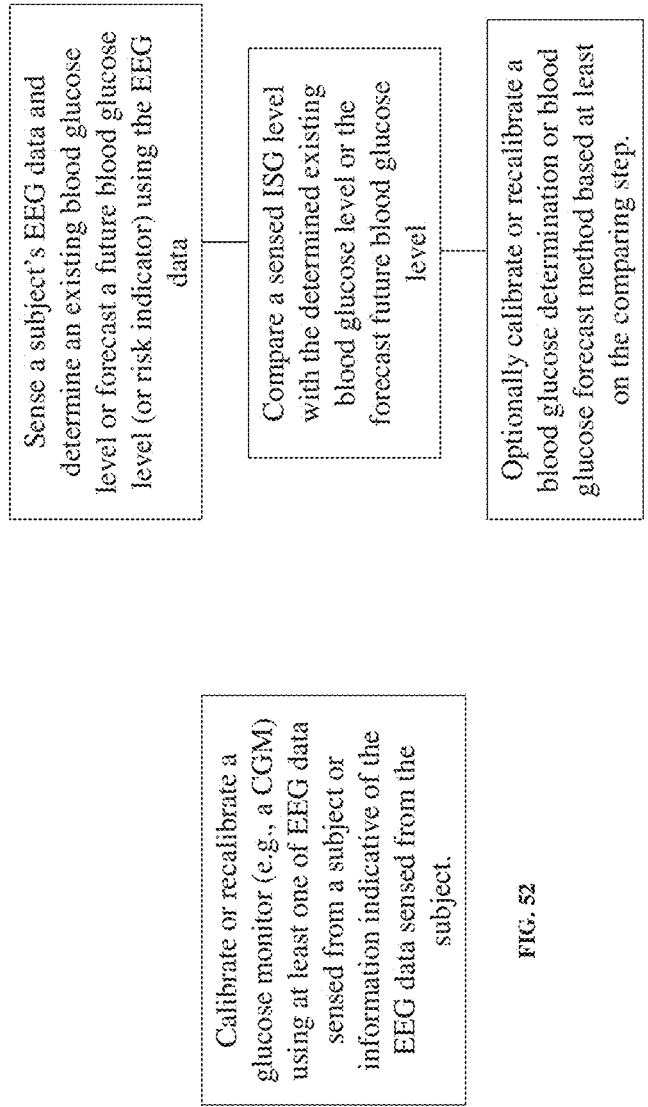

BLOOD GLUCOSE STATES BASED ON SENSED BRAIN ACTIVITY

CROSS REFERENCE TO RELATED APPLICATIONS

This application claims priority to the following U.S. Provisional Patent Applications, the disclosures of which are fully incorporated by reference herein in their entireties for all purposes: Provisional Patent Application No. 63/487,880, filed Mar. 1, 2023; Provisional Patent Application No. 63/503,345, filed May 19, 2023; Provisional Patent Application No. 63/487,845, filed Mar. 1, 2023; and Provisional Patent Application No. 63/487,870, filed Mar. 1, 2023.

INCORPORATION BY REFERENCE

All publications and patent applications mentioned in this specification are herein incorporated by reference to the same extent as if each individual publication or patent application was specifically and individually indicated to be incorporated by reference.

This application incorporates by reference herein the following publications in their entireties for all purposes: U.S. Pat. Nos. 6,572,542; 8,118,741; and 11,020,035.

This application incorporates by reference herein WO/2023/183798A2 in its entirety and for all purposes.

Glucose monitors and/or insulin delivery devices and uses thereof, such as those described in, for example only, U.S. Pat Nos. 9,585,607; 10,827,956; 11,744,943; 11,672,422; and 11,064,917 are incorporated by reference herein in their entireties for all purposes.

PCT publication WO/2023/034820A1 is incorporated by reference herein in its entirety for all purposes. The entire disclosure of U.S. Prov. App. No. 63/238,583, filed Aug. 30, 2021, to which the WO2023034820A1 application claims priority, is also incorporated by reference herein in its entirety for all purposes. The following article is also incorporated by reference herein in its entirety for all purposes: Huang, Y., Wang, J.B., Parker, J.J. et al. Spectrospatial features in distributed human intracranial activity proactively encode peripheral metabolic activity. Nat Commun 14, 2729 (2023) (https://doi.org/10.1038/s41467-023-38253-7).

BACKGROUND

Blood glucose is one of the most important blood parameters to understand and measure, whether on a personal basis or more generalized to a larger segment of a population. Technology exists to estimate blood glucose levels in near real-time. For example only, continuous glucose monitors ("CGM") include a small sensor inserted under the skin, such as the abdomen or arm. The sensor measures the interstitial glucose ("ISG") level, which is believed to be indicative of blood glucose levels. The sensor may sample ISG every few minutes (e.g. five minutes). A transmitter can wirelessly send the information to a monitor, which may optionally be part of an insulin pump, or which may be a separate device, such as a smartphone or tablet. CGMs are essentially estimating existing or current interstitial fluid glucose levels, and because ISG levels follow or lag blood glucose levels by several minutes (e.g., 3-12 mins.), the estimated blood glucose levels (based on the ISG) provided by CGMs are estimates of past blood glucose levels.

There are a wide variety of reasons why understanding glucose levels may be beneficial for a subject. For example only, diabetic patients with glucose monitor systems can include an insulin pump that can automatically initiate insulin injection if glucose levels get too high. A threshold glucose level may be set (stored) in the CGM such that insulin may be delivered once the glucose level reaches the preset threshold. Individualized thresholds may be set for patients, and the thresholds may need to be reset over time (currently at office visits), such as if changes in the patient's life necessitate resetting the threshold (e.g., going through puberty). Currently, the best insulin pumps for diabetes management achieve a peripheral glucose target range of 70 to 180 mg/dL <70% of the time, which is not ideal and still quite broad of a glycemic range.

A desire to understand glucose levels is not, however, limited to diabetic patients. Hypoglycemia, for example, which can require medical attention, is a state in which the blood sugar (glucose) level is lower than the standard range, often considered as a blood sugar of 70 milligrams per deciliter (mg/dL), or 3.9 millimoles per liter (mmol/L) or lower. While hypoglycemia may be related to diabetes management, it can occur and be associated with any non-diabetes medical conditions and/or environments (e.g., in healthy individuals, intensive care unit (ICU) patients, fatigue). Reversing hypoglycemia may include high sugar food or drink (e.g., juice) and/or medicine to raise the blood glucose level. Hypoglycemia, if left untreated, may lead to loss of consciousness and/or seizures.

Additionally, hyperglycemia is a condition when blood glucose levels are higher than the standard range, often considered above 180 milligrams per deciliter (mg/dL). Hyperglycemia, which is commonly linked to diabetes, occurs when the body has too little insulin (the hormone that transports glucose into cells), or if the body can't respond to or use insulin properly. Hyperglycemia can, however, be associated with any non-diabetes medical states or conditions and/or environments (e.g., healthy individuals, ICU patients). If left untreated for long periods of time, hyperglycemia can cause damage to nerves, blood vessels, tissues and organs.

Non-diabetic states, conditions and environments exist where it is desirable or necessary to know blood glucose levels. For example only, ICU patients, who may or may not be diabetic, typically have their blood glucose levels frequently checked, typically using blood from a finger prick, which can be tested on a small strip with a meter that provides the glucose levels.

Additionally, subjects who are pre-diabetic may want to be able to monitor (and optionally takes steps to manage) their glucose levels in an attempt to avoid becoming diabetic.

Additionally still, a subject who may be considered healthy may simply want more information about their body, their health, and their overall well-being, including an understanding of their glucose levels.

Alternative approaches are needed that can provide information about a glucose state of a subject without relying solely on a glucose sensor, and optionally without requiring a glucose sensor at all.

SUMMARY OF THE DISCLOSURE

The disclosure herein is related to health, including overall well-being.

One aspect of this disclosure is related to methods of predicting a glucose state of a subject.

In this aspect, the method includes sensing brain activity signals of a subject and predicting a predicted glucose state of the subject based at least partially on at least some of the sensed brain activity signals.

Sensing brain activity signals of a subject is optionally performed non-invasively. Sensing brain activity signals of a subject is optionally performed using one or more wearable sensing devices, the one or more wearable sensing devices each placed on a location on the head of the subject. A wearable sensing device is optionally sized and configured to fit entirely in a behind-the-ear location of the head, and on skin. A wearable sensing device is optionally sized and configured to be placed at an O1 or O2 location on the head. A wearable sensing device optionally includes sensing electrodes that consist of first and second sensing electrodes (i.e., not more than first and second sensing electrodes, which can be used to sense in a bipolar manner), although alternative wearable sensing device may include more than one pair of sensing electrodes, and may extend beyond just a behind-the-ear location. The method may include sensing single-channel brain activity signals using the at least one pair of first and second sensing electrodes (bipolar sensing).

In this aspect, the method may include inputting the sensed brain activity signals (optionally single channel signals) or processed brain activity signals into a model or algorithm that has been trained to predict a glucose state of the subject based at least partially on the sensed brain activity signals, and optionally trained to predict a glucose state of the subject based at least partially on sensed brain activity signals (e.g., single-channel data).

In this aspect, the method may include predicting, using the trained model, a predicted glucose state of the subject based at least partially on at least a portion of the sensed brain activity signals or processed brain activity signals. In this aspect, predicting is optionally (but not necessarily) at least partially based on brain activity signals from only a subset of frequencies from within a larger range of frequencies including a delta band, a theta band, an alpha band, a beta band, and a gamma band, such as a subset of frequencies within the beta and/or gamma band. In other methods, all frequencies within those bands or ranges may be utilized.

In this aspect, the method may include outputting instructions to initiate a communication indicative of the predicted glucose state based on and in response to the predicted glucose state. The communication that is indicative of the predicted glucose state may optionally be a predicted glucose value (e.g., real-time or predictive value at a time that is subsequent to when the brain activity signals were sensed) displayed on a display of a personal device (e.g., smartphone or smartwatch). The communication that is indicative of the predicted glucose state may optionally be a time history of glucose values displayed on a display of a personal device. The communication that is indicative of the predicted glucose state may optionally be a communication to a care team or other non-subject device (e.g., physician computing device). The communication that is indicative of the predicted glucose state may optionally be an alert when predicted glucose values is trending out of range or is out of a predetermined range. The communication that is indicative of the predicted glucose state may optionally provide automated meal recommendations and/or exercise recommendations.

In this aspect, the method may optionally, depending on if the subject is diabetic or not, communicate insulin and medication needs based on the predicted glucose state (e.g., real-time prediction and/or prediction of a future glucose state).

In this aspect, the method may allow the subject to provide input of data such as time of insulin administration and/or dose, the time medication was administered, the occurrence of a meal, one or more aspect of exercise such as the time of exercise, one or more aspects of stress such as when feelings of stress were experienced, one or more aspect of sleep such as when sleep occurred, and one or more aspects of illness such as the time of illness.

In this aspect, the method may provide for the subject or the subject's care team to mark the occurrence of events directly onto raw brain activity signals tracings (EEG tracings).

In this aspect, the method may include continuously sensing brain activity, or sensing substantially continuously even if there are some brief periods without sensing. In this aspect, the method may optionally include sensing brain activity at one or predefined periods and not sensing at one or more predefined periods, such as during sleep but not when awake, awake but not when asleep, or only sensing upon the subject indicating an event such as the occurrence of a meal, exercise, medication administration, etc.

In this aspect, the method may include continuously streaming or sending of sensed brain activity signals from the wearable to a different device, such as a subject personal device and/or a care-team computing device.

In this aspect, predicting the predicted glucose state optionally comprises predicting the predicted glucose state using a personally trained model that has been trained on data comprising personal data of the subject, the personal data comprising personal non-invasively sensed brain activity signals (optionally single channel signals) and personal glucose values (optionally sensed with a CGM, implantable glucose sensor, and/or external non-CGM sensor such as a smartwatch with optical glucose sensing capabilities, or other non-invasive glucose estimation including RF dielectric spectroscopy devices from KnowLabs, which are incorporated by reference herein.

One aspect of the disclosure is a system adapted for predicting a glucose state of a subject.

In this aspect, the system may include one or more wearable sensing devices (also referred to herein as wearable sensors), the one or more wearable sensing devices adapted to non-invasively sense brain activity signals of a subject. Wearable sensors optionally include a one or more pairs of sensing electrodes, wherein the number of sensing electrodes optionally consists of a single pair of first and second sensing electrodes adapted for bipolar sensing. Wearable sensors are optionally sized and configured to be secured on a head of a subject. Wearable sensors are optionally sized and configured to be secured at a behind-the-ear location and on skin of the subject. Wearable sensors are optionally sized and configured such that at least a portion of the wearable sensor is secured at a behind-the-ear location and on skin of the subject. Wearable sensors may include a communication component for wirelessly sending sensed brain activity signals or processed brain activity signals to a different device. Wearable sensors may optionally include one or more processors in communication with at least two electrodes of the sensor. Wearable sensors may optionally include one or more memory elements adapted to store sensed brain activity signal or processed brain activity signals for at least some period of time. Wearable sensors may optionally include one or more components adapted to process brain activity signals to some extent, such as a filter, an amplifier, A/D converter, and/or a processor.

In this aspect, the system may include, optionally in a subject device such as a smartphone or smartwatch, one or more processors and a memory coupled to the one or more processors, the memory storing computer-program instructions. The computer-program instructions, when executed by the one or more processors, may optionally cause the performance of predicting, using a trained prediction model, a predicted glucose state of the subject that is based at least partially on the sensed brain activity signals (optionally single-channel) or processed brain activity signals.

In this aspect, the computer-program instructions, when executed by the one or more processors, may optionally cause the performance of outputting instructions to initiate a communication indicative of the predicted glucose state based on and in response to the predicted glucose state.

In this aspect, a system as described herein does not necessarily need to include the wearable sensing device, and may comprise a device (e.g., subject device; care-team device) that is separate from the wearable sensing device that includes one or more processors and a memory coupled to the one or more processors, the memory storing computer-program instructions.

One aspect of this disclosure comprises computer executable instructions, that when executed by one or more processors, cause the performance of predicting, using a trained predictive model, a predicted glucose state of the subject that is based at least partially on sensed brain activity signals or processed brain activity signals. This aspect may include any other device, system, method step or other concept in this disclosure.

One aspect of this disclosure is a wearable brain activity signal sensor. In this aspect, the wearable sensor may include any of the additional features described, including in any combination thereof.

In this aspect, a first distance is optionally from 1 mm and 8 mm.

In this aspect, a second distance is optionally from 8 mm to 35 mm.

In this aspect, the wearable sensor may optionally comprise an electronics member that is configured and sized to be releasably coupled with an electrode housing (optionally flexible), the electronics member including a plurality of electrode couplers each sized and positioned to be placed in electrical communication with one of a plurality of electrodes of the wearable sensor when the electronics member is coupled with an electrode housing. An electronics member optionally has a length less than a length of an electrode housing. An electronics member optionally has a length from 10 mm to 50 mm. An electronics member optionally has a width less than a width of an electrode housing. An electronics member optionally comprises a processor and a communications module, the processor arranged to be in communication with a first sensing electrode, a second sensing electrode, and a ground electrode when the electronics member is coupled with an electrode housing, optionally wherein the electronics member further comprises a power source.

In this aspect, at least a portion of a skin-facing surface of an electrode housing is optionally concave.

In this aspect, the wearable sensor optionally further comprises an adhesive layer disposed on at least a portion of a skin-facing surface, the adhesive layer positioned to contact skin when the wearable sensor is worn by the subject.

In this aspect, the wearable sensor optionally further comprises a processor and a communications module embedded within an electrode housing, the processor optionally in communication with a first sensing electrode, a second sensing electrode, and a ground electrode.

In this aspect, the wearable sensor optionally has the following dimensions: a length from 15 mm to 60 mm, a width from 5 mm to 30 mm, and a height from 1 mm to 10 mm.

In this aspect, the wearable sensor optionally has a length from 15 mm to 60 mm.

In this aspect, the wearable sensor optionally has a width from 5 mm to 30 mm.

In this aspect, the wearable sensor optionally has a height from 1 mm to 10 mm.

In this aspect, the wearable sensor is optionally sized, configured and positioned to be worn on a region of a subject that is not visible when viewing the face of the subject.

In this aspect, first, second, and third electrodes are optionally aligned along a length of an electrode housing.

In this aspect, the wearable sensor optionally further comprises one or more of an inertial sensor, an electrodermal activity sensor, or a photoplethysmography sensor.

In this aspect, the wearable sensor optionally is adapted to provide a vibratory alert to the subject.

In this aspect, the wearable sensor optionally is adapted to sense in at least one of single channel mode or dual channel mode.

In this aspect, the wearable sensor may optionally be sized and configured to be worn at a behind the ear location on a subject, comprising: an optionally flexible electrode housing, the flexible electrode housing having a skin-facing surface, the flexible electrode housing flexible to facilitate conformability between the sensor and the subject's skin; only one pair of first and second sensing electrodes secured to the flexible electrode housing and spaced apart at a first distance therebetween; and a ground electrode secured to the flexible electrode housing and spaced from the first and second sensing electrodes, the ground electrode spaced from a nearest of the first and second sensing electrodes at a second distance greater than the first distance, the first and second sensing electrodes and the ground electrode each having skin-facing surfaces, the sensor configured to operate in a monopolar sensing mode between each of the first and second sensing electrodes and the ground electrode, and in a bipolar sensing mode between the first and second sensing electrodes, and the wearable brain activity signal sensor sized and configured to be worn at a behind the ear location on a subject.

One aspect of this disclosure is a method of identifying a predictive aspect of future blood glucose levels for one or more subjects, comprising: receiving glucose levels of the subject using a glucose monitor; receiving brain activity (EEG) signals non-invasively sensed with one or more sensors on the scalp of a subject; determining a temporal lag associated with a relatively higher correlation between one or more features of the brain activity signals and glucose levels; and providing a trained model executable by one or more processors that, when receiving subsequent brain signals, is adapted to predict glucose levels and that predicts glucose levels a time in advance that includes the determined temporal lag.

One aspect of this disclosure is a method of identifying a predictive aspect of future blood glucose levels for a plurality of subjects, comprising: for a first subject, determining a first temporal lag associated with a relatively higher correlation between one or more features of the brain activity signals of the first subject and glucose levels of the first subject; for a second subject, determining a second temporal lag associated with a relatively higher correlation between one or more features of the brain activity signals of the second subject and glucose levels of the second subject;

providing a trained model executable by one or more processors that, when receiving subsequent brain signals, is adapted to predict glucose levels and that predicts glucose levels a time in advance that includes the first determined temporal lag; and providing a trained model executable by one or more processors that, when receiving subsequent brain signals, is adapted to predict glucose levels and that predicts glucose levels a time in advance that includes the second determined temporal lag.

One aspect of this disclosure is a method of predicting blood glucose levels of a subject, comprising: sensing brain activity signals of a subject during an epoch of awake time and during an epoch of asleep time; and predicting blood glucose levels of the subject, wherein predicting during the awake time relies more heavily on one or more features of the brain signals than when predicting during the sleep time, and wherein predicting during the sleep time relies more heavily on one or more features of the brain signals than when predicting during the awake time.

One aspect of this disclosure is a method of monitoring blood glucose levels of a subject while the subject is asleep, comprising: extracranially sensing brain activity signals of a subject while the subject is asleep; obtaining sensed glucose levels with a glucose monitor from worn by the subject while the subject is asleep; and predicting or estimating blood glucose levels while the subject is asleep using the sensed brain activity signals and the sensed glucose levels.

One aspect of this disclosure is a computer-executable method, stored in a non-transitory media, adapted to, when executed by one or more processors, cause the performance of: receiving as input extracranially-sensed EEG data or information indicative of extracranially-sensed EEG from a subject; and creating a visual representation of, on a display of a device, a predicted glucose state based at least partially on the EEG data.

One aspect of this disclosure is a method of training an EEG blood glucose prediction algorithm; comprising: obtaining or receiving an indicator of consumption by a subject; receiving or generating blood glucose measurements from the subject (optionally with a CGM); receiving or generating EEG data from the subject; and identifying one or more features of sensed EEG data from the subject that is predictive of a prandial event.

One aspect of this disclosure is a method of estimating blood glucose levels in a subject, comprising: sensing blood glucose levels of a subject, optionally with a continuous glucose monitor or sensor; sensing EEG data from the subject; and estimating blood glucose levels using at least the sensed EEG data.

One aspect of this disclosure is a computer-executable trained method for predicting a glucose state of a subject, stored in a non-transitory media on a computing device, the trained method adapted to, when executed by a processor, cause the performance of: receive brain activity signals or processed single channel brain activity signals sensed by a wearable non-invasive brain activity signal sensor; predict a glucose state of the subject based at least partially on the brain activity signals or processed single channel brain activity signals; and initiate an output adapted to communicate information indicative of the predicted glucose state.

One aspect of this disclosure is a method of training a prediction model to predict a glucose state of a subject, comprising: providing or receiving non-invasively sensed brain activity signals; providing or receiving sensed glucose level data from the subject; and identifying one or more features of the non-invasively sensed brain activity signals that have a relatively higher correlation with at least some of the one or more sensed glucose level data to train the prediction model with the one or more features and the glucose state, wherein the trained prediction model is adapted to receive as input subsequent non-invasively sensed brain activity signals and predict a predicted glucose state of the subject based on at least the subsequent non-invasively sensed brain activity signals.

One aspect of this disclosure is a method of predicting a glucose state of a subject, comprising: non-invasively sensing brain activity signals using one or more electrodes on a scalp of a subject; inputting the brain activity signals or processed brain activity signals into a trained computer executable model trained to predict a future glucose state of the subject; predicting a predicted future glucose state of the subject using the trained model and based at least partially on the non-invasively sensed brain activity signals or processed brain activity signals, wherein predicting the future glucose state comprises using a personalized temporal lag epoch of time determined for the subject to have a prediction accuracy relatively greater than other epochs of time; and outputting instructions to initiate a communication indicative of the predicted future glucose state based on and in response to the predicted future glucose state.

One aspect of this disclosure is a method of predicting a glucose state of a subject, comprising: non-invasively sensing brain activity signals using a wearable sensor with a communication module adapted for wireless communication during a sleep time of the subject; inputting the brain activity signals or processed brain activity signals into a trained model trained to predict a glucose state of the subject during the sleep-time; predicting a predicted glucose state of the subject using the trained model and based at least partially on the non-invasively sensed brain activity signals or processed brain activity signals; and outputting instructions to initiate a communication indicative of the predicted glucose state based on and in response to the predicted glucose state.

One aspect of this disclosure is a method of predicting a real-time or future glucose level of a subject in a subject, comprising: sensing glucose levels from a subject with a glucose monitor; non-invasively sensing brain activity signals from the subject; and predicting a real-time or future glucose level of the subject based at least on the non-invasively sensed brain activity signals from the subject; and outputting instructions to initiate a communication indicative of the predicted glucose level.

One aspect of this disclosure is a method of calibrating a glucose monitor worn by a subject, comprising: sensing glucose levels from a subject with the glucose monitor; non-invasively sensing brain activity signals from the subject contemporaneously while sensing glucose levels; predicting a predicted glucose level of the subject based on the non-invasively sensed brain activity signals; and calibrating the glucose monitor based at least on the predicted glucose level One aspect of this disclosure is a wearable brain activity signal sensor sized and configured to be worn by a subject, comprising: a flexible electrode housing, the flexible electrode housing having a skin-facing surface, the flexible electrode housing flexible to facilitate conformability between the system and the subject's skin; and first and second electrodes secured to the flexible electrode housing and each having a skin facing surface.

One aspect of this disclosure is a wearable brain activity signal sensor sized and configured to be worn by a subject, comprising: an electrode housing, the electrode housing having a skin-facing surface that is concave in at least a portion of the skin-facing surface; and first and second electrodes secured to the flexible electrode housing and each having a skin facing surface.

One aspect of this disclosure is a method of manufacturing a wearable sensor, comprising: providing a plurality of electrodes including first and second electrodes each having skin-facing surfaces; and forming a flexible overmold disposed partially about the first and second electrodes to secure the relative positions of the plurality of electrodes relative to each other, and wherein the skin-facing surfaces of each of the plurality of electrodes are positioned to face skin.

One aspect of this disclosure is a package including a plurality of wearable brain activity signals sensors therein, each adapted to be adhered to a subject to sense brain activity signals, each of the plurality of wearable brain activity sensors comprising: a flexible electrode housing with a skin-facing surface, and a plurality of electrodes secured to the flexible electrode housing, wherein each of the plurality of electrodes has at least one exposed surface, each of the flexible electrode housings sized and configured to be releasably coupled to an electronics member to facilitate electrical communication between each of the exposed surfaces of the plurality of electrodes and a processor of the electronics member.

One aspect of this disclosure is a package including a plurality of wearable brain activity signal sensors therein, each adapted to be adhered to a subject to sense brain activity signals, each of the plurality of wearable brain activity sensors comprising: an electrode housing with a skin-facing surface, and a plurality of electrodes secured to the flexible electrode housing, wherein each of the plurality of electrodes has at least one exposed surface, each of the flexible electrode housings sized and configured to be releasably coupled to an electronics member to facilitate electrical communication between each of the at least one exposed surface of the plurality of electrodes and a processor of the electronics member.

One aspect of this disclosure is a method of predicting a glucose state of a subject, comprising: non-invasively sensing brain activity signals with a wearable sensor at a behind the ear location, the wearable sensor adapted to sense in at least one of a single channel mode or a dual channel mode, the wearable sensor configured to wirelessly communicate sensed brain activity signals or processed brain activity signals to a second device in wireless communication with the wearable sensor; and inputting the sensed brain activity signals or the processed brain activity signals into a trained model trained to predict a glucose state of the subject based at least partially on the sensed brain activity signals or the processed brain activity signals; predicting, using the trained model, a predicted glucose state of the subject that is based at least partially on the sensed brain activity signals or the processed brain activity signals, wherein predicting the predicted glucose state is based at least partially on brain activity data from only a subset of frequencies from within a larger range of frequencies including a delta band, a theta band, an alpha band, a beta band, and a gamma band; and outputting instructions to initiate a communication indicative of the predicted glucose state based on and in response to predicting the predicted glucose state.

One aspect of this disclosure is a method of predicting a glucose state of a subject, comprising: non-invasively sensing one or more brain activity signals with a wearable sensor positioned at a behind the ear location and on skin of the subject, the wearable sensor comprising a plurality of electrodes including a plurality of sensing electrodes and a ground electrode, the wearable sensor configured to sense in bipolar sensing mode and monopolar sensing mode, the plurality of sensing electrodes consisting of first and second sensing electrodes, wherein the wearable sensor is configured to wirelessly communicate brain activity signals or processed brain activity signals to a remote device; inputting the sensed brain activity signals or the processed brain activity signals into a trained model trained to predict a glucose state of the subject based at least partially on the sensed brain activity signals or the processed brain activity signals; predicting a predicted glucose state of the subject using the trained model and based at least partially on the non-invasively sensed brain activity signals or the processed brain activity signals, wherein predicting the predicted glucose state is based at least partially on only on a subset of frequencies from within 0-50 Hz; and outputting instructions to initiate a communication indicative of the predicted glucose state based on and in response to the predicted glucose state.

One aspect of this disclosure is a system adapted for predicting a glucose state of a subject, comprising: a wearable non-invasive brain activity signal sensor that includes sensing electrodes consisting of first and second sensing electrodes and a third reference electrode and adapted for single channel or dual channel sensing, the wearable sensor sized and configured to be secured at a behind the ear location and on skin of a subject, the wearable sensor including a wireless communication component, a power source and one or more processing components; a subject device configured to receive information wirelessly from the wearable sensor, the subject device including: one or more processors; a memory coupled to the one or more processors, the memory storing computer-program instructions, that, when executed by the one or more processors, causes the performance of: receiving or generating sensed brain activity signals or processed brain activity signals sensed by the wearable non-invasive brain activity sensor; predicting, using a trained prediction model, a predicted glucose state of the subject that is based at least partially on the sensed brain activity signals or the processed brain activity signals, wherein predicting the predicted glucose state comprises predicting based on at least brain activity data from only a subset of frequencies within a larger range of frequencies that includes a delta band, a theta band, an alpha band, a beta band, and a gamma band; and outputting instructions to initiate a communication indicative of the predicted glucose state based on and in response to the predicted glucose state.

One aspect of this disclosure is a method of predicting a glucose state of a subject, comprising: non-invasively sensing brain activity signals with a wearable sensor positioned at a behind the ear location, the wearable sensor adapted to sense in at least one of single channel mode or dual channel mode, the wearable sensor configured to wirelessly communicate sensed brain activity signals or processed brain activity signals to a second device in wireless communication with the wearable sensor; and inputting the sensed brain activity signals or the processed brain activity signals into a trained model trained to predict a glucose state of the subject based at least partially on the sensed brain activity signals or the processed brain activity signals, wherein the trained model is a personally trained model trained on data including personal data of the subject including personal non-invasively sensed brain activity signals and personal glucose values; predicting, using the personally trained model, a predicted glucose state of the subject that is based at least partially on the sensed brain activity signals or the processed brain activity signals, wherein predicting the predicted glucose state is based at least partially on brain activity data from only a subset of frequencies from within a larger range of frequencies including a delta band, a theta band, an alpha band, a beta band, and a gamma band; and outputting instructions to initiate a communication indicative of the predicted glucose state based on and in response to the predicted glucose state.

One aspect of this disclosure is a wearable brain activity signal sensor sized and configured to be worn at a behind the ear location on a subject, comprising: a flexible electrode housing, the flexible electrode housing having a skin-facing surface, the flexible electrode housing flexible to facilitate conformability between the sensor and the subject's skin; only one pair of first and second sensing electrodes secured to the flexible electrode housing and spaced apart at a first distance therebetween; and a ground electrode secured to the flexible electrode housing and spaced from the first and second sensing electrodes, the ground electrode spaced from a nearest of the first and second sensing electrodes at a second distance greater than the first distance, the first and second sensing electrodes and the ground electrode each having skin-facing surfaces, the sensor configured to operate in a monopolar sensing mode between each of the first and second sensing electrodes and the ground electrode, and in a bipolar sensing mode between the first and second sensing electrodes, and the wearable brain activity signal sensor sized and configured to be worn at a behind the ear location on a subject.

One aspect of this disclosure is a wearable brain activity signal sensor sized, adapted and configured to be secured at a behind the ear location on a subject, comprising: a flexible electrode housing, the flexible electrode housing having a skin-facing surface, the flexible electrode housing flexible to facilitate conformability between the sensor and the subject's skin; only one pair of first and second sensing electrodes secured to the flexible electrode housing and spaced apart at a first distance therebetween; a ground electrode secured to the flexible electrode housing and spaced from the first and second sensing electrodes, the ground electrode spaced from a nearest of the first and second sensing electrodes at a second distance greater than the first distance, wherein each of the first electrode, second electrode, and ground electrode having at least one exposed surface, the first and second sensing electrodes and the ground electrode each having skin-facing surfaces, the sensor configured to operate in a monopolar sensing mode between each of the first and second sensing electrodes and the ground electrode, and in a bipolar sensing mode between the first and second sensing electrodes; and an electronics member that is configured and sized to be releasably coupled with the flexible electrode housing, the electronics member including a plurality of electrode couplers each sized and positioned to be placed in electrical communication with one of the exposed surfaces of the first and second sensing electrode or ground electrode when the electronics member is coupled with the flexible electrode housing, the wearable brain activity signal sensor sized, adapted and configured to be secured at a behind the ear location on a subject.

It is understood that any aspect of this Summary may be combined with any other aspect in this Summary.

BRIEF DESCRIPTION OF THE FIGURES

FIGS. 8, 9, 10, 11, 12, 13A, 13B, 14, 15, 16A, 16B, 17A, 17B, 18A, 18B, 19A, 19B and 20 illustrate data, plots and other information from Example 1 herein.

FIG. 23A illustrates a table from Example 2 herein show significant correlations between electrode location, frequency band, and whether it was positive or negative correlation.

FIGS. 25A and 25B show data from an M1 electrode in the 9-12 Hz frequency at a time range of –11 minutes to –6 mm.

FIGS. 26A and 26B show data from an M2 electrode in the 9-12 Hz frequency at a time range of –11 minutes to –6 mm.

FIGS. 27A and 27B show data from an O1 electrode in the 1-12 Hz frequency at a time range of –11 minutes to –6 mm.

FIGS. 28A and 28B show data from an O2 electrode in the 5-8 Hz frequency at a time range of –11 minutes to –6 mm.

FIGS. 44 and 45 illustrates an exemplary wearable sensor locations, with

FIG. 45 showing a behind the ear location.

FIG. 49 illustrates an exemplary method of future glucose state estimation using a CGM.

FIG. 50 illustrates an exemplary method of managing glucose states based on values sensed from a CGM FIG. 51 illustrates an exemplary method of creating an association between ISG data and EEG data.

FIG. 52 illustrates an exemplary method of calibrating a glucose monitor using EEG data.

FIG. 53 illustrates an exemplary method of calibrating a blood glucose prediction method.

DETAILED DESCRIPTION

Figure 1:
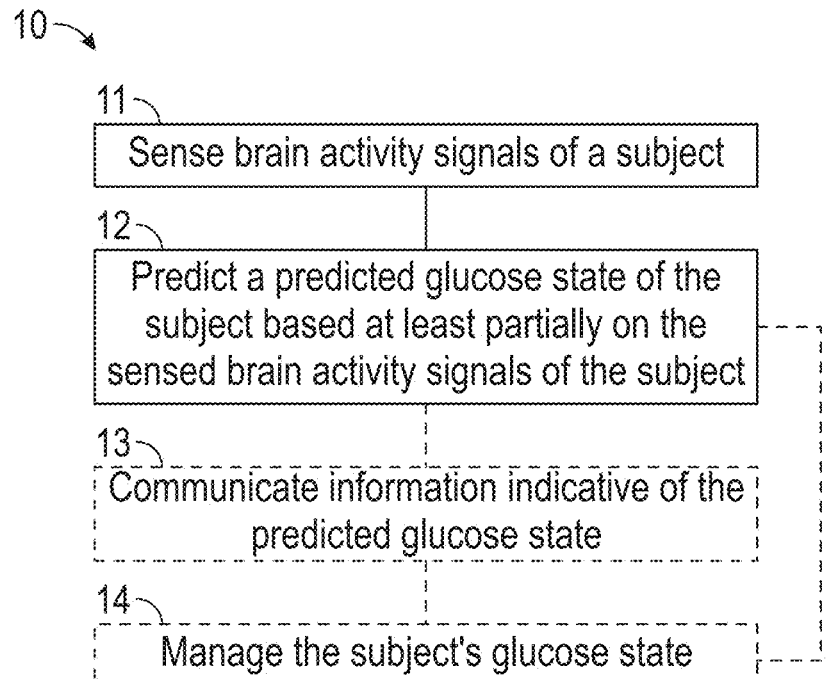
FIG. 1 represents an exemplary method of predicting glucose states.

The disclosure herein is related to health, including well-being.

One aspect of this disclosure is related to predicting or estimating health information about a subject based on one or more types of biosignals sensed from the subject, and/or providing health benefits to the subject based on one or more types of biosignals sensed from the subject.

The predicted health information and/or benefits herein optionally include one or more glucose states of the subject, such as a real-time glucose state or a future glucose state subsequent in time to when the one or more biosignals were sensed from the subject. Predicted glucose states may be based on one or more types of sensed biosignals obtained and/or sensed from the subject. Alternative approaches are needed that can provide information about a glucose state of a subject without relying solely on a glucose sensor, and optionally without requiring a glucose sensor at all.

An exemplary and non-limiting aspect of this disclosure is related to predicting a predicted glucose state of a subject, wherein the predicted glucose state is based at least partially on one or more brain activity signals or data sensed from the subject. Aspects of the disclosure herein provide approaches that facilitate minimally invasive or non-invasive devices and systems that can predict glucose states without requiring an implantable device and that do not rely solely on devices that provide information with a lag time as do glucose monitors that are adapted to measure interstitial glucose.

As reported in the Nature article "Spectro-spatial features in distributed human intracranial activity proactively code peripheral metabolic activity," that is incorporated by reference herein, there was an observed association between intracranially sensed brain activity signals and peripheral glucose activity. Aspects of this disclosure provide an approach to predicting predicted states of a subject based at least partially on brain activity signals sensed minimally invasively, and as shown in examples herein, sensed non-invasively with one or more wearable sensors placed on the scalp of a subject. As discussed above, there may be a variety of reasons for a subject wanting to be informed of their glucose state(s), from managing diabetes to managing overall health and well-being, and everything in between.

As used herein, a "glucose state" may refer to a variety of aspects of the subject's condition. Glucose state may optionally refer to predicted and/or calculated blood glucose values (e.g., 140 mg/dL (or 7.8 mmol/L)), a general characterization of blood glucose values such as a designation between "high," "normal" or "low," a characterization whether the subject is "in range" or "out of range," and/or may be related to blood glucose values and/or interstitial fluid glucose values.

Benefits of some of the approaches herein include being able to predict glucose states without accessing intracranial locations of the subject, and not relying solely on glucose sensors (and optionally do not rely on glucose sensors at all). Aspects of the disclosure include wearable devices that can be worn in an ambulatory manner and are optionally sized and configured to be worn discretely on the scalp of a subject. Additional exemplary benefits of the approaches herein are that the predicted glucose states may optionally be predicted before the glucose state or event occurs and/or the predicted glucose states may be more accurate and reliable than existing glucose monitors. The approaches herein may provide a large number of people with beneficial health information that can enhance their overall health care and/or well-being, including providing access to their glucose state information that people previously did not have access to. While portions of this disclosure may describe predictions for diabetic or prediabetic subjects, the benefits may be realized by the entire population. For example, as is set forth herein, forecasting (future predictions) and/or predicting real-time glucose levels using sensed EEG data may have benefits for a wide variety of individuals, including use by healthy individuals who want more control over their personalized nutrition and health. In fact, some attention has been recently given to using CGM outside of diabetes, and the benefits of forecasting and real-time glucose monitoring using EEG (as described herein) can similarly have benefits outside of diabetes in a wide variety of applications. The following exemplary list provides examples of applications of the innovations herein: athletics; overall health and wellness; gestational diabetes; obesity; metabolic syndromes; personalized glycemic profile (how their body clears and otherwise adapts to glucose); disorders such as stress or anxiety; stress of an infection (sepsis); personalized nutrition; personalized post-meal glycemic profiles.

Using EEG data to predict glucose levels may be more accurate than existing monitoring approaches, such as sensing ISG as is done with existing CGMs. For example, predicting blood glucose states in the future can arm the subject with a predictive outlook on their future blood glucose levels, whether primarily for informational purposes or providing them with actionable information to allow them to improve their health. Additionally for example only, and as described in more details below, methods herein that use EEG data to predict a glucose state (e.g., one or more predicted blood glucose values) during a sleep-state (asleep) may be more accurate information than existing CGMs, including predicting glucose states before they occur, which may be beneficial since some subject's may be more likely to become hypoglycemic while sleeping.

FIG. 1 represents an exemplary and general method of predicting a glucose state of a subject 10. Method 10 includes, at step 11, sensing brain activity signals or data from a subject. Method 10 includes, at step 12, predicting a predicted glucose state of the subject based at least partially on the sensed brain activity signals of the subject. Method 10 optionally includes, at optional step 13, communicating information indicative of the predicted glucose state (e.g., providing information on a display related to glucose state; providing a warning that ranges are trending out of range; communication information to a care-team). Method 10 optionally includes, at optional step 14, managing one or more aspects of the subject's glucose state (e.g., automatically initiating a management step such as delivering insulin; or providing a recommendation to the subject such as recommendation on a time to exercise and/or eat, optionally via a display of a personal subject device).

Sensing at step 11 may comprise, and may preferably comprise, non-invasively sensing brain activity signals. Non-invasive sensing using wearable sensing devices herein can provide a large number of people access to personal health information and the benefits thereof compared with more intrusive approaches (e.g., solely intracranial and/or implantable).

Sensing at step 11 may comprise, and may preferably comprise, non-invasively sensing brain activity signals at one or more specific locations on the head of a subject, and optionally the scalp. The one or more specific locations are, at least in most beneficial uses herein, fewer than all the locations that are typically used during a typical electroencephalogram (EEG) where electrodes are worn at many locations about the head. One of the benefits of approaches herein is that brain activity signals can be sensed and utilized to predict glucose states in an ambulatory manner that is not available with typical full-head EEG recordings in clinical settings, providing myriad individuals access to health information heretofore inaccessible and even unknown. As used herein, "EEG" refers generally to recordings of brain activity electrical signals sensed from a subject at one or more particular locations, but in other uses relative to traditional full head EEG, it may refer to clinical recording of brain activity signals in which signals are obtained with many electrodes placed about the subject's head in a clinical setting.

As described below, Examples 1-3 herein provide data that blood glucose levels may be predicted using brain data recorded from wearable sensing devices that may be placed at one or more behind-the-ear locations (e.g. M1/M2/A1/A2 as shown herein) and/or at one or more occipital locations (e.g., O1/O2 using 10-20 EEG set nomenclature).

Figure 2:
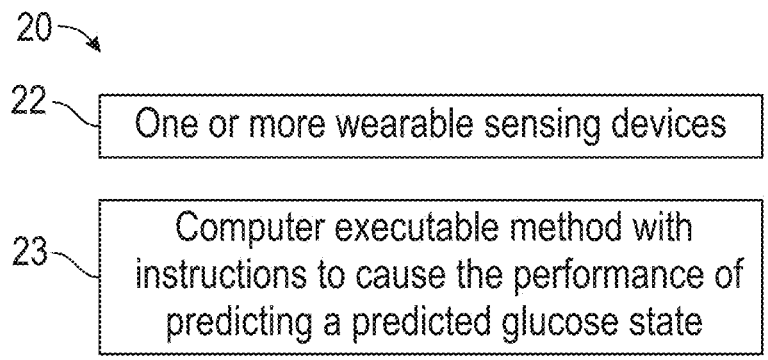
FIG. 2 represents an exemplary system adapted to predict glucose states.

FIG. 2 illustrates an exemplary and general system 20 adapted for predicting a predicted glucose state of subject 21. System 20 includes at least one wearable sensing device 22 (wearable sensor) that is configured to sense brain activity signals from a subject when worn on the head of the subject. System 20 also includes a computer executable method with instructions that cause the performance of predicting a predicted glucose state. The computer executed method may be stored in the wearable sensing device, in a different device (e.g., a personal device) or location (cloud).

Figure 3:
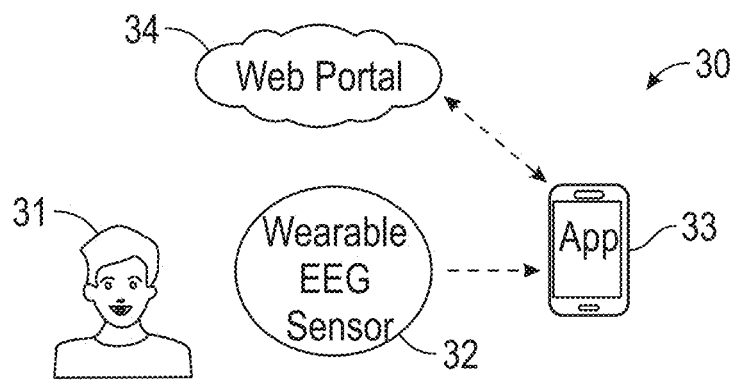
FIG. 3 represents an exemplary system adapted to predict glucose states.

FIG. 3 illustrates an exemplary system 30 that is adapted to predict a glucose state of subject 31. System 30 includes at least one wearable sensing device 32 (wearable sensor) that is configured to sense brain activity signals from subject 31 when worn on the scalp of subject 31. System 30 also includes a device 33 in communication with sensing device 32, wherein the device 33 is adapted to receive information from sensor 32 and output instructions to initiate a communication indicative of the predicted glucose state based on and in response to the predicted glucose state. Device 33 may be a device accessible by subject 31 (e.g., a smartphone or smartwatch) and/or device 33 may be accessible by a care-team for subject 31, optionally one not accessible by subject 31.

Prediction models herein may reside or be stored on one or more wearable sensing devices and/or other device in wireless communication with the wearable sensing device. Depending on processing power, it may be beneficial to store the prediction models on the personal device or care-team device.

Figure 4:
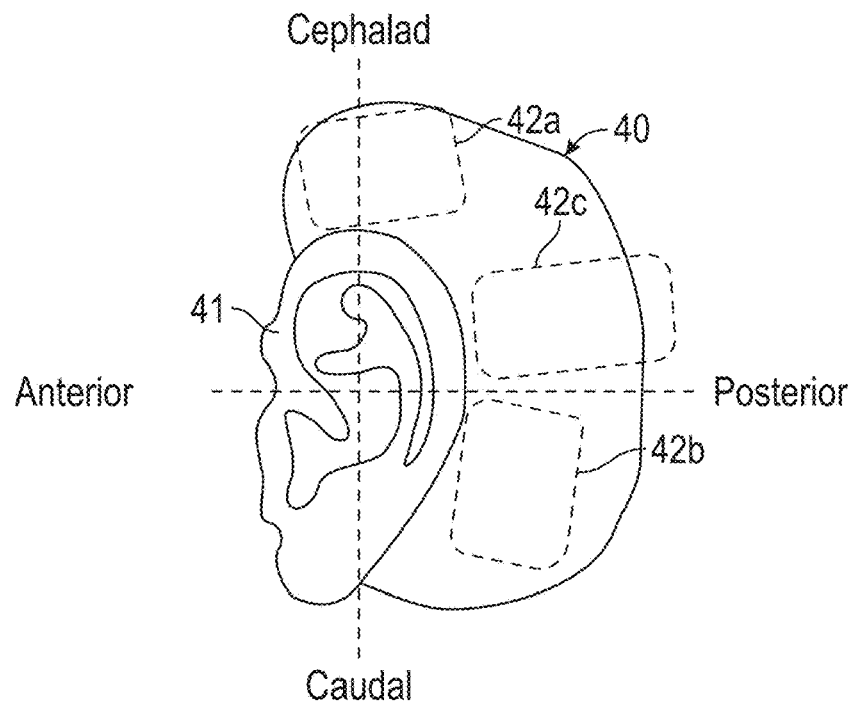
FIG. 4 illustrates exemplary behind the ear locations for one or more wearable sensor.

An important aspect of some of the examples herein is related to wearable sensors that can be worn on the head of a subject and in a location that can reliably and non-invasively detect brain activity signals that can be used to predict predicted glucose states of the subject. FIG. 4 illustrates an exemplary behind-the-ear location 40, which is not meant to refer to a strictly defined region on the subject's head. Location 40 refers to a region on the head that includes surfaces behind (posterior) to the ear as well as surface in the Cephalad direction relative to the ear. Location 40 may also extend to some extend inferior (or Caudal) to the ear. Behind the ear locations as used herein include the locations labeled M1/M2/A1/A2.

Behind-the-ear location 40, including locations proximate the mastoid process, may be beneficial for non-invasively recording brain activity signals because there is a region of skin on which the sensing device may be positioned and maintained during sensing (and without requiring a full-head EEG set-up). FIG. 4 illustrates merely illustrative outer profiles of wearable sensors 42*a*, 42*b* and 42*c* positioned in a behind the ear location. A wearable device need not be placed entirely within a predefined region to be considered to be "behind-the-ear," such as exemplary location 42*c*. All locations 42*a*-42*c* are considered behind-the-ear locations as described herein.

One aspect of this disclosure is related to methods of training machine learning algorithms or models to create a trained glucose state prediction model. Training predictive glucose state models herein may include one or more of supervised or unsupervised training techniques.

Figure 5:
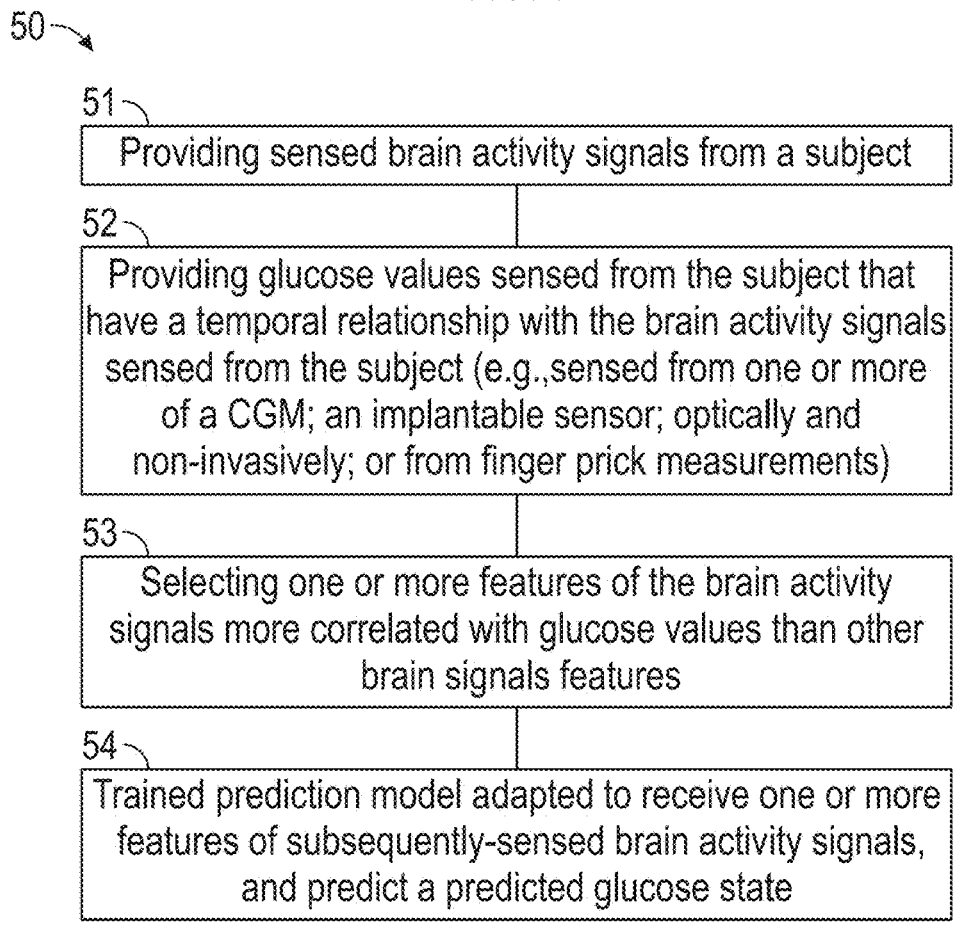
FIG. 5 is an exemplary method of training a glucose state prediction model.

Methods of training models herein may include providing sensed brain activity signals (raw or processed to some extent) and a history of glucose values, whereby the model may select one or more features of the sensed brain activity signals most correlated with one or more aspects of the glucose values. For example, models may select one or more frequencies, frequency ranges, and/or frequency bands most correlated with glucose values. Additionally, for example, models may select one or more most correlated time periods between brain signal sensing and sensed glucose values. FIG. 5 illustrates an exemplary method 50 of training a predictive model. Method 50 includes, at step 51, providing sensed brain activity signals from a subject. Method 50 includes at step 52, providing glucose values sensed from the subject, and which have a temporal relationship with the brain activity signals sensed from the subject. Glucose values may be sensed or measured from one or more of a CGM; an implantable sensor; optical and non-invasive sensors; or from finger prick measurements. Method 50 includes, at step 53, selecting one or more features of the brain activity signals more correlated with glucose values than other brain signals features (e.g., one or more frequencies, frequency ranges, and/or medically established frequency bands). Once trained, at step 54, the model is adapted to receive or generate as input one or more features of subsequently sensed brain activity signals (e.g., brain signals within one or more frequency bands), and predict a predicted glucose state based at least partially on the brain activity signals.

Figure 6:
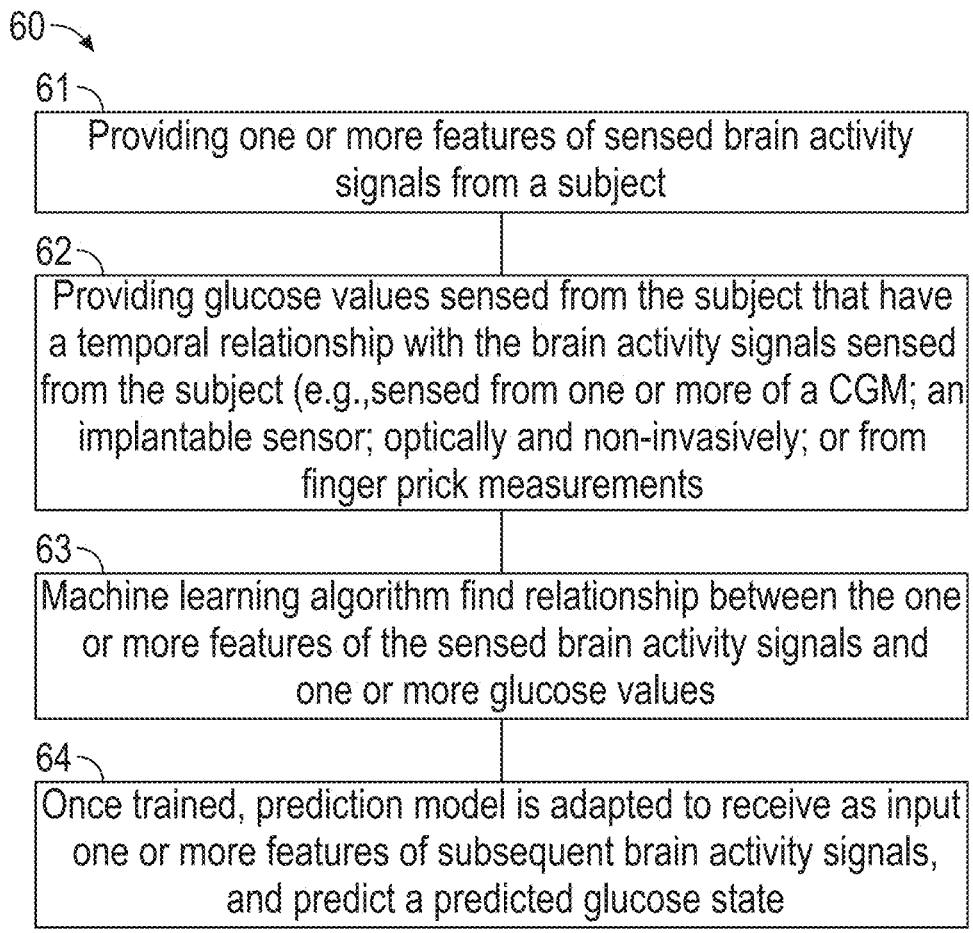
FIG. 6 is an exemplary method of training a glucose state prediction model.

Methods of training models herein may include providing a model with one or more features of sensed brain activity signals (e.g., one or more frequencies, frequency ranges, and/or medically established frequency bands) as inputs with glucose values as targets. Once trained, the model can predict a predicted glucose state based at least partially on subsequently received brain activity signals that include the one or more features. FIG. 6 provides an illustrative method 60 of training predictive models herein. Method 60 includes, at step 61, providing one or more features of sensed brain activity signals from a subject. Method 60 includes, at step 62, providing glucose values sensed from the subject that have a temporal relationship with the brain activity signals sensed from the subject (e.g., sensed from one or more of a CGM; an implantable sensor; optically and non-invasively; or from finger prick measurements). Method 60 includes, at step 63, the learning algorithm finding or determining a relationship (functions/parameters) between the one or more features of the sensed brain activity signals and one or more glucose values. Method 60, at step 64, includes, once trained, the prediction model is adapted to receive as input one or more features of subsequently received brain activity signals, and predict a predicted glucose state.

The glucose state prediction models or methods herein may comprise computer executable instructions executable by one or more processors, and may be stored in any device, such as a wearable sensor, a subject device, a care-team computing device, and/or a cloud device that is adapted to be in communication with any of the devices herein.

Features of brain activity signals that may be used in training and/or during the prediction step may include a variety of features of brain activity signals. For example, features may include powerband activity in certain frequencies, such as one or more frequencies between 0-50 Hz. For example only, features may include powerband activity in one or more of the delta band (0.5-4 Hz), theta (4-7 Hz), alpha (8-13 Hz), beta (13-30 Hz), gamma (e.g., 30-60 Hz).

A mere example of a machine learning method can be adapted to identify a subset of the most important features from non-invasively sensed brain activity signals from one or more single channel locations, and then subsequently fit a linear regression model using the reduced set of features, implemented examples of which are described below.

Figure 7:
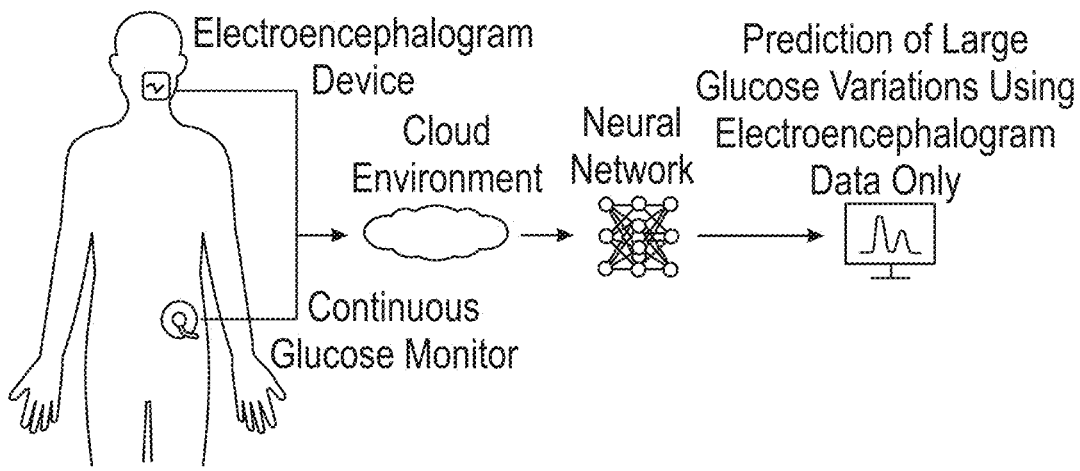
FIG. 7 illustrates an exemplary system and/or method for training and/or prediction.

FIG. 7 illustrates a merely exemplary system and method of training models and using the trained models to predict predicted glucose states, any aspect of which may be incorporated into any training and/or prediction method herein. In exemplary FIG. 7, brain activity signals and glucose values sensed from a CGM are shown to be used in the training process, and once trained, the model is adapted to predict glucose states based on subsequently recorded brain activity signals/data.

Any of methods/algorithms herein may optionally be trained on one or more of normal/healthy individuals, hyperglycemia (e.g., diabetes; hyperglycemia ICU, sepsis, traumatic brain energy; diabetic ketoacidosis) or hypoglycemia states. Any of methods/algorithms herein may optionally be trained on data from the general population, some subset of the population, or personally trained based solely on data from an individual.

Training methods herein may include training on real-time glucose state values (i.e., predicting real-time blood glucose values), or training on future glucose states (predicting a glucose state at one or more times that are in the future relative to when the non-invasively sensed brain activity signals were sensed by a wearable sensor.

Preferably, trained prediction models herein have a relatively high accuracy for predicting blood glucose levels (optionally future predictions), although it is envisioned that it may not be critical that the accuracy be at or above a particular threshold, or consistently at a particular threshold, as having some degree of accuracy can still provide benefits, such as if, for example only, the predictions are used with other types of glucose monitors and sensors. Training methods herein can be adapted to select one or more features of brain signal data most correlated with glucose values.

As mentioned above, brain activity signals may be trained on glucose state data regardless of the manner in which the glucose state data is derived. For example only, brain activity signals can be trained on blood glucose values/levels sensed from existing CGMs, from measured finger prick blood glucose values (measured with a meter), blood glucose values from systems that are configured to optically detect glucose values (e.g., a smartwatch), or implantable sensors that sense glucose at a location more invasive than CGMs (e.g., from within a blood vessel). Trained models herein are adapted to predict a glucose state (e.g. values), and the "state" may be based on the manner in which the values were initially detected or sensed. It is thus understood that the glucose state predictions as described herein may be predictive based on the blood glucose values and the manner in which they were obtained or sensed. Regardless of the manner in which the glucose values are sensed, prediction models based on that data can still provide a predicted state, which provides the subject the predicted values before they occur.

While there may be instances where general features may be used to predict a glucose state for at least parts of a population, there may be a need or preference to determine one or more features of sensed brain data for a particular subject (patient specific) that provides more accurate blood glucose prediction (e.g., due to a higher correlation between the one or more features and glucose levels). The phrase features as used herein in this context can refer to a variety of patient parameters, such as, without any limitation, location of one or more wearable sensors (e.g., using one or more of: one or more behind the ear location or one or more of O1/O2 locations); one or more frequency bands (e.g. alpha, beta, gamma, theta); one or more frequency ranges (e.g., 0-50 Hz, or any subrange within 0-50 Hz, and not necessarily the discrete "bands"), whether the range spans multiple bands or not; one or more particular and discrete frequencies; features related to brain signal sensing (e.g., AUC, Power, Phase synchrony or coherence between sensors); predictive temporal lag with higher accuracy-better correlation (examples of which are described below), etc.

In some aspects, developing a prediction forecasting method may include determining one or more features of extracranially and non-invasively-sensed brain activity signals that are more correlated with future glucose levels, which facilitates greater accuracy in predicting future glucose states, optionally in the absence of requiring blood glucose sensing (such as with a CGM, invasive, or non-invasive monitor). In these applications, while sensed glucose data may initially be used to develop or train predictive methods (e.g. supervised and/or unsupervised), the use of trained models (e.g., in a consumer product) may be adapted to rely on one or more features of non-invasively sensed brain activity data (from one or more wearable sensors) that can be used to predict a glucose state without necessarily requiring blood glucose measurements. In these aspects, peripheral markers/measures may optionally be used that can increase the predictability of a glucose state (blood glucose values) with brain signals, such as any of the other patient biosignals herein (e.g., heart rate, heart rate variability, ECG, skin conductance, etc.).

The example that follows is an illustrative, non-limiting, example of a process or method of training a model or method that includes determining or selecting one or more features in non-invasively sensed brain activity signals from a wearable sensor adapted for single channel sensing (or at least operable in bipolar sensing even if optionally also operable for monopolar sensing), as is shown in FIG. 5. Once trained, the model is adapted to predict future blood glucose levels based on subsequently received single channel EEG data. Alternatively, one or more features can be established as inputs and used to train a predictive model with glucose data as targets (FIG. 6).

Example 1

In this non-limiting example, data from 1 subject with type 1 diabetes and 3 non-diabetic subjects was sensed over the course of several days to about 45 days. The data that was sensed included brain activity signals or data sensed while wearing a wearable non-invasive single channel brain activity sensor, such as a sensor described in or similar to the single channel sensors in U.S. Pat. No. 11,020,035, worn unilaterally at a location behind the ear on the scalp (skin), examples of which are shown in FIG. 4 (optionally one of an M1/M2/A1/A2 location). Additionally, interstitial glucose levels were also contemporaneously sensed using a commercially available CGM traditionally worn and used.

While a variety of software tools may be used (e.g. Python), the example herein utilized MATLAB® software.

While the following example includes several steps, it is understood that this is meant to be illustrative and enabling, but that it is an exemplary method and in other methods not all of these steps are necessarily performed or in this order. After sensing raw brain activity signals, the raw brain activity signal data may undergo data conversion, such as converting it into a particular toolbox, depending on the software used, for processing (e.g., convert the brain activity signal data into fieldtrip format for processing). The raw converted data is shown in the plot in FIG. 8.

The converted data was filtered with a low pass filter (50 Hz) and high pass filter (5 Hz), but other filters may be used (e.g., high pass 1 Hz, low pass 70 Hz). After filtering, the data was plotted, as shown in FIG. 9. In this example, 5-50 Hz signals were processed, but in other examples other ranges may be processed such as 0.5-50 Hz. Signals were epoched into 5-minute segments, and single time points were rejected if they fell outside of 3.5 median average deviations from the median signal amplitude. Further, entire epochs were rejected if their power×frequency curve for that time bin did not follow the physiologically-defined 1/f curve.

Figure 11:
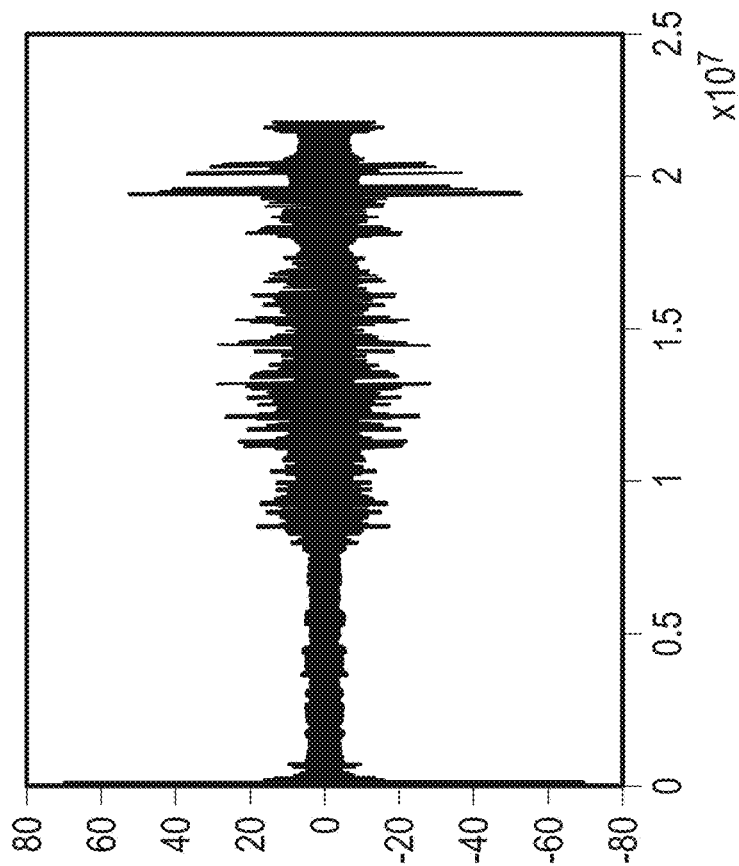
Figure 10:
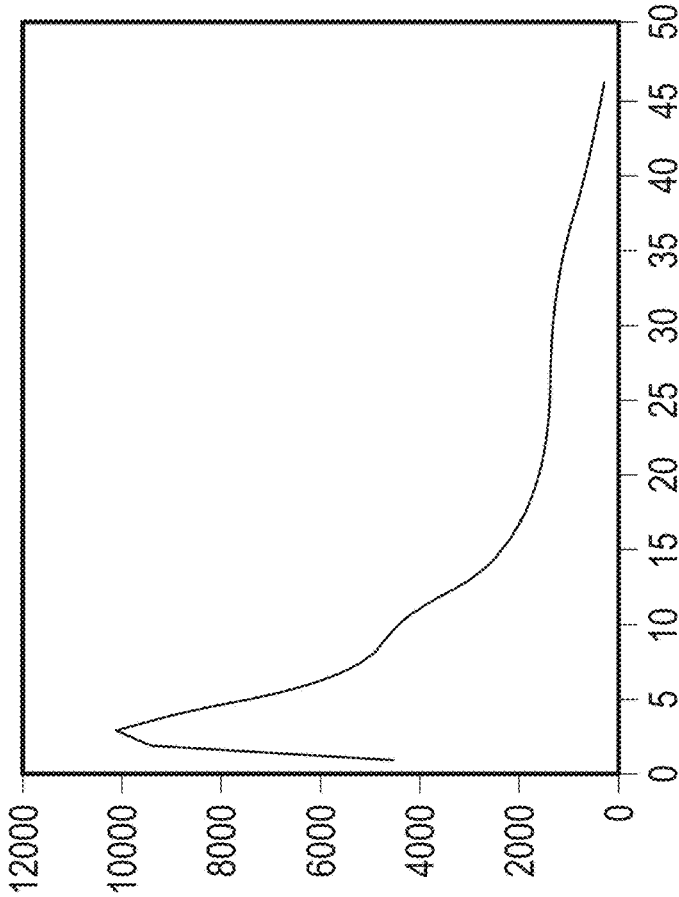
Figure 12:
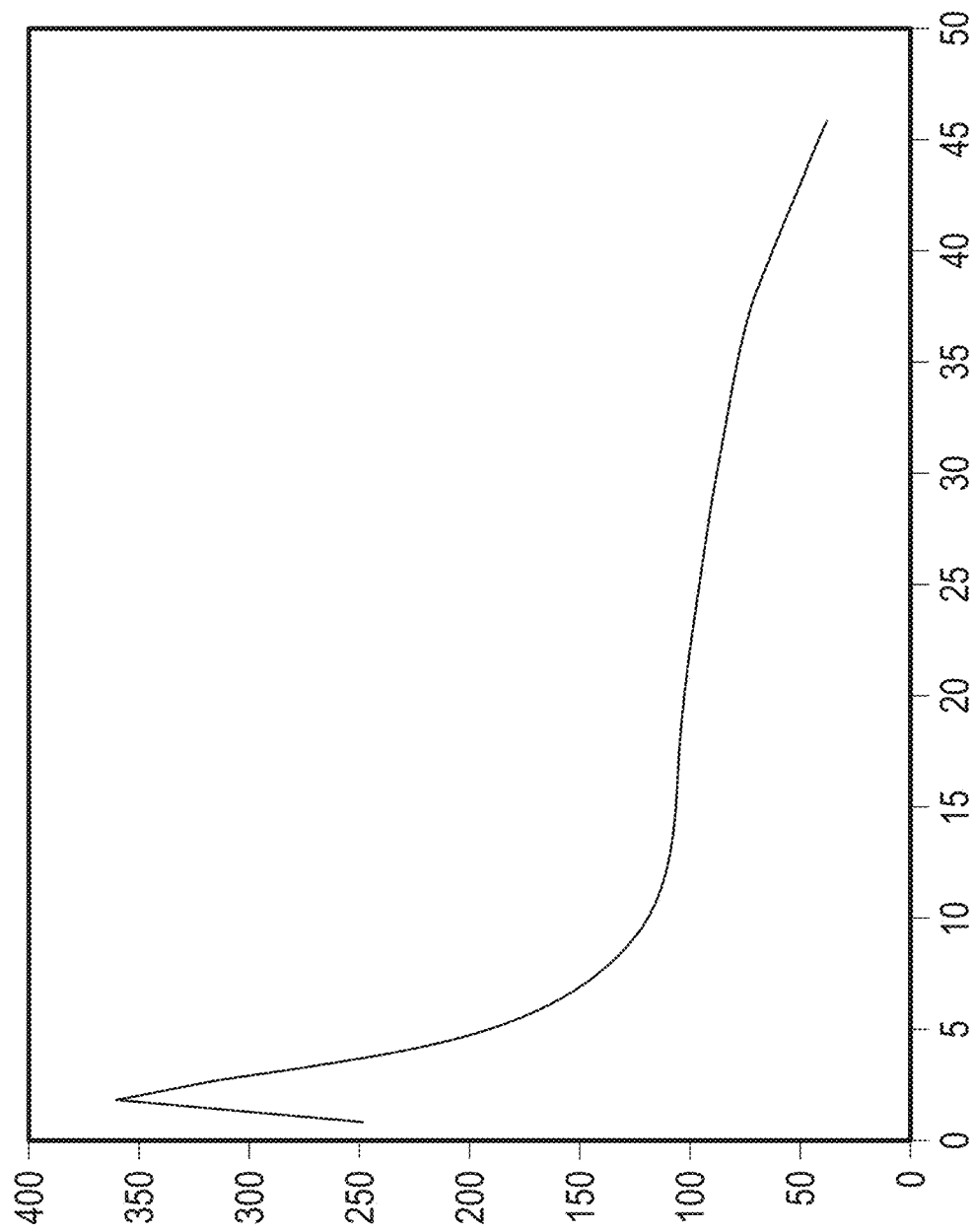
Figure 13B:
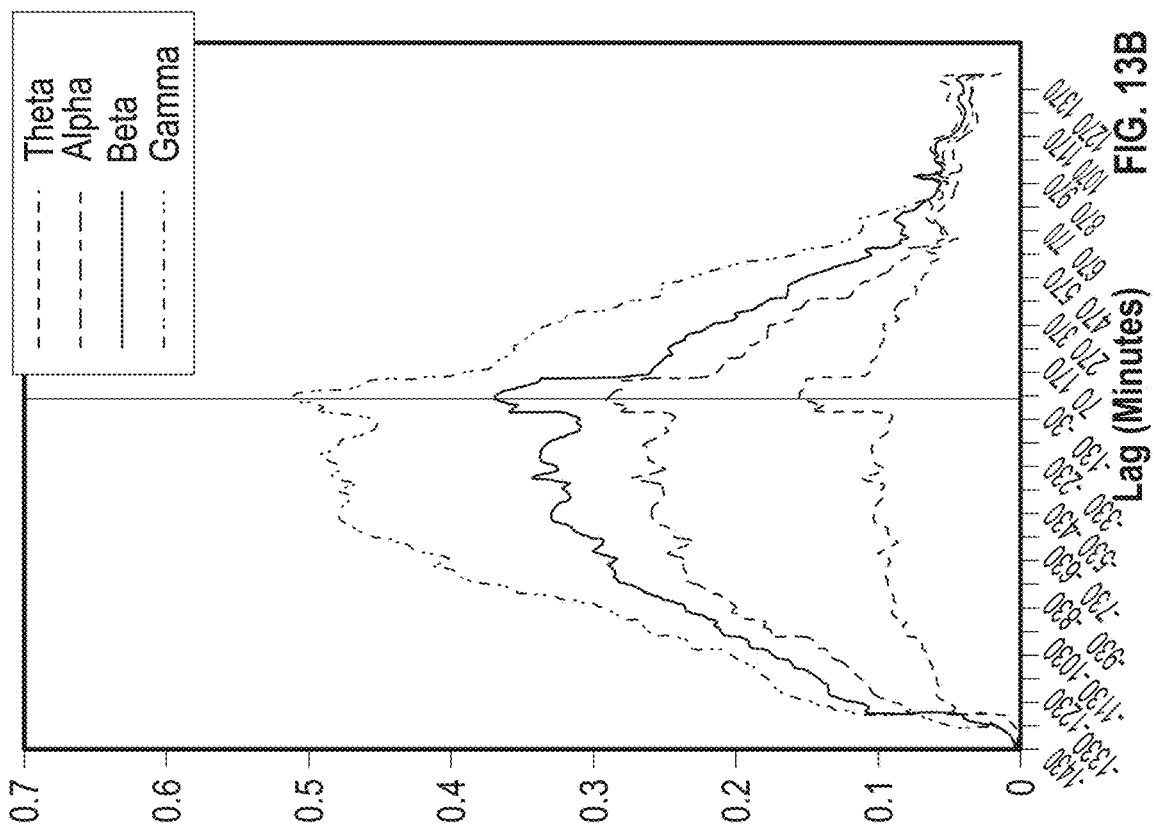
Figure 13A:
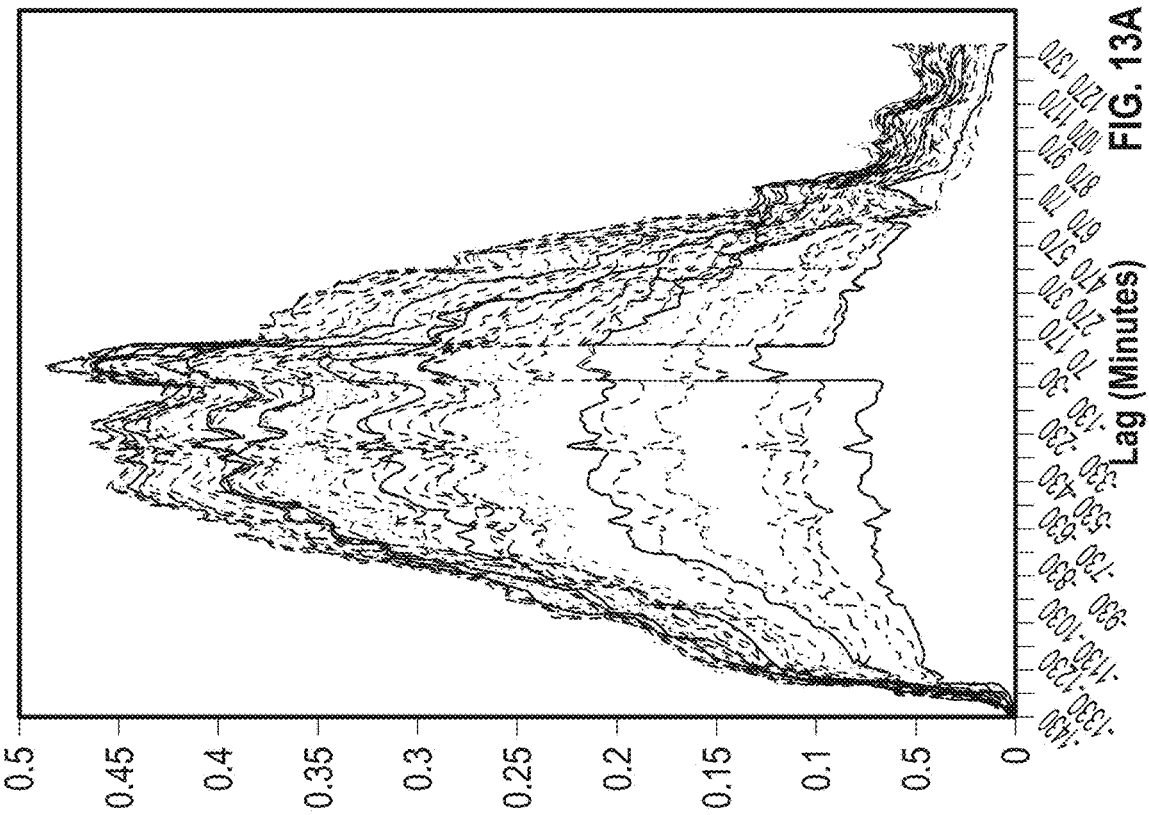

A power analysis was then performed for the range 5-50 Hz, in 1 Hz intervals, and the power fast fourier transform (FFT) was plotted, as shown in FIG. 10. An optional artifact rejection step was performed, which included binning the data into 5-minute periods. Spikes were removed that exceeded a certain median average deviation (MAD; 3.5 MAD), and the data without spikes was then reshaped and plotted, as shown in FIG. 11. A power analysis was then performed again after the spikes were removed. The FFT was plotted, as shown in FIG. 12.

Training predictive methods that are trained to predict a subject's blood glucose state (real-time blood glucose or future blood glucose) may comprise receiving as inputs one or more aspects of processed brain activity signals (e.g., from a wearable sensor adapted to record a single channel (e.g. with a single pair of sensing electrodes), but wherein the wearable sensor may also be adapted to record in monopolar mode with a third referential electrode, examples of which are provided herein), and sensed glucose data (e.g., glucose values). In this particular example, this was performed individually for each subject, and is illustrative of the optional personalized training approach that may be used (or which may be necessary for accuracy) to train predictive models herein.

Next, the glucose monitor data was overlapped with or aligned in time with the brain activity data. In this example, one day of data was overlapped/aligned at a time, but other time periods can be used. The process further included matching the sampling rate of the brain activity signals and the glucose data. The process further included correlating all glucose data and brain activity data, running cross correlations (and plotting, an example of which is shown in FIG. 14A), averaging individual frequencies into bands, and running cross correlations per band (and plotting, an example of which is shown in FIG. 14B). The process further included running correlations for sleep and awake time periods, optionally extracting indices that fall during standard sleep and wake time periods. The process further included, for each of sleep and awake time periods, extracting brain activity signals and glucose data, correlating frequency data, and averaging data into bands and correlating the bands. The correlations can be plotted or otherwise analyzed.

Figure 14:
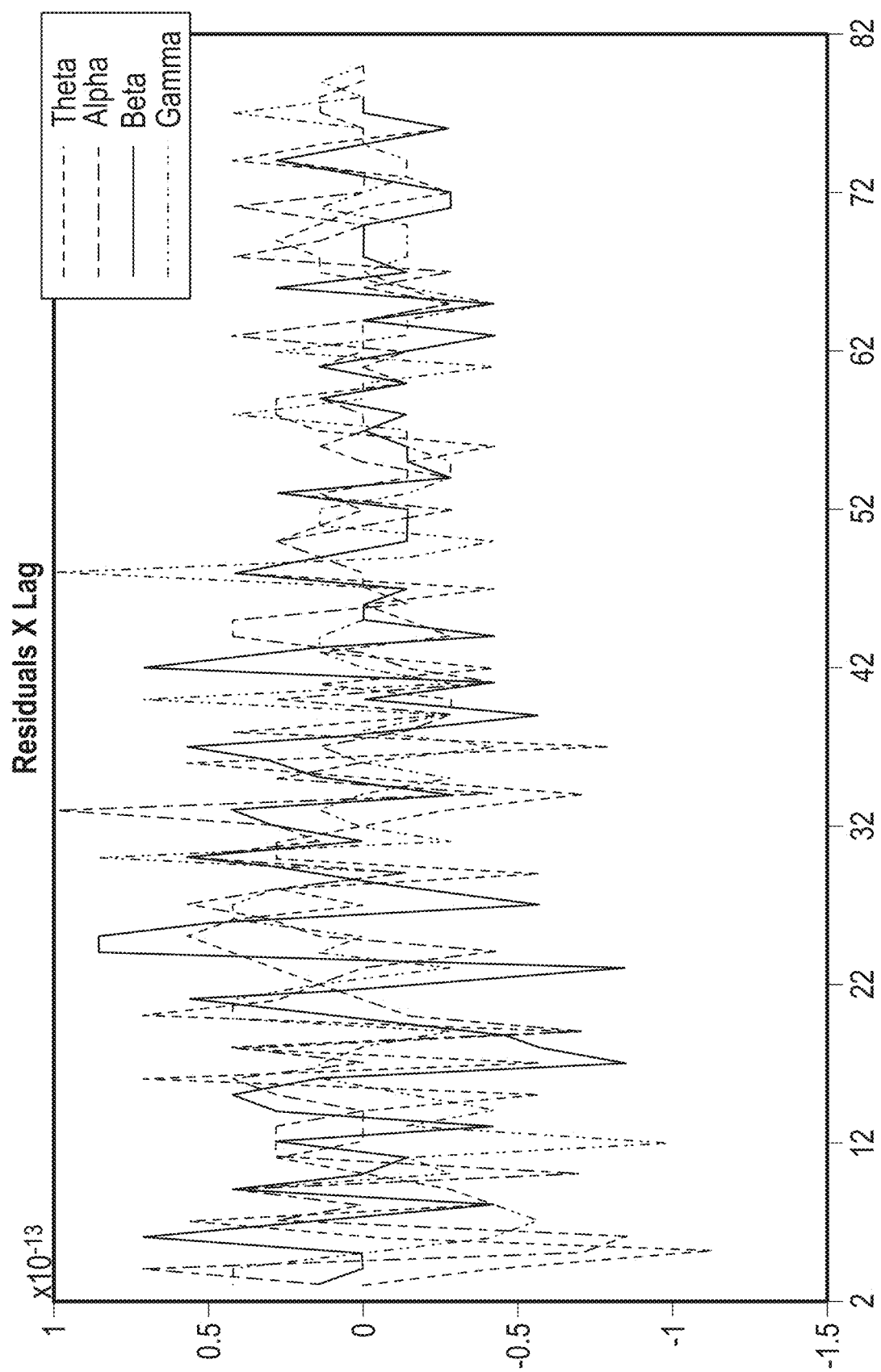
Figure 15:
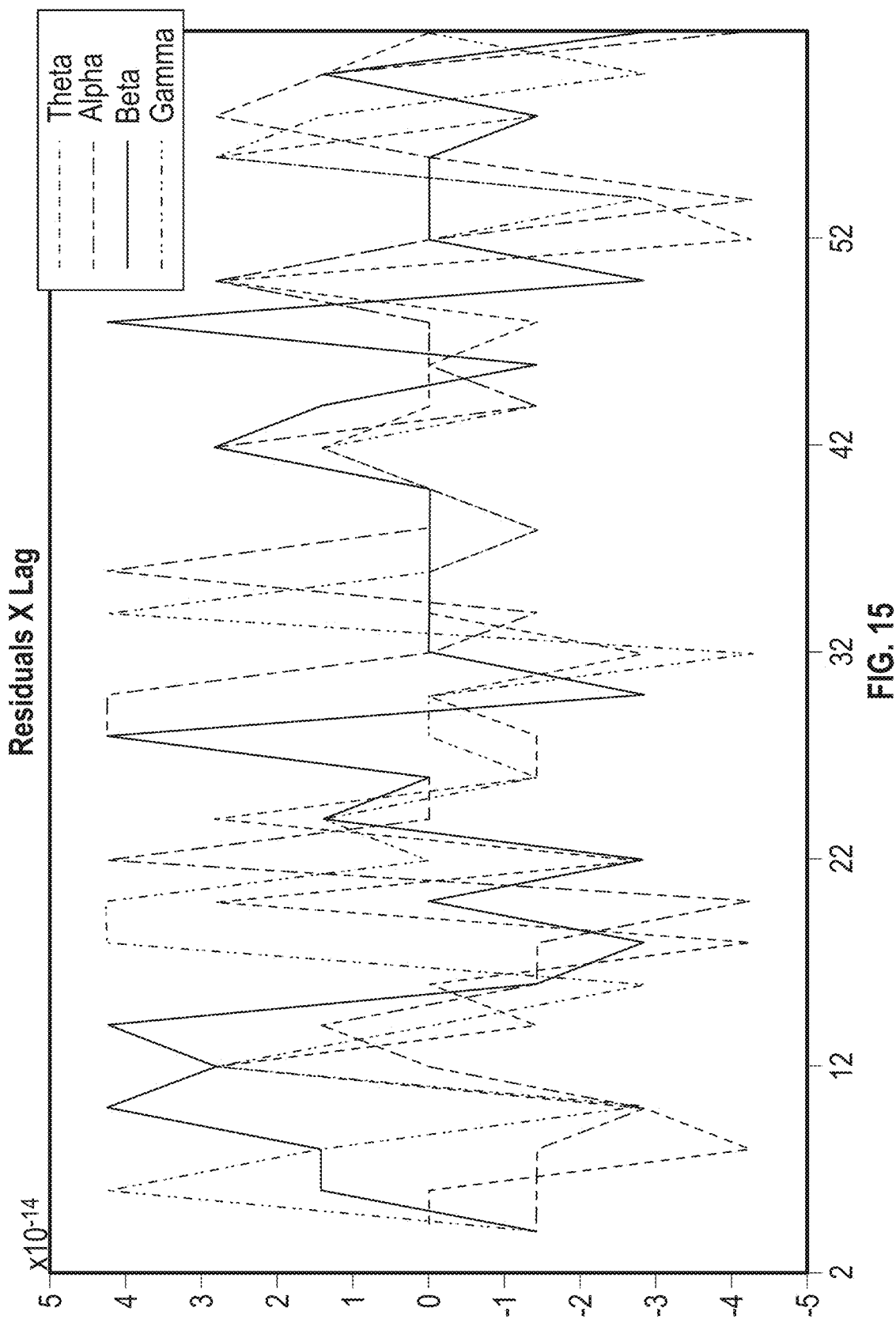

The process further included developing lag indices of, for example, 10-minute intervals, but other intervals can be used, such as, for example without limitation, from a 1 mm lag to a 20-minute lag, including any specific time interval therein (e.g., 5 min lag, 8 min lag, 15 min lag). For each lag, for each frequency band, linear mixed-effects (LME) model analysis was run with predicted blood glucose and fixed variable EEG. Residuals between the model and actual values of blood glucose were plotted, which are shown in FIGS. 14 and 15 for the asleep and awake correlations.

Figure 16A:
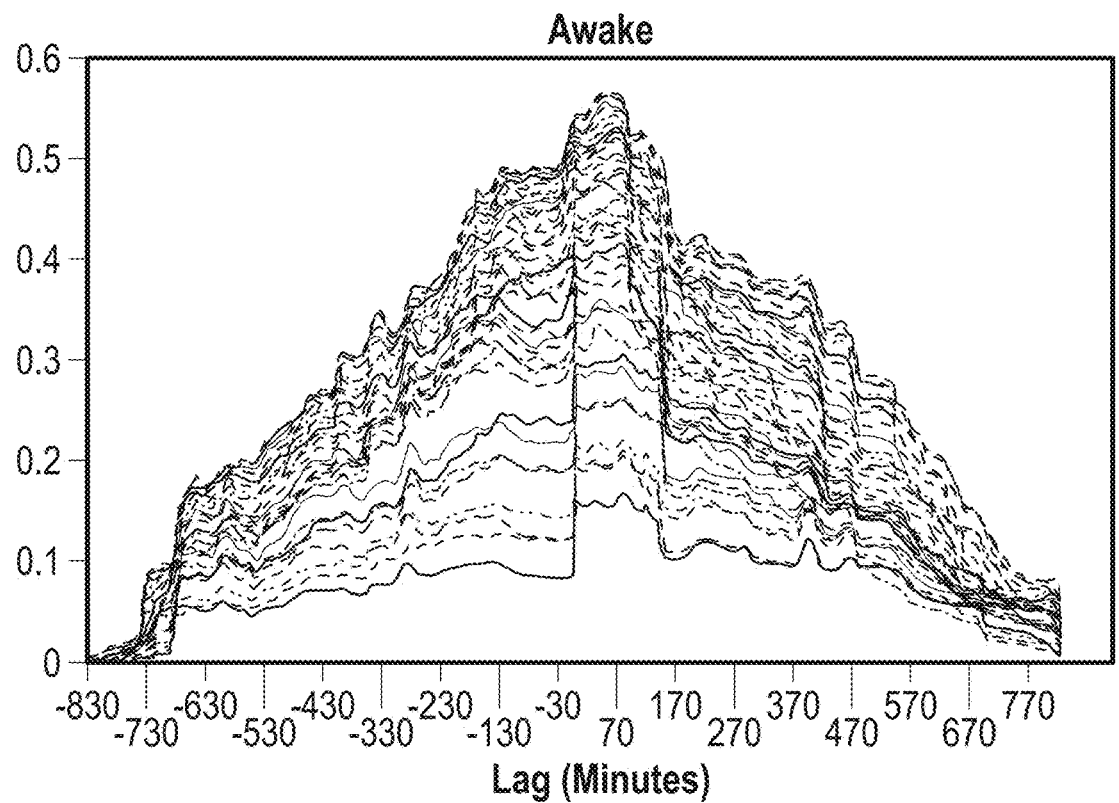
Figure 16B:
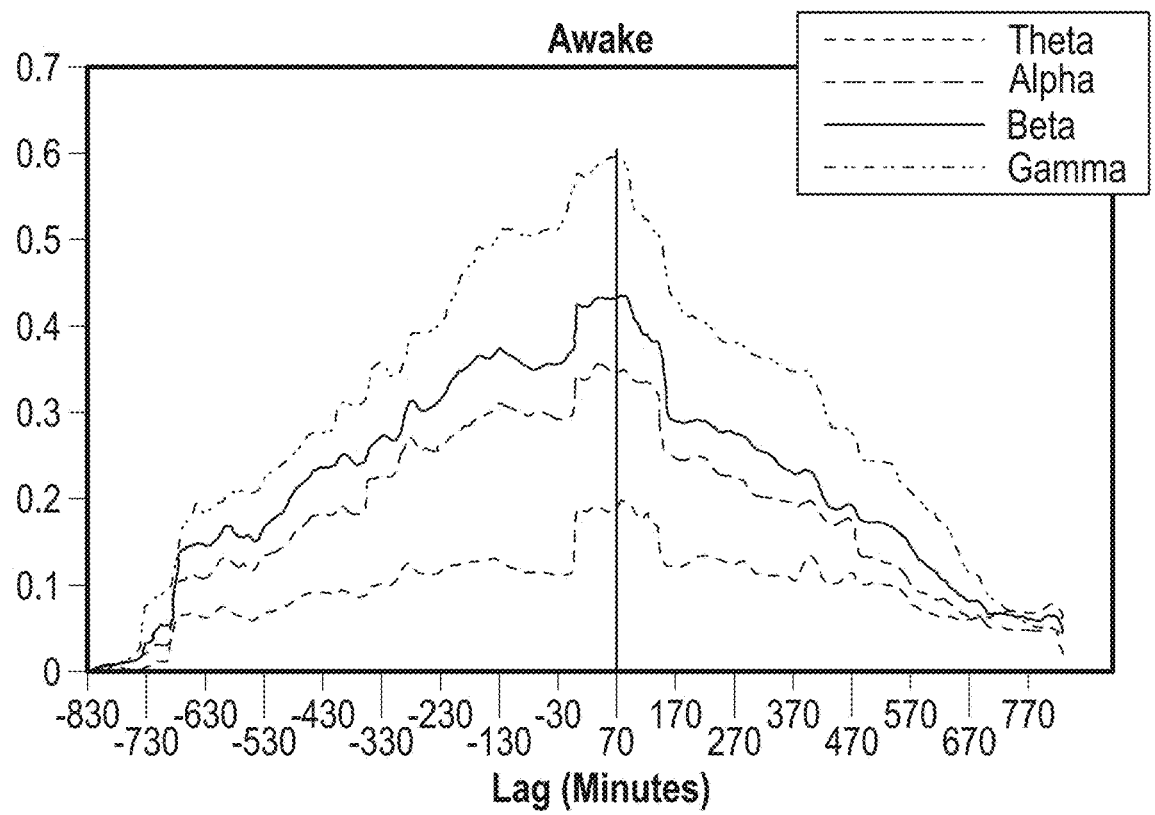

Least absolute shrinkage and selection operator (LASSO) was performed, the results plotted and saved (plots shown in FIGS. 16A, 16B, 17A, and 17B, for awake and sleep, respectively). Predicted blood glucose values were extracted from the model training on single-channel EEG and CGM values, from a single lag. FIG. 16A shows all power estimates in 1:50 Hz intervals, while FIG. 16B is an average of those into four frequency bands (alpha, theta, beta, and gamma).

Figure 20:
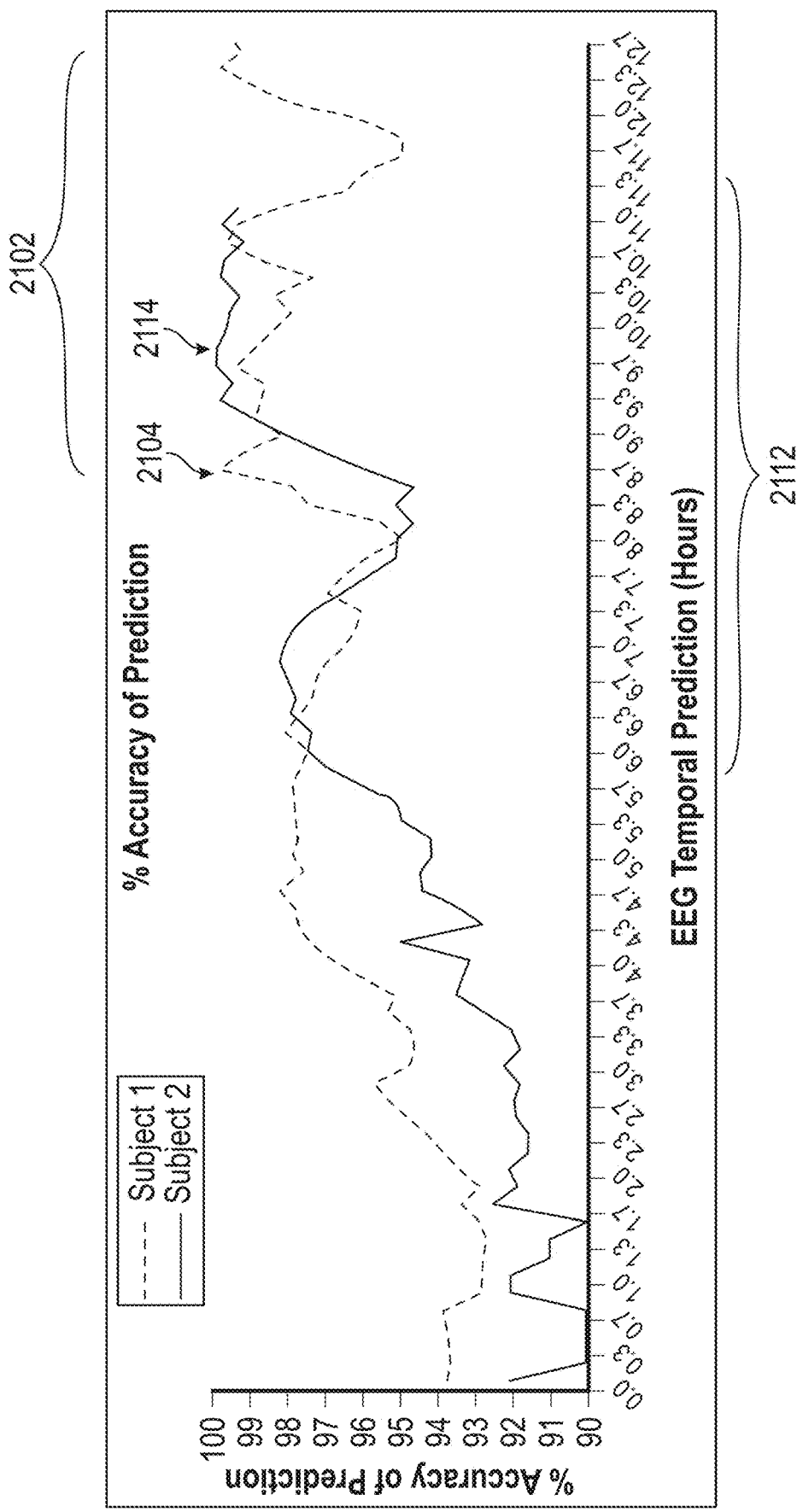

FIG. 20 plots % accuracy of predicting blood glucose levels vs EEG temporal prediction (hours) from the two subjects in this example on the trained model. As can be appreciated, the accuracy of predicting glucose values on the time scale up to 12.7 hours was 90% or greater from zero to 12.7 hours in advance, demonstrating significant accuracy. From this plot, and as part of a process of developing/creating/training a glucose state predicting algorithm/model, an exemplary approach may include selecting or determining that one or more particular times or one or more particular time ranges with higher correlations is preferred as more accurate. For example only, an approach may include selecting or determining that during time period 2102, as labeled, the accuracy is at least 94%, and that time range of about 8.3 hours to 12.7 in advance, or one or more epochs within that range, is a preferred time range to input sensed brain data into the model and predict one or more glucose values for that particular subject. Temporal time lags may change for each subject over the course of the subject's daily routine, such as changing from day to day. Optional systems and methods herein may thus benefit from periodically sensing not just brain activity data but also estimate blood glucose values with a glucose monitor, and adjust the temporal lag as may be desired or needed. Time range 2112 is a mere example of a temporal lag range for subject 2 that might be selected or determined due to the relatively high % accuracy of prediction. In some applications, a specific time point may be selected, such as time point 2104 or 2114, as a temporal lag for the relative subjects, due to a relatively high % accuracy of prediction. The temporal time lags in this context, if they are discussed in the context of a personalized lag with relatively high accuracy for that particular subject, are referred to herein as a personal time lag or other similar term.

Additionally, any of the Apps herein may be adapted to provide the functionality to allow the subject or care-team to select a time or time range in the future for which they would like predictions. For example only, any of the Apps herein ("Apps" described below) may be configured to visually present on a display or screen of the device a selectable user input to choose or select a time for which they would like predictions. For example only, a subject may prefer predictions 2-15 minutes in advance (for more near-term predictions), or, for example, 1 hour in advance, or 30 minutes in advance, for example. Any of the Apps herein can be configured to operate and predict with the selected or chosen time period in advance, and make glucose state predictions that are predicting that subject's glucose levels that time in the future (relative to when the brain activity was sensed).

Training methods herein may utilize one or more features of the sensed brain activity signals (including one or more patient specific features that may lead to greater accuracy for the subject) on glucose states (however sensed/measured), and once trained, the model is adapted to receive subsequently sensed brain activity signals and predict glucose states (e.g., values), wherein the trained model may be specifically trained on the one or more features of the sensed brain activity signals. That is, the trained models herein (which may be stored on any of the subject devices herein, such as part of any of the Apps herein) may beneficially not need to receive or utilize all of the sensed brain activity signals. For example, only, trained models or other algorithms may utilize or receive a subset of the single-channel sensed brain activity signals that have a more significant correlation with glucose values and more accurately predict glucose values, and which may be a more significant correlation between power of one or more bands and glucose values, described above.

Example 1 as described above illustrates that at least a portion of single-channel EEG, from a behind-the-ear location on the skin of a subject, is predictive of blood glucose values, and thus can be used to predict glucose values based on single channel EEG. It also showed that there may be, at least following the processes above in Example 1, some patient-to-patient variability in the % accuracy of prediction, such as when single channel signals may be most predictive. In fact, it may optionally be desirable or even necessary to train prediction methods on data from the intended subject for a personalized prediction App, which is referred to herein as personal or personalized prediction. That is, each subject may have a personalized App that is trained to process EEG data in a way that will be the most predictive for that individual, which may also be considered to be an individual calibration step or process prior to predictive use of the system. Additionally, a subject may benefit from periodically recalibrating their App to ensure it continues to process brain signals in a way that is most predictive for that subject. Personalized temporal lag, as described herein, is a mere example of a patient feature in or related to single channel, non-invasively sensed, EEG signals that can be used in the prediction methods herein.

Features of brain activity data upon which the models may be trained may be personalized to an individual feature, or they may be features that can be utilized across larger populations of people, or even all subjects using a predictive method.

An additional example of a feature of brain activity data is a subset of all frequency bands between 0 Hz and 50 Hz in the prediction method. That is, the prediction methods herein may optionally predict glucose state using only a subset of frequency bands between 0-50 Hz. The subset may include one or more well-described frequency bands (one or more of delta, theta, alpha, beta, and gamma (or a portion of gamma from 32-50 Hz), one or more frequency ranges generally, even if the range spans more than one well-described band, or one or more discrete frequencies. A subset, as that term is used herein, may have a more significant correlation with glucose values and/or the processing of which can lead to greater accuracy of prediction. For example, Example 1 performed above indicated that higher frequencies within the 0-50 hz range, such as within the beta and/or gamma bands, may be more correlated to future blood glucose levels from 18 minutes to up to 13 hours in advance. Processing only a subset, such as one or two bands (or one or two frequency ranges, or certain frequencies) may beneficially require less power during processing, which may be performed in a wearable sensor or in an App stored on a subject device, for example. Similar to a personal temporal lag (where predictions are for a particular time in the future), it may optionally be beneficial or necessary to determine for each subject which frequency bands or frequency ranges are correlated with higher accuracy for glucose state prediction, or which have a more significant correlation with glucose states, either real-time or future predictions. It is understood that there may be more than one feature of brain signal data that may be personalized to a particular subject, such as a particular temporal lag (which may be reset over time), or a particular frequency range of EEG data to be processed. In some embodiments, correlation weight factors may be applied to one or more frequencies or frequency ranges. It is of course understood that features, while they may be personalized to a subject, may also apply to larger populations, and may in fact be used by all subjects using predictive methods herein if the accuracy is sufficient due to a sufficient correlation.

Figure 17A:
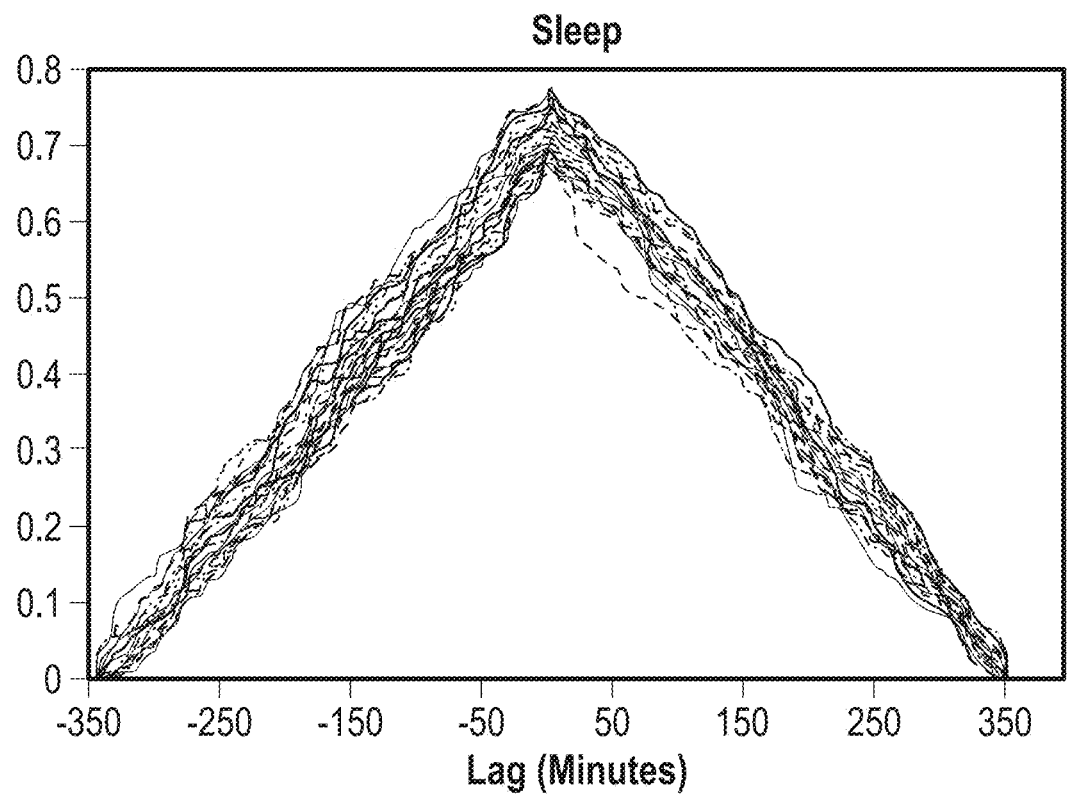
Figure 17B:
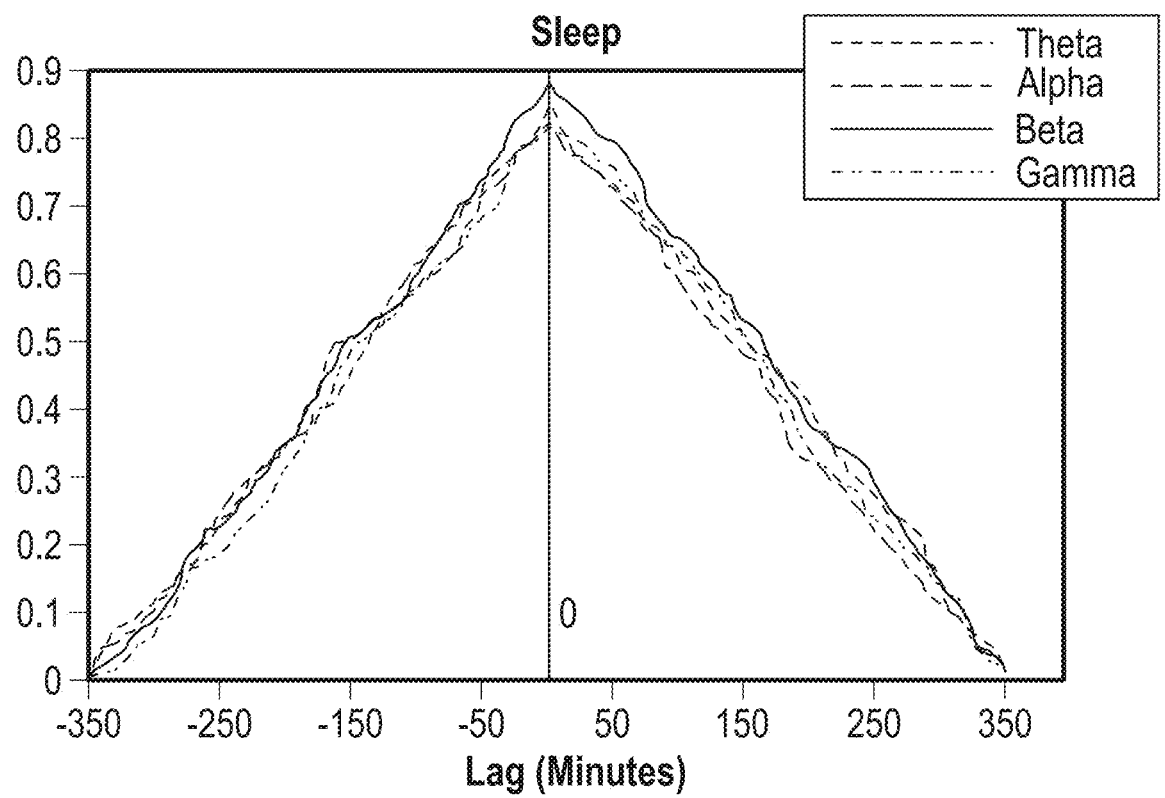
Figure 18A:
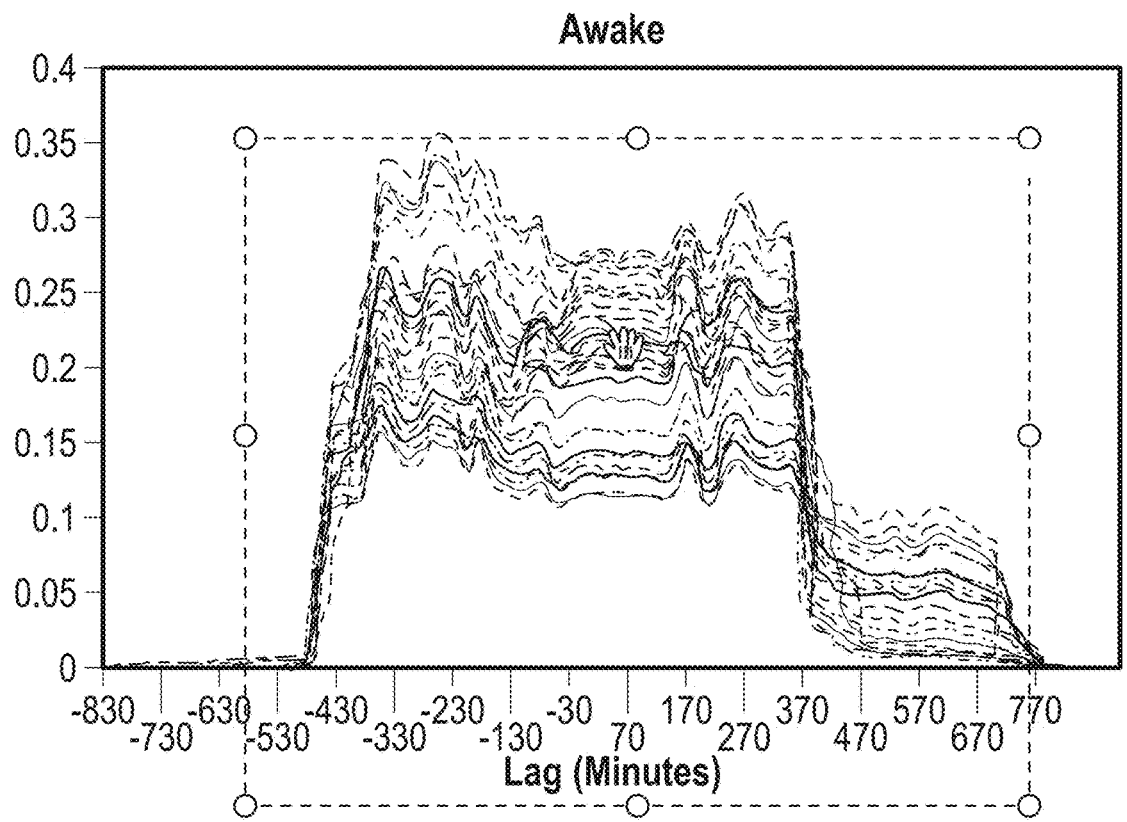
Figure 18B:
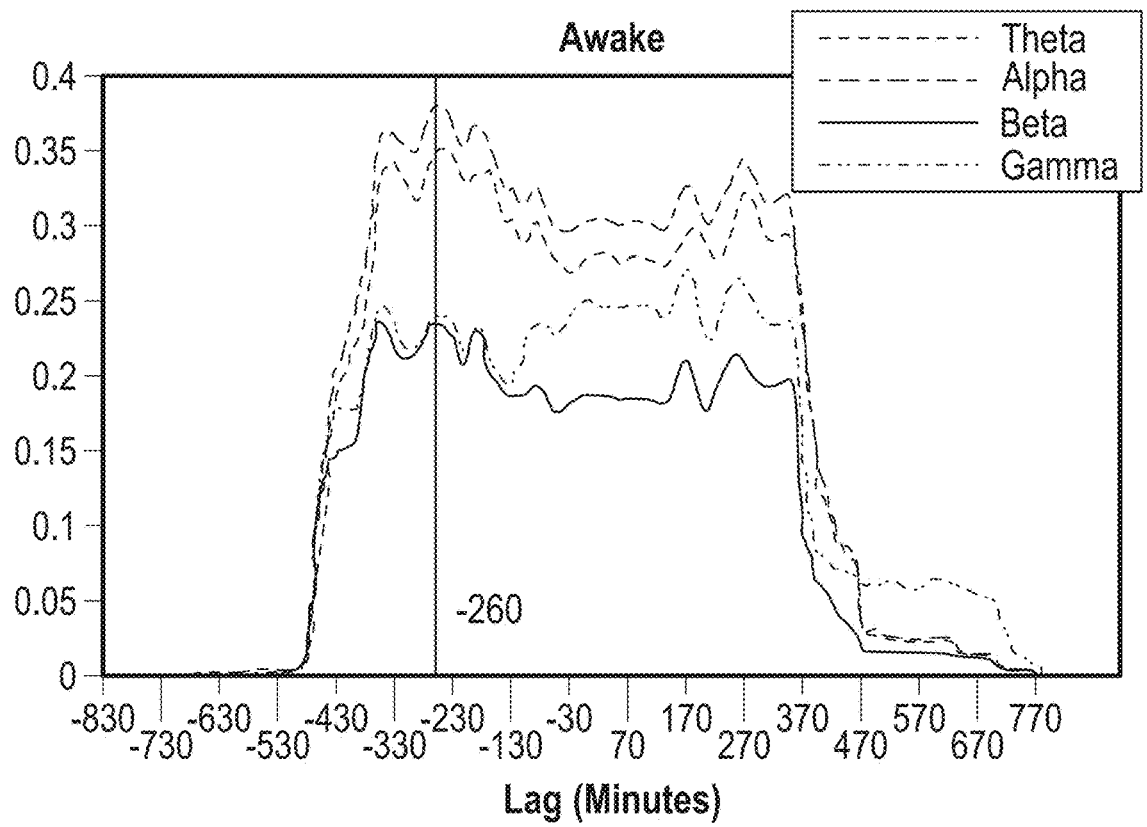
Figure 19A:
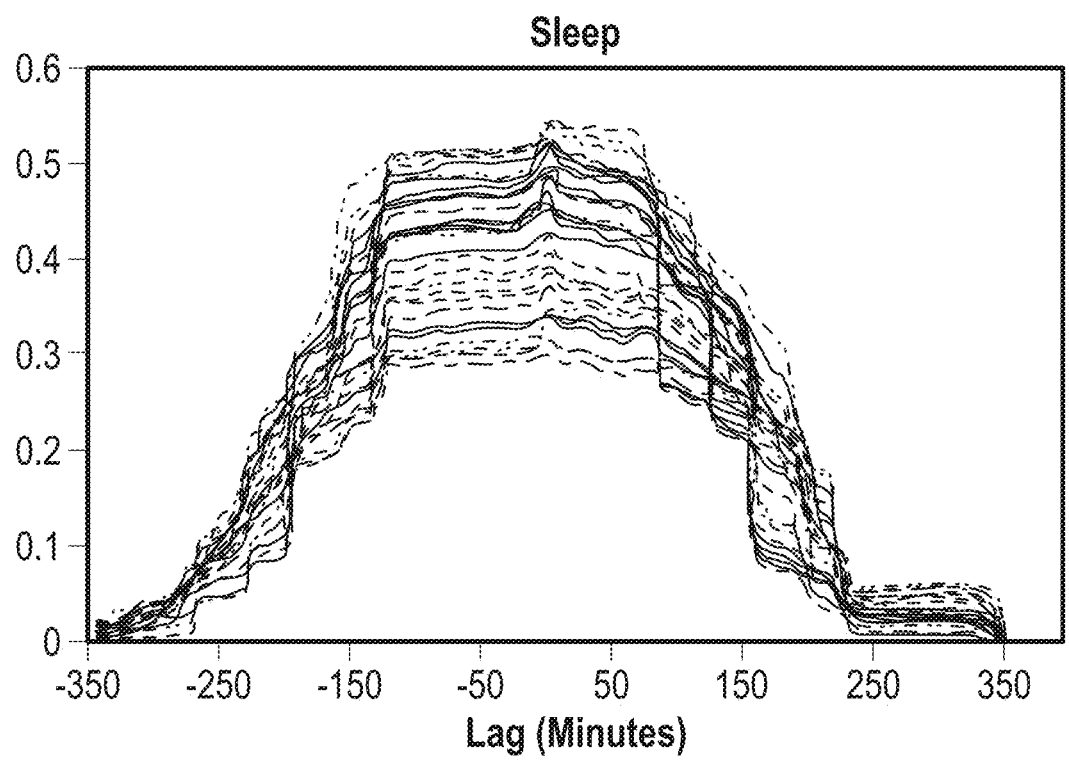
Figure 19B:
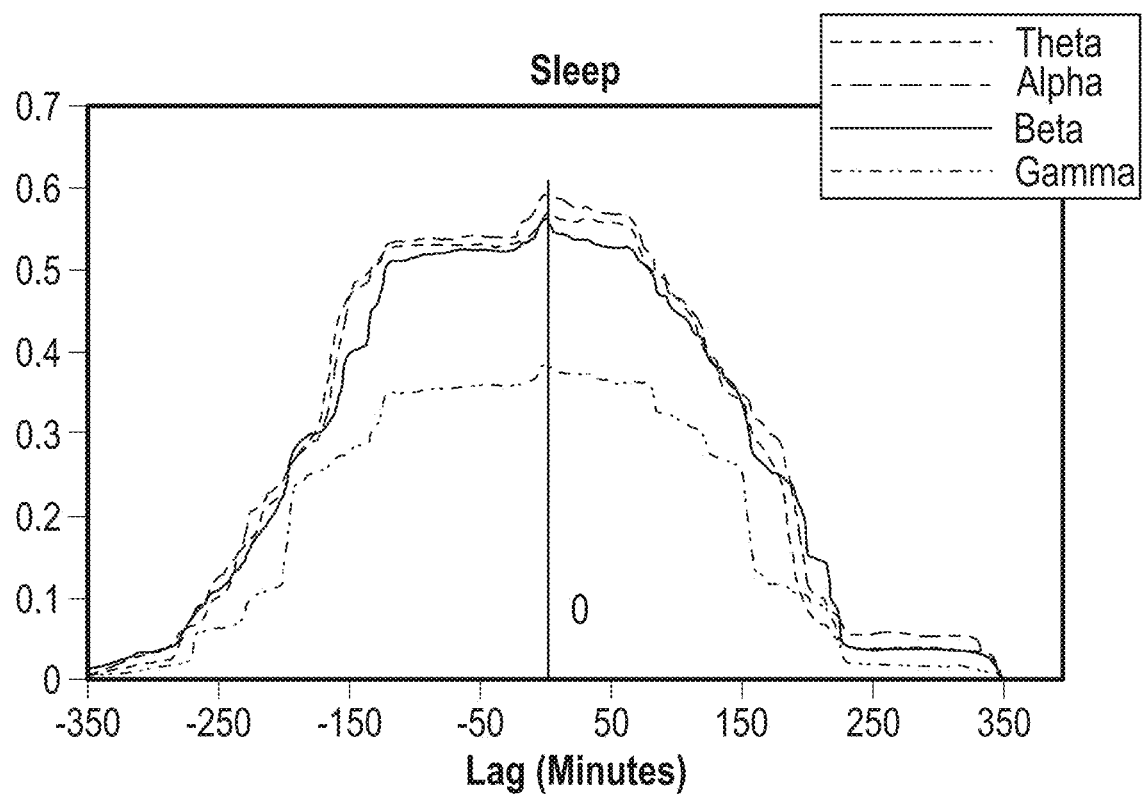

As can be seen in FIGS. 17B and 19B, the extracranially sensed EEG from a single channel was highly correlated with current or real-time blood glucose values sensed using a CGM during sleep time, as indicated by the zero "0" lag. It is of note that following the process above, the extracranially-sensed single channel EEG data was generally not as predictive of future glucose values during sleep time as during awake time. Optionally, methods and systems herein may use a future prediction approach that relies more heavily on brain activity signals sensed during the awake time than during asleep time, which again may provide a benefit of processing less information, thus requiring less power, while obtaining more accurate predictions. Relying more on brain activity signals sensed during the awake time than during the asleep time may optionally comprise applying a weighted factor to awake time signals that is greater than a weighted factor for asleep time signals, for example only. Relying more on brain activity signals sensed during the awake time than during the asleep time may optionally comprise not relying at all on sleep time signals for future glucose state predictions. Any of the methods and systems herein may include this feature of relying more heavily on awake time EEG data for predicting future glucose levels.

Based on the observed high correlation discovered between the single channel extracranially-sensed brain activity data from a behind-the-ear and on-skin location during sleep and blood glucose levels sensed using a CGM, any of the methods and systems herein may further comprise using single channel extracranially-sensed brain activity data during sleep to one or more of predict real-time glucose levels or near-term (e.g., 1-15 minutes in advance) future glucose levels, or even to calibrate a glucose monitor worn by the subject. In fact, in some uses, single channel brain activity signals sensed optionally from a behind the ear location during sleep may be used solely for calibrating or resetting a glucose monitor, and optionally not for blood glucose prediction. Additionally, brain activity data sensed during sleep and used to predict glucose levels in the near-term future may allow near-term future predictions to be made during sleep time that are more accurate and provide more timely and actionable information than currently available CGMs. This may be highly beneficial to diabetic patients who are at risk of night-time episodes of hypoglycemia, particularly for children. It is generally reported that existing (CGMs) are relatively not as accurate during sleep time, perhaps because their readings follow or lag the actual, real-time levels (if the monitor's readings peak or fall too late compared to actual current blood glucose levels). This makes it more difficult for patients to timely recognize the potential hypoglycemic events that are not uncommon in diabetes, because they are asleep. Some subjects preempt this and set their monitor sensitivities during sleep time within a narrower range than the ranges during their wake time, which can cause more frequent alerts and wake them up more during the sleep time, the disturbances from which are known to be suboptimal from a general health perspective. Devices and systems that extracranially sense single channel brain activity signals during sleep can use the sleep time brain data (with or without the sensed glucose levels) to more accurately predict real-time glucose levels, and can even predict the levels in the near-term future to better avoid adverse glucose events.

One aspect of the disclosure is a method of predicting blood glucose levels of a subject while the subject is asleep, comprising: extracranially sensing single channel brain activity signals of a subject while the subject is asleep from a device optionally worn at a behind-the-ear location on the skin; optionally sensing the subject's interstitial glucose (ISG) or blood glucose with any type of glucose monitor while the subject is asleep (e.g., from an optical monitor in a watch); and determining blood glucose levels while the subject is asleep using the extracranially-sensed brain activity signals and optionally the sensed glucose monitor data (e.g., ISG data). Predicting blood glucose levels using at least the extracranially-sensed brain activity signals may achieve a higher accuracy in detecting real-time blood glucose levels than using existing glucose monitors alone. In some instances, it may not even be necessary to use a blood glucose monitor, and rely on sensed brain activity signals instead (although in these cases, other non-glucose monitor biosignals may also optionally be used, such as heart rate, heart rate variability, etc.). Due to the observed high correlation between brain data and sleep-time levels, the glucose levels can even be predicted in the near-term future at sleep, providing technological improvement that could benefit many people.

Figure 21B:
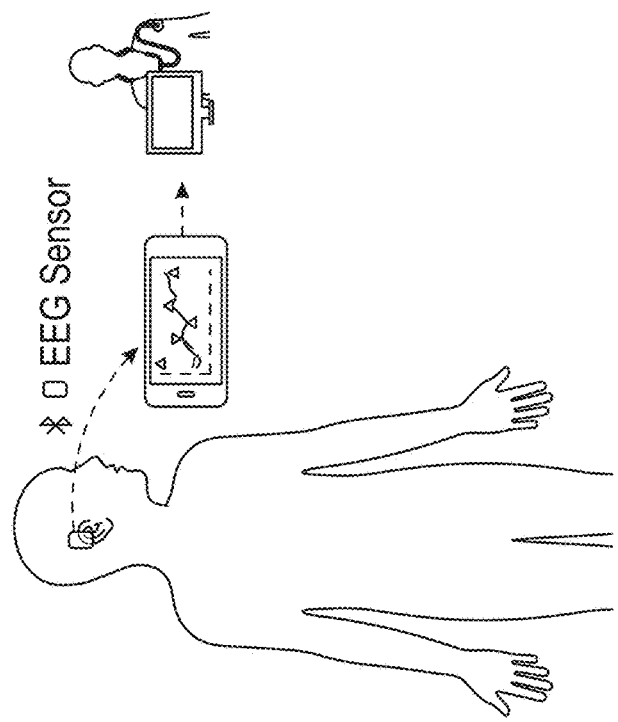
FIGS. 21A and 21B illustrate exemplary systems herein, online optional online portion or care-team device.
Figure 21A:
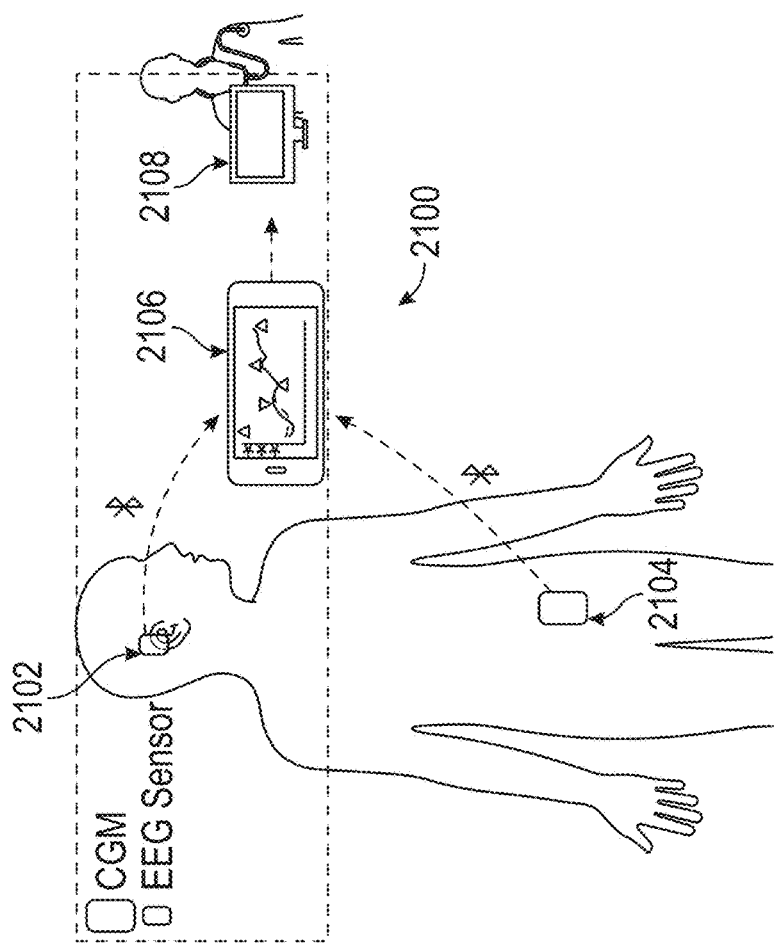

FIG. 21A is an additional merely exemplary glucose prediction system (GPS), optionally continuously sensing (CGPS) that can be adapted and configured for training models and/or predicting blood states. System 2100 includes optional portal device 2108 accessible by a care team member, such as a physician. The GPS may be adapted to predict blood glucose values by itself (e.g., without input from other devices like CGM 2104), but optionally it may be adapted to also predict using or based on one or more inputs from one or more devices (e.g., a CGM 2104 as shown, or other devices that are Bluetooth enabled), which may optionally communicate with the GPS via Bluetooth, as shown. System 2100 includes a wearable sensor 2102 (optionally a second on the other side of the head behind the other ear) and subject device 2106, features of which are described elsewhere herein. It is understood that the optional CGM 2104 shown in FIG. 21A may be replaced with a different type of glucose monitor or sensor, such as an invasive monitor (e.g., implanted in an arm or abdomen) or a non-invasive monitor such as an optical monitor (e.g., integrated into a watch). FIG. 21B illustrates the system 2100 in FIG. 21A, but without the optional glucose monitor. All reference numbers and descriptions from FIG. 21A apply to FIG. 21B.

Example 2

Figure 22B:
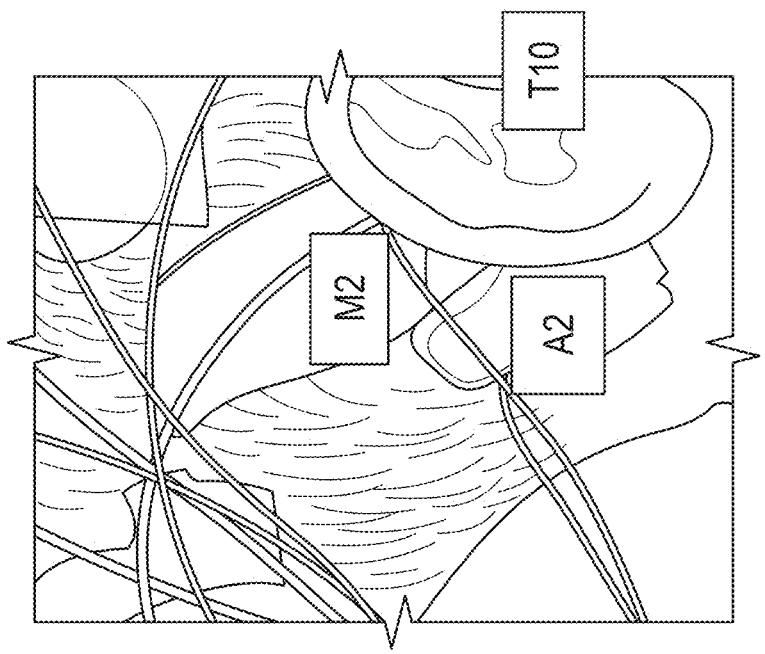
FIG. 22B illustrates the location of additional electrodes A2, M2 (and similarly A1, and M1), all of which are in behind the ear location, in Example 2 herein.

A second herein example used a similar process to Example 1, but additionally utilized more EEG data from a typical EEG setup. In the second example, both glucose data and EEG data were contemporaneously sensed/monitored from a subject for at least 2 days. The subject was wearing an existing continuous glucose monitor (CGM) sensing glucose data, while undergoing a common EEG recording with a setup shown in FIG. 22A, and with the addition of A1 (left) and A2 (right) electrodes in exemplary behind the ear locations, as shown in FIG. 22B. M1 and M2 electrodes are also shown in behind the ear locations.

The preprocessing of data included: 1) only selected "awake" period, and epoched to 10 sec window; 2) aligned the timepoints in CGM and EEG signals; 3) selected 27 EEG channels and common average re-referenced; 4) band-passed [1, 99] and notch-filtered [55 65]; 5. eye blink artifact removed by ICA; and 6) bad trial rejected based on MAD, The steps below illustrate exemplary power extraction and CGM matching: 1) scalp EEG power is extracted using fast fourier transform in FieldTrip toolbox for each 5-s epochs; 2) The trials of power from 1 min before and after to CGM timepoint were selected to align the CGM value; 3) The trials and each frequency band were averaged; 4) linear regression model was used to obtain the correlation between frequency band and the glucose (similar to in Example 1).

Figure 23B:
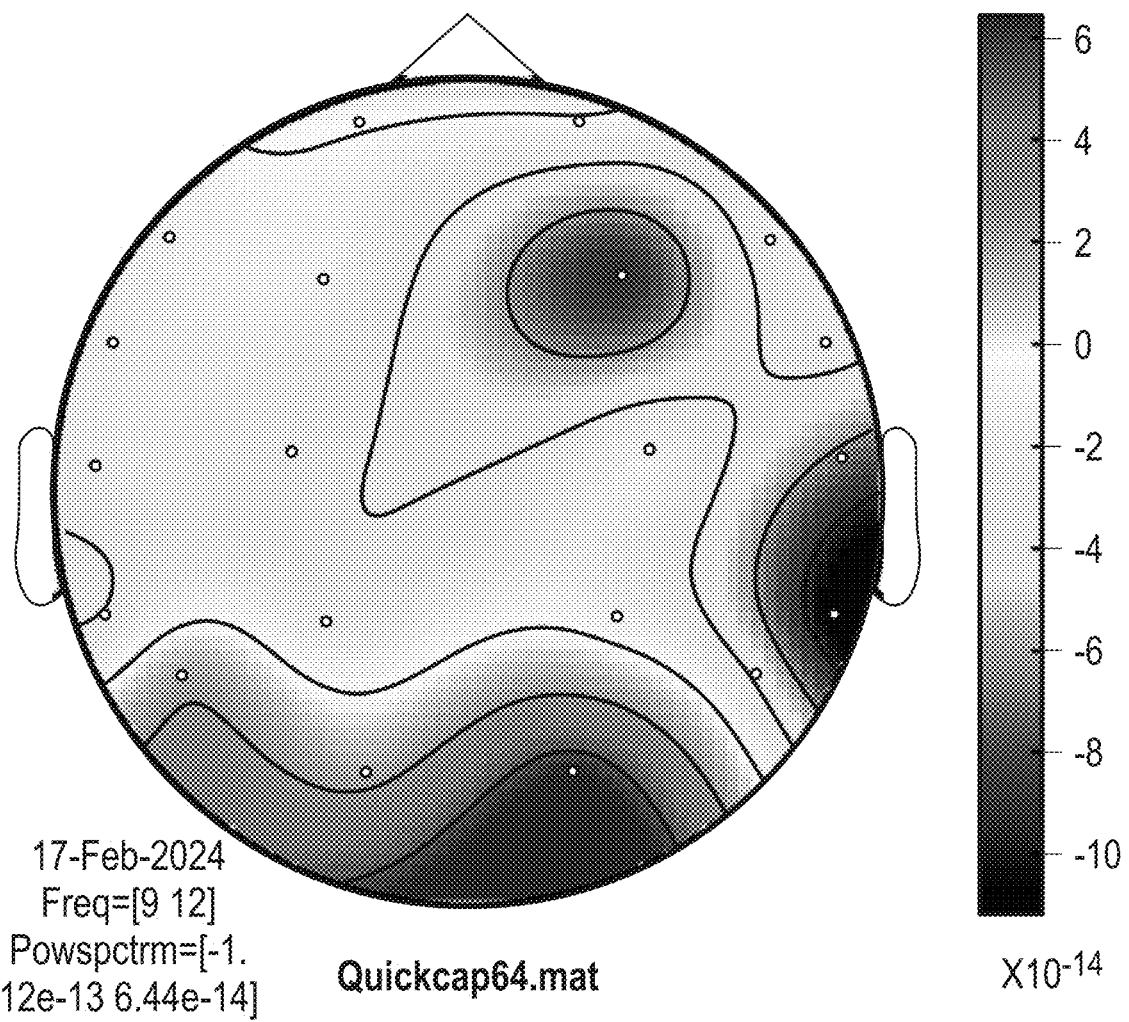
FIG. 23B shows the high negative correlation between glucose and EEG behind the ear and high positive correlation between glucose and EEG occipitally.

FIG. 23A represents a Summary of brain region and bands for which there was a significant correlation between the power and glucose level, and whether it was a positive or negative correlation. Positive correlation refers to higher the power in that particular band corresponding to higher the glucose levels; negative correlation refers to less power being associated with higher glucose values. FIG. 23B shows the high negative correlation between glucose and EEG behind the ear and the high positive correlation between glucose and EEG occipitally.

Figures 24A, 24B:
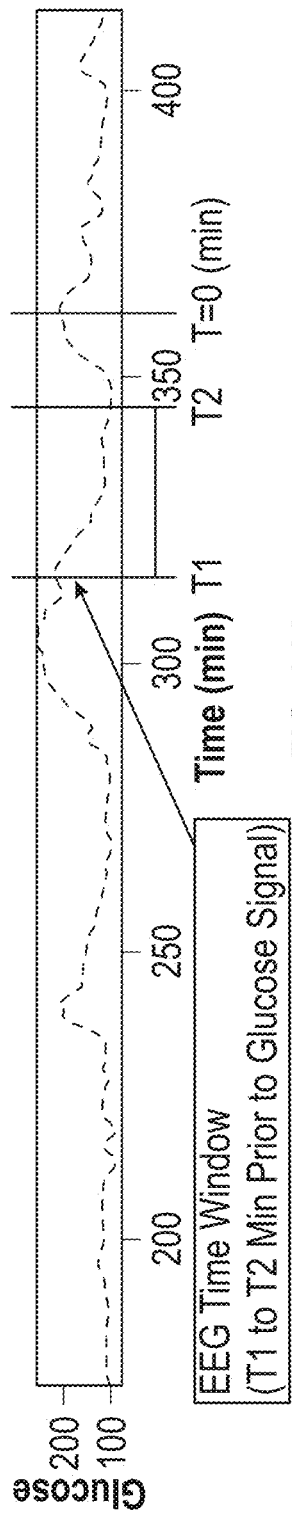
FIGS. 24A and 24B illustrate data from Example 2 in which correlations between brain signals and glucose levels were examined at a plurality of time ranges before the glucose values.

This Example also assessed a variety of time windows prior to the sensed glucose values, as shown in FIGS. 24A and 24B, with the table shown in FIG. 24B providing channels/locations with significant correlation with glucose values in each of the time windows. The significant correlation is related to the table in FIG. 23A for the particular brain region and band of significance.

Figure 22A:
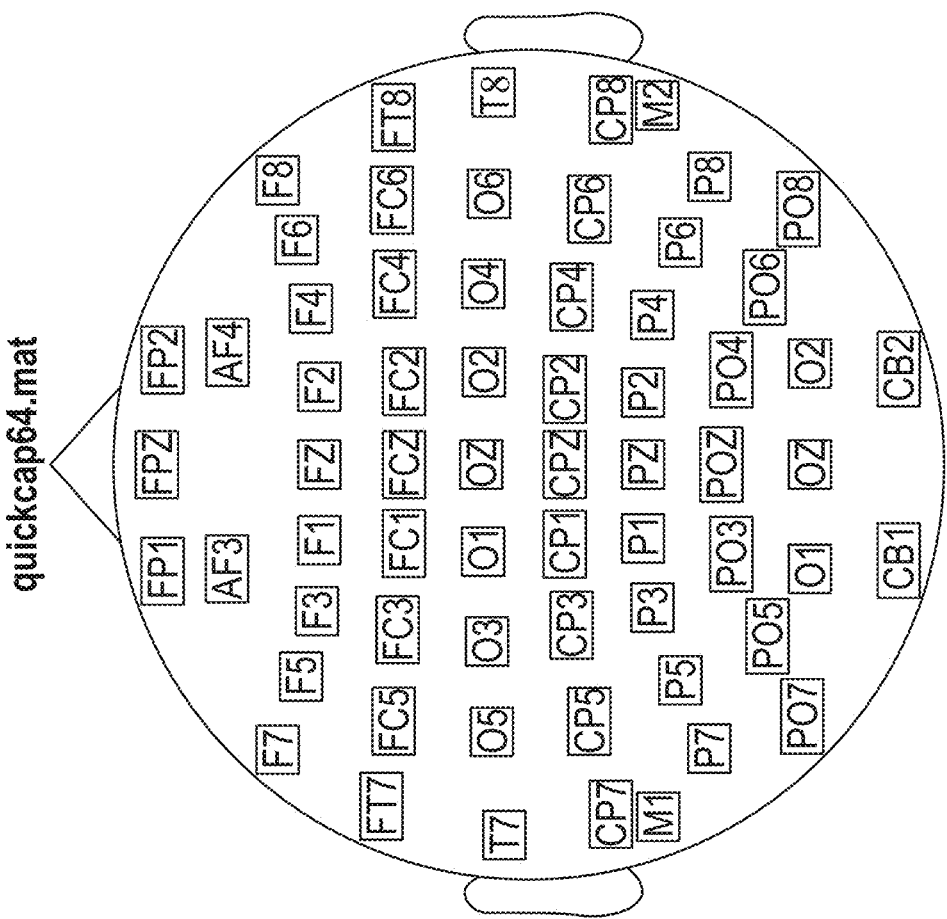
FIG. 22A illustrates a common EEG setup and general head locations and letter-number designation for a plurality of electrodes.

As shown, at least one of occipital 1 and occipital 2 (O1 and O2), the location of which is shown in FIG. 22A, shows significant positive correlation in all time ranges from T1=−13 and T2=−5. Additionally, as shown, M1 and M2 showed significant correlation in at least some of the time ranges from T1=−13 and T2=−5. Additionally, as shown, F7 and F8 showed significant correlation in at least some of the time ranges from T1=−13 and T2=−5.

The data showing significant correlation at these locations and in these bands supports placement of wearable sensors at one or both of M1 and M2 locations (an example of behind the ear) and/or one or both O1 and O2 locations. Additionally, any of the trained models herein may be trained on any of the bands shown in FIG. 23A and/or specifically related to a particular band. For example, any of the models herein may be trained to receive and predict based on only a subset of frequencies from 0-50 Hz, such as at least some frequencies between 0-20 Hz (but not frequencies greater than 20 Hz), such as at least some frequencies between 0-15 Hz, such as at least some frequencies between 0-12 Hz, such as from 5-12 Hz, or from 5-8 Hz, or from 9-12 Hz (alpha). In the table in FIG. 23A, the data from O2 (positive correlation at 5-8 Hz) is an example of a feature that is within a particular band (theta), while the data from M1 and M2 (negative correlation at 9-12 Hz) is an example of a feature within a particular band (alpha). In the table in FIG. 23A, O1 is an example of a brain region with features that span multiple bands, in this case, spanning delta, theta, and alpha. FIGS. 25B, 26B, 27B, and 28B show exemplary plots of raw power and glucose readings for particular electrode locations, at particular frequencies (as shown) and from 11 minutes before to 6 minutes prior to glucose value (T=−11 min and T2=−6 min). CGM levels referenced against the left axis, time is on the bottom axis, and power for that location and frequency range referenced on the right axis. In color, CGM data is blue and power in red. FIGS. 25A, 26A, 27A, and 28A show plots of z-scored power and glucose for select electrode location and frequency range.

One aspect of the disclosure is related to, after predicting a glucose state, outputting instructions to initiate a communication indicative of the predicted glucose state. In some examples, a computing device (optionally a subject device, such as shown in FIGS. 3 and 21) is adapted to output instructions to create one or more visual communications of information related to the predicted glucose states. In some examples, the predicted glucose states (e.g., predicted values) may be visually presented on a display of the device, which may be controlled by an App on the device.

Figure 29:
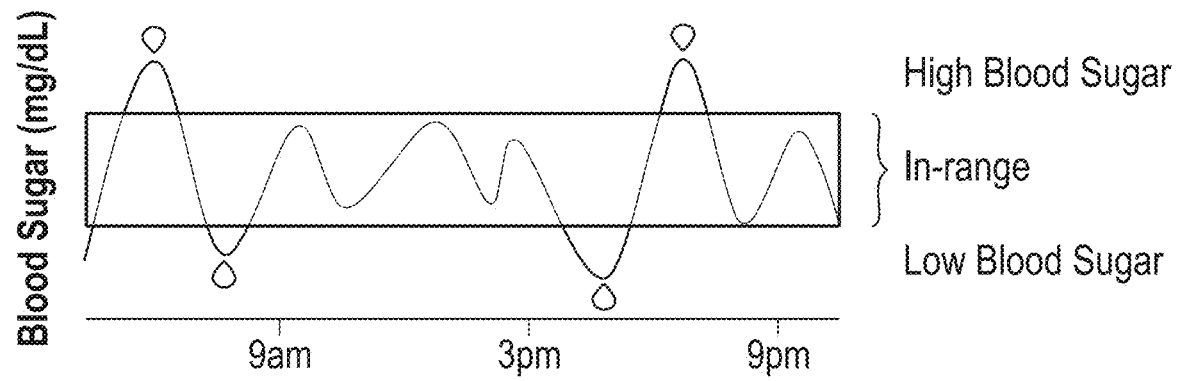
FIG. 29 illustrates an example of a visual representation of glucose state information.

FIG. 29 is a non-limiting example of a visual representation of predicted future blood glucose levels on a display of a device, such as a smartphone or other computing device. For example, an App may comprise a computer executable method that is adapted to cause predicted future blood glucose levels to be displayed, the computer executable method stored in a non-transitory memory, the method comprising: receiving as input extracranially-sensed EEG data or information indicative of extracranially-sensed EEG from a subject; and causing a visual representation of the predicted future blood glucose levels to be displayed on a display of a device. In exemplary FIG. 29, time is on the X-axis and the predicted blood sugar levels on the Y-axis (which may be shown with any unit desired, such as mg/dL). The left side of the X-axis can be considered 3 am, where predicted out or range levels are shown. The software can be adapted to display visual indicators (e.g., the red icons) that can indicate predicted peaks and valleys. The range or any of the ranges herein may be user-adjustable on the display so the user can modify any high or low level for the range that is shown as "in-range." This is one way to provide for personalized glucose management, which is an improvement in technology.

Figure 30:
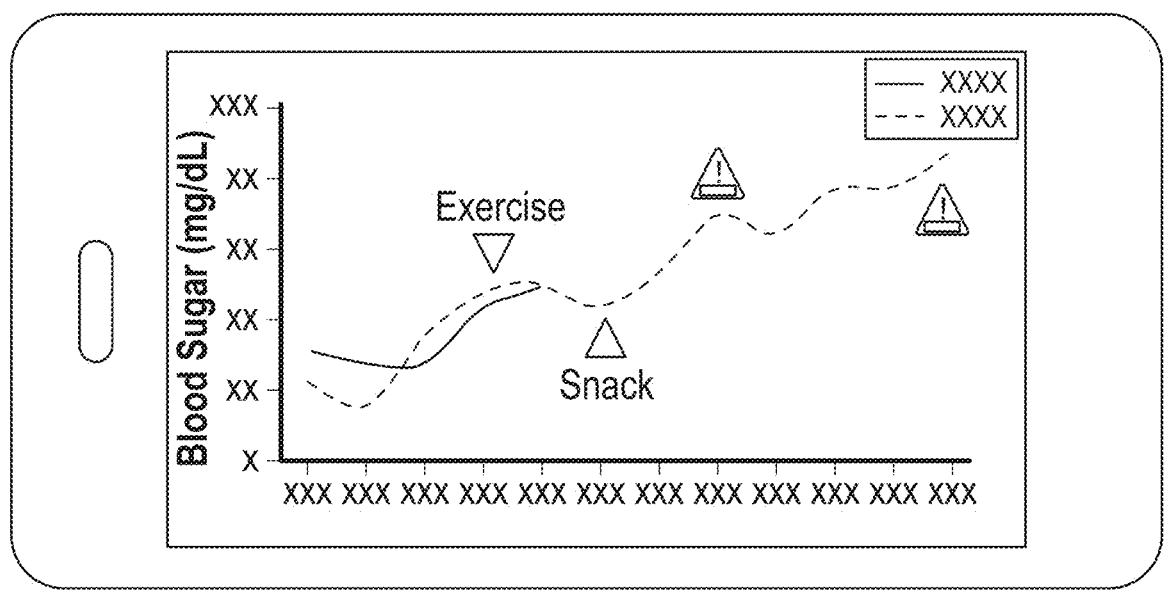
FIG. 30 illustrates an example of a visual representation of glucose state information on an exemplary device.

FIG. 30 is an illustration of a computing device (e.g., smartphone) with a display, wherein glucose state information is being visually presented on the display. The information communicated in FIG. 30 can be the same or similar to information shown in FIGS. 29 and 31.

Figure 31:
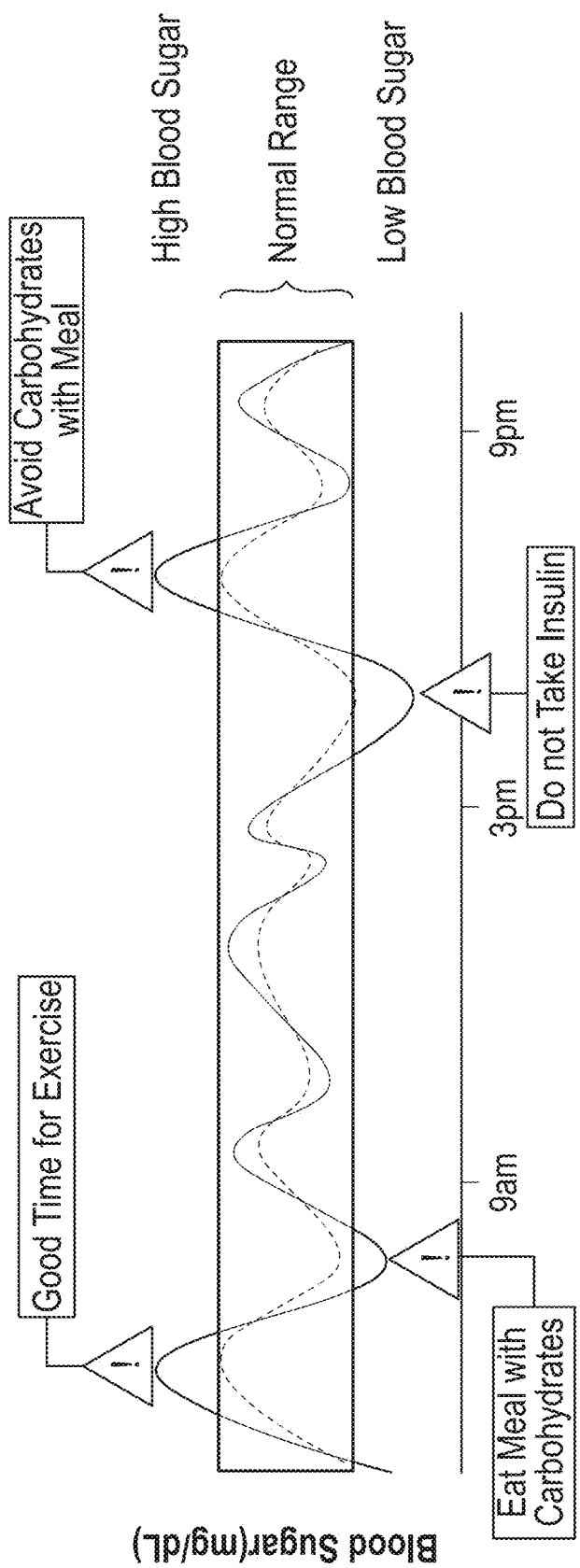
FIG. 31 illustrates an example of a visual representation of glucose state information, including exemplary recommendation.

FIG. 31 is an additional non-limiting example of a visual representation of predicted blood glucose values being displayed on a display of a device, such as a smartphone or other computing device. FIG. 31 also presents a visual representation of suggested actions to be taken and when, which are correlated with high and low trends on the predicted glucose levels. The suggestions shown are merely exemplary, but provide an exemplary of personalized health management provided by the methods and systems herein.

Figure 32:
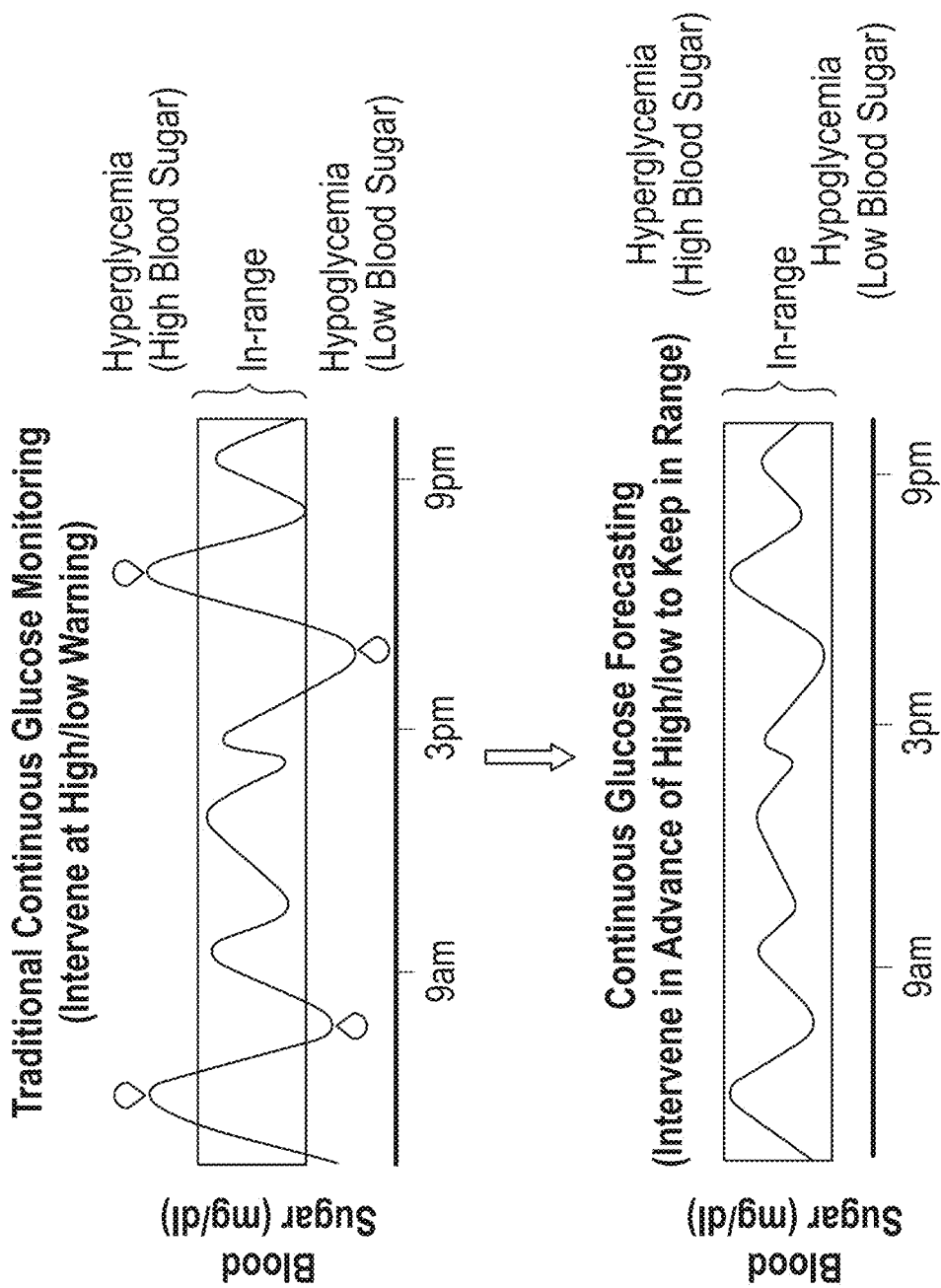
FIG. 32 shows an exemplary comparison between glucose levels with a traditional CGM and with some optional examples herein which are adapted with management steps to main glucose within a certain range.

FIG. 32 is an illustrate example of some examples herein that can predict and maintain blood glucose levels at desired levels. FIG. 32 illustrates exemplary graphs comparing traditional CGMs (top) and optional systems and methods herein that are adapted to predict and maintain blood glucose levels within (or more closely aligned with) a target range (bottom). It is noted that systems and methods herein do not need to include a management aspect, and may provide significant benefits by providing health information (e.g., predicted glucose state).

One aspect of this disclosure is related to methods and systems that allow a subject to select or choose (optionally via an App interface) a period of time during which they wish to receive predictions and/or other information alerts such as alerts. For example only, a subject may only wish to receive predictions during sleep, or only near the time and including the time they will consume a meal. The App may similarly be configured to select when to process brain signals and when not to process brain signals. In the example of selecting sleep-time as a time for the prediction process to occur, the subject may simply wish for the system to predict for more near-term events, such as hypoglycemia. In the example of only predicting near meal-time and shortly thereafter, the subject may want information about glucose levels related to the meal, for example. The Apps herein may thus include an input feature that allows the subject to select from one of a predefined time periods during the 24-hour cycle (e.g., from 9 am-12 pm) for prediction to occur, or a user selectable feature where the subject can disable and reenable the prediction process (e.g., enable when about to sleep, and turn off when awake). Alternatively, the systems herein may be adapted to detect when the subject has fallen sleep based on the sense brain signals, and then begin to process the brain signals and predict predicted glucose states using the prediction model.

One aspect of the disclosure is related to methods and systems that allow a subject to choose the prediction window, or the time in advance they wish to receive prediction information about predicted glucose states (relative to one or both of when the brain data was sensed or relative to the current time). For example, a user may wish to only be informed of relatively near-term future predictions. For example, a subject may wish to select a prediction window of 20 minutes. In this example, the x-axis shown in FIGS. 29-31 may only include a time period of 20 minutes (e.g., every minute demarcated on the x-axis with a dash). For example only, a subject may wish to be informed mostly about sleep glucose swings (e.g., to avoid hypoglycemia), and may only wish to focus on near-term predictions. The Apps herein may include a user input feature that is adapted to allow the user to select or choose the prediction window. Choosing a prediction window may optionally be part of an initial user set-up process, wherein it may be beneficial to train a model based on the desired prediction window. Any of the prediction methods herein may thus be adapted to predict 30 minutes in the future (or any number less than 30), and optionally not more than 30 minutes in the future (or any number less than 30). An exemplary use scenario is during sleep, and a subject may receive alerts up to 30 minutes in advance if they are trending towards or in a hypoglycemic state.

One aspect of predicting glucose states herein is related to predicting prandial blood glucose events, optionally post-prandial. Exemplary post-prandial events include, but are not limited to, post-meal peaks in glucose levels or time until a post-meal peak in glucose levels. An exemplary rationale for systems and methods adapted to predicting postprandial glucose events is that elevated postprandial glucose concentrations may contribute to suboptimal glycemic control. Additionally, postprandial hyperglycemia is one of the earliest abnormalities of glucose homeostasis associated with type 2 diabetes and is markedly exaggerated in diabetic patients with fasting hyperglycemia.

As used herein, the term "meal" includes any consumption or ingestion, and may simply be a snack, a drink, etc., and is understood not to be limited to an amount or type of consumption or ingestion.

After a meal, there is a rise in blood glucose levels. Glucose monitoring data (e.g., from CGMs) has been shown in the literature to be able to identify post-meal glucose peaks. One aspect of this disclosure is a method of training an algorithm or model to predict, using as input extracranially sensed single channel brain activity signals from a subject and glucose values estimated using an existing CGM (but any other type of sensor/monitor may be used to obtain glucose data). A merely exemplary method of training an algorithm may include: obtaining an indicator of consumption by a subject (e.g., an input from a subject that food has been consumed, optionally via an App); obtaining blood glucose measurements from the subject (optionally with a CGM, an implanted glucose monitor; or a noninvasive glucose monitor such as a watch; etc.); and obtaining extracranially sensed brain activity signals from the subject. The method of training can further include temporally identifying on the glucose measurement readings (with glucose values) when consumption has occurred (such as via input from the subject about when food was consumed), and identifying (e.g., visually or automatically identifying) a post-prandial glucose peak subsequent in time to the consumption (e.g., 5 to 90 minutes, for example), such as including the timing post-consumption and/or amplitude of the peak. An algorithm/model can then be trained to identify patterns or other features of the brain activity signals (and optionally other subject measurements, such as heart rate, heart rate variability, and/or others described herein) preceding the glucose peak that are predictive of the subsequent glucose peak. After the algorithm has been trained using the EEG data and monitored glucose data, subsequent brain activity signals can be used as input to the trained model to predict the subject's postprandial glucose peaks (and which optionally may be performed without monitoring glucose levels with a glucose monitor). Any of the aspects and description above related to training machine learning model is fully incorporated by reference into the post-prandial aspect of the disclosure herein.

Figure 33:
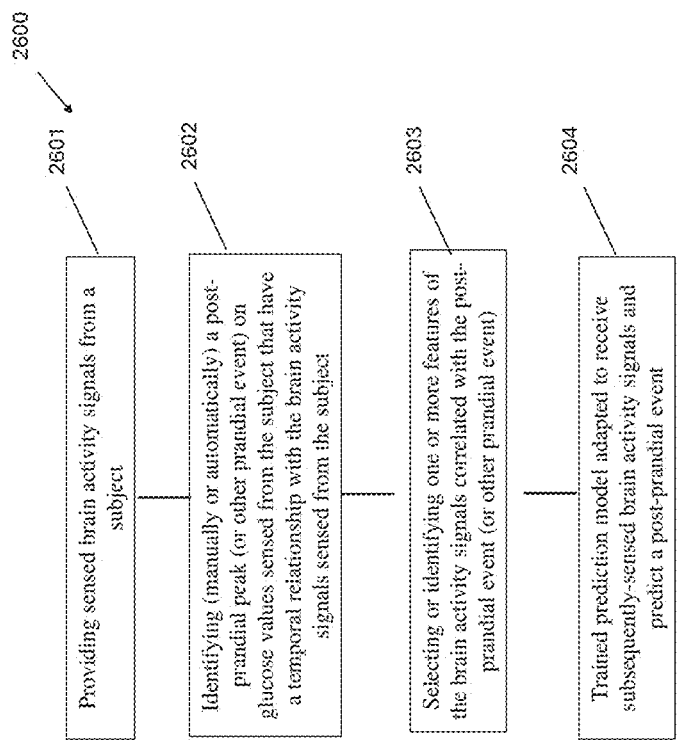
FIG. 33 is an exemplary method of training a glucose state prediction model to predict a prandial event.

FIG. 33 illustrates an exemplary method 2600 of training a model to predict a prandial event, with a post-prandial event as the example. At step 2601, the method includes providing sensed brain activity data or signals from a subject. Step 2602 includes identifying (manually or automatically) a post-prandial peak (or other prandial event) on glucose values sensed from the subject that have a temporal relationship with the brain activity signals sensed from the subject. Step 2603 includes selecting or identifying one or more features of the brain activity signals correlated with the post-prandial event (or other prandial event). At step 2604, once trained, the trained prediction model is adapted to receive subsequently sensed brain activity signals and predict a post-prandial event.

In alternative training methods, it may not be necessary to expressly label or identify an event such as a meal or peak, if recorded glucose data is available. For example, in healthy individuals, a relatively large increase in glucose (for example "large" may be about an increase of 1.5-2 mg/dL/min) may be able to be identified without the manual labelling of a meal.

Subjects may have individualized blood glucose (BG) changes after a meal. For example, one subject may have a post-meal peak 30 minutes after a meal, while a second subject consuming the same meal may have a peak 45 minutes after the meal. Additionally, some subjects may respond with a greater change in glucose levels following meal consumption than others, such as if a first subject does not experience a significant increase in BG while a second subject does in fact experience a significant increase in BG following the same meal. Personalized or individualized knowledge about a post-prandial glucose event (e.g., a BG peak) can provide valuable medical information to the subject. An exemplary but non limiting benefit of an algorithm that is adapted to predict post-prandial BG events such as BG peaks is that a subject can be informed about at least one of the timing or the amplitude of the peak, which may be beneficial to a wide variety of subjects. For example, it may provide information to a subject about when to take insulin and/or what dose of insulin to administer. Additionally, for example, a subject monitoring their overall health may simply want to know when their BG levels may be elevated, such as with a post-meal peak. Additionally, for example, an athlete may benefit from knowing when an elevated or peak BG level is likely to occur, as well as a predicted amplitude of the BG level. Additionally, for example. A subject may wish to avoid certain foods if they know some meals provoke BG levels that are quite elevated. There are many reasons why an individual may benefit from knowing about an elevated BG level, including a peak.

Any of the methods herein, upon predicting a post-prandial peak, can communicate information related to the peak to the subject, such as visually providing a predicted time of peak and/or the predicted glucose value of the peak on a display of the subject device.

One aspect of the disclosure continues to utilize input from the subject about meal consumption as a way to modify and/or improve the EEG BG prediction algorithms herein.

One aspect of the disclosure is the at least partial use or reliance on both of sensed glucose levels and sensed EEG data, the use of which together may, for example, improve the accuracy of algorithms herein. For example only, sensed EEG data may help improve the accuracy of glucose sensors, and/or sensed blood glucose data from glucose sensors may help improve the accuracy of EEG sensors.

Example 3

FIGS. 34-37 illustrate aspects of a merely exemplary data set that is related to and descriptive of the disclosure herein related to post-prandial or post-meal glucose event prediction (e.g., peaks) and training methods related to the same, such as the exemplary training method in FIG. 6. In this exemplary data set, there were three individuals: one prediabetes, one type 1 diabetes, and 1 non-prediabetes (who may otherwise be referred to as healthy). 2-3 days of EEG data and CGM data were obtained from the subjects at the same time. The healthy subject logged all meals during the time, and thus any meal information on any chart is related to the healthy individual.

Figure 34:
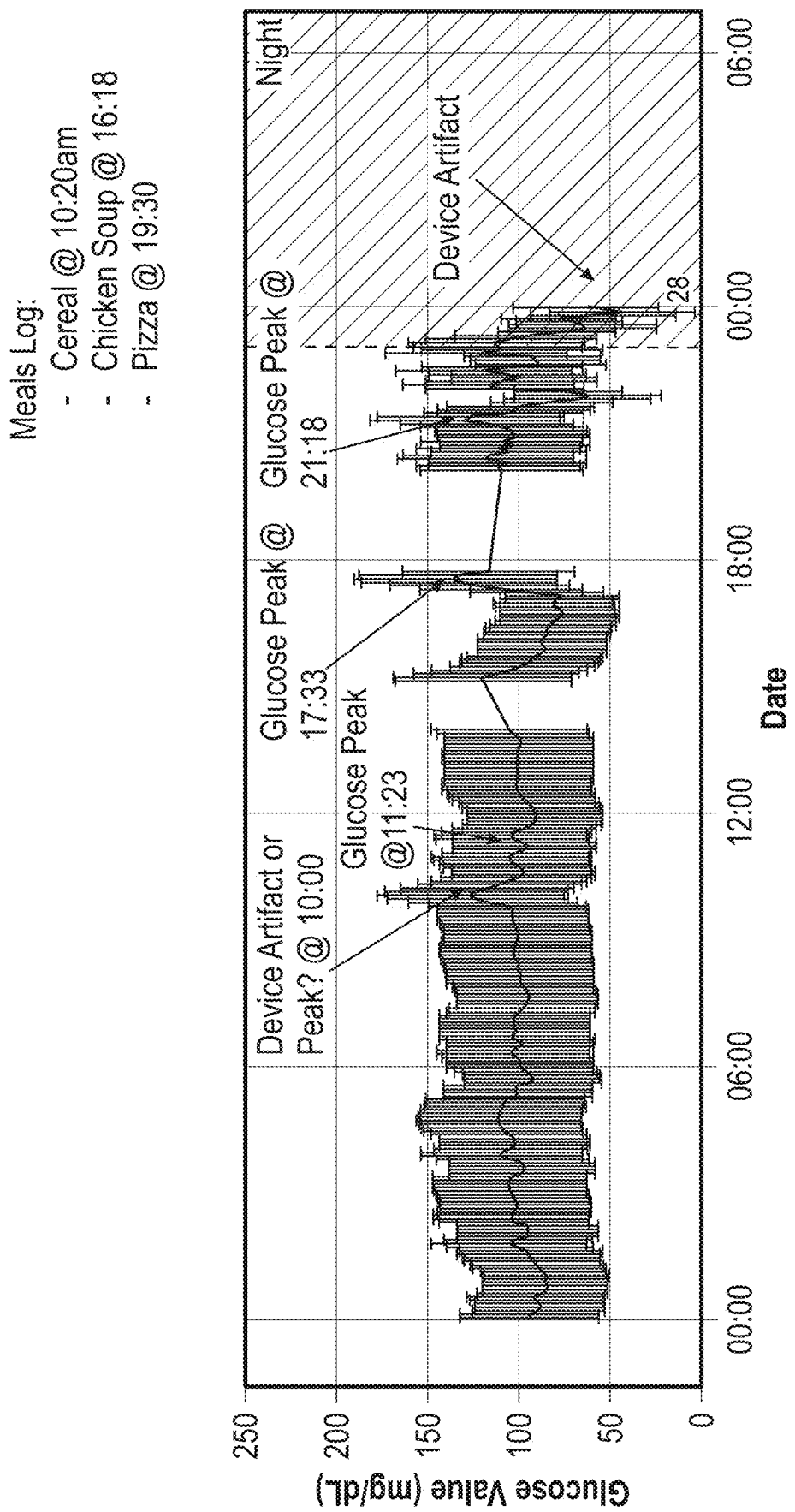
FIGS. 34, 35, 36, 37, 38, 39, and 40 show data from Example 3 herein.

FIG. 34 illustrates blood glucose readings for the healthy subject over a period of time, including time of logged meals (again, the logging of meals may not be necessary). BG was recorded with a CGM. Post-prandial glucose peaks are labelled following three logged meals, as well as suspected CGM artifact, which is known to occur to some extent with CGMs.

Figure 35:
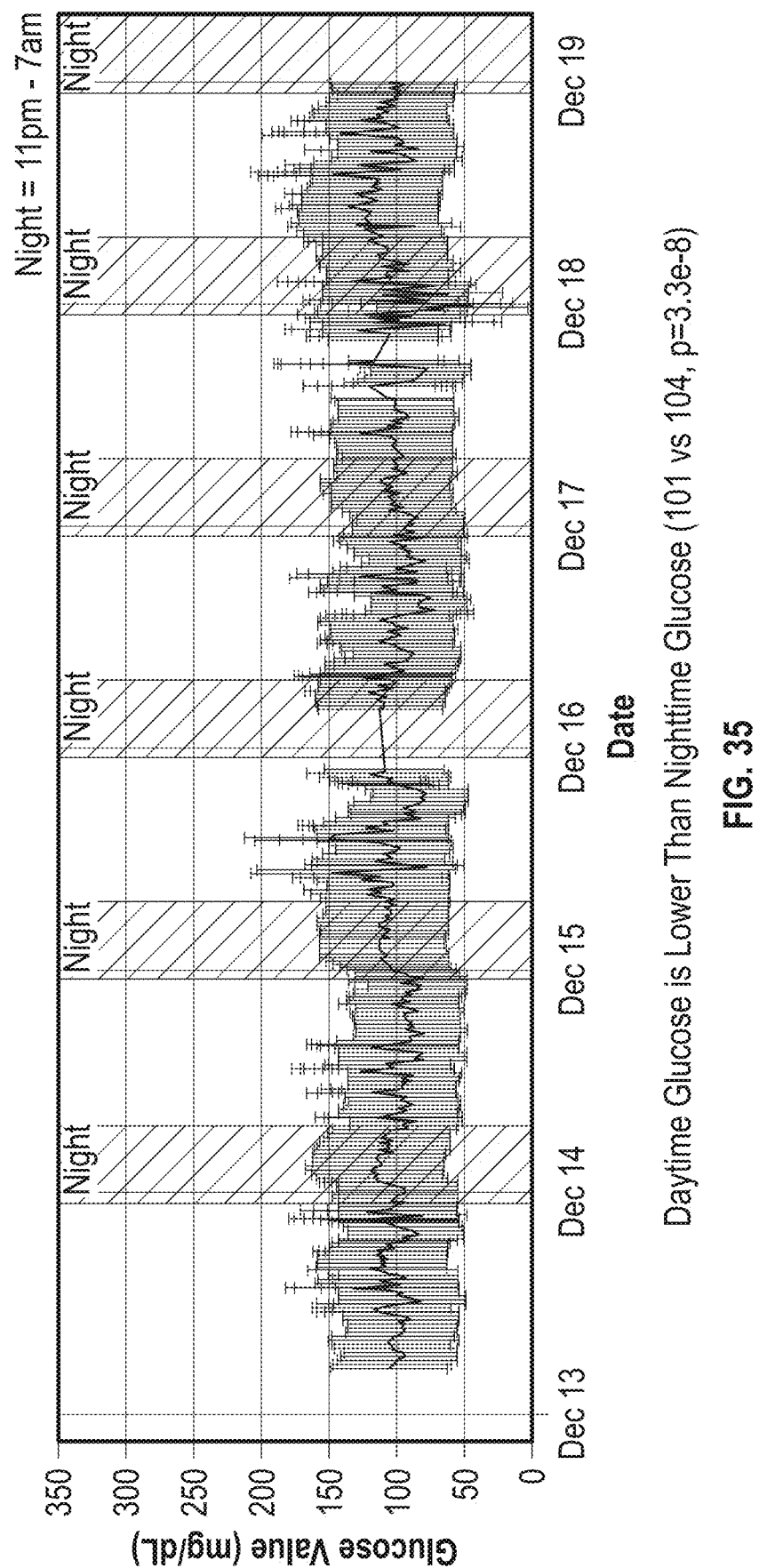
Figure 36:
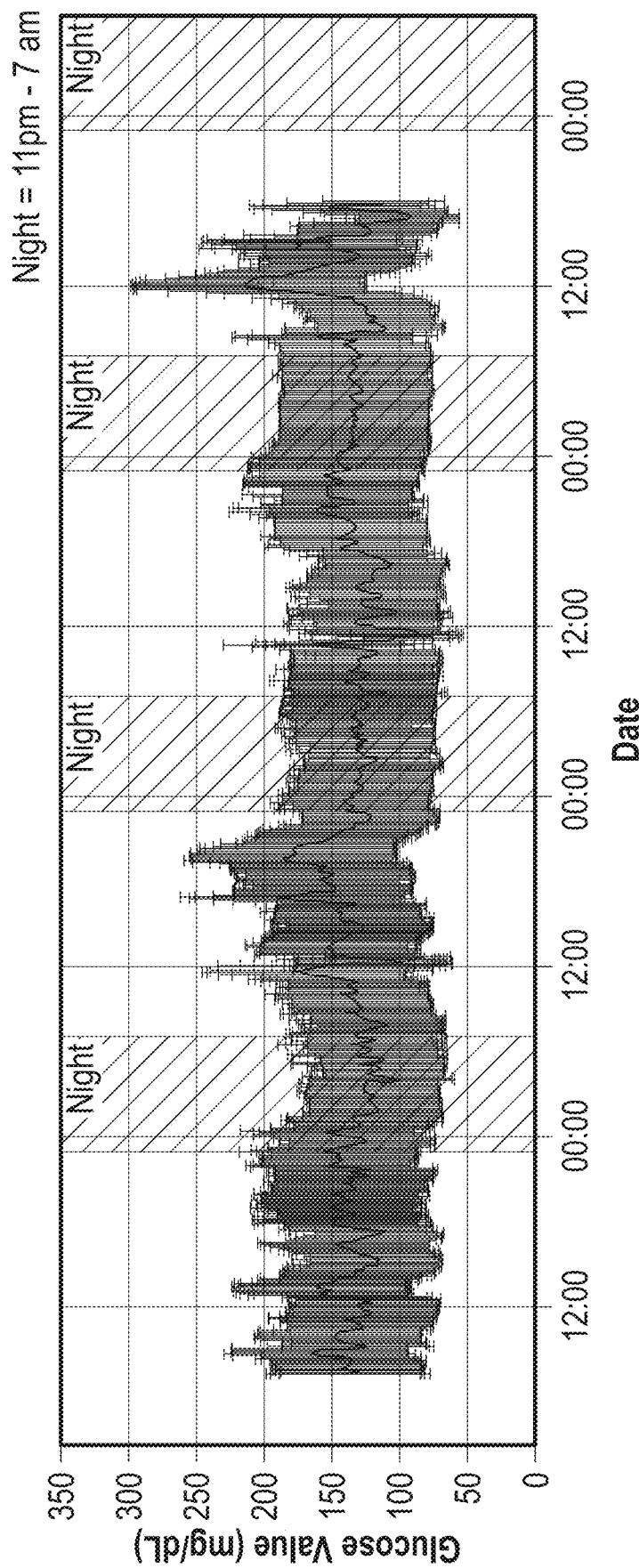
Figure 37:
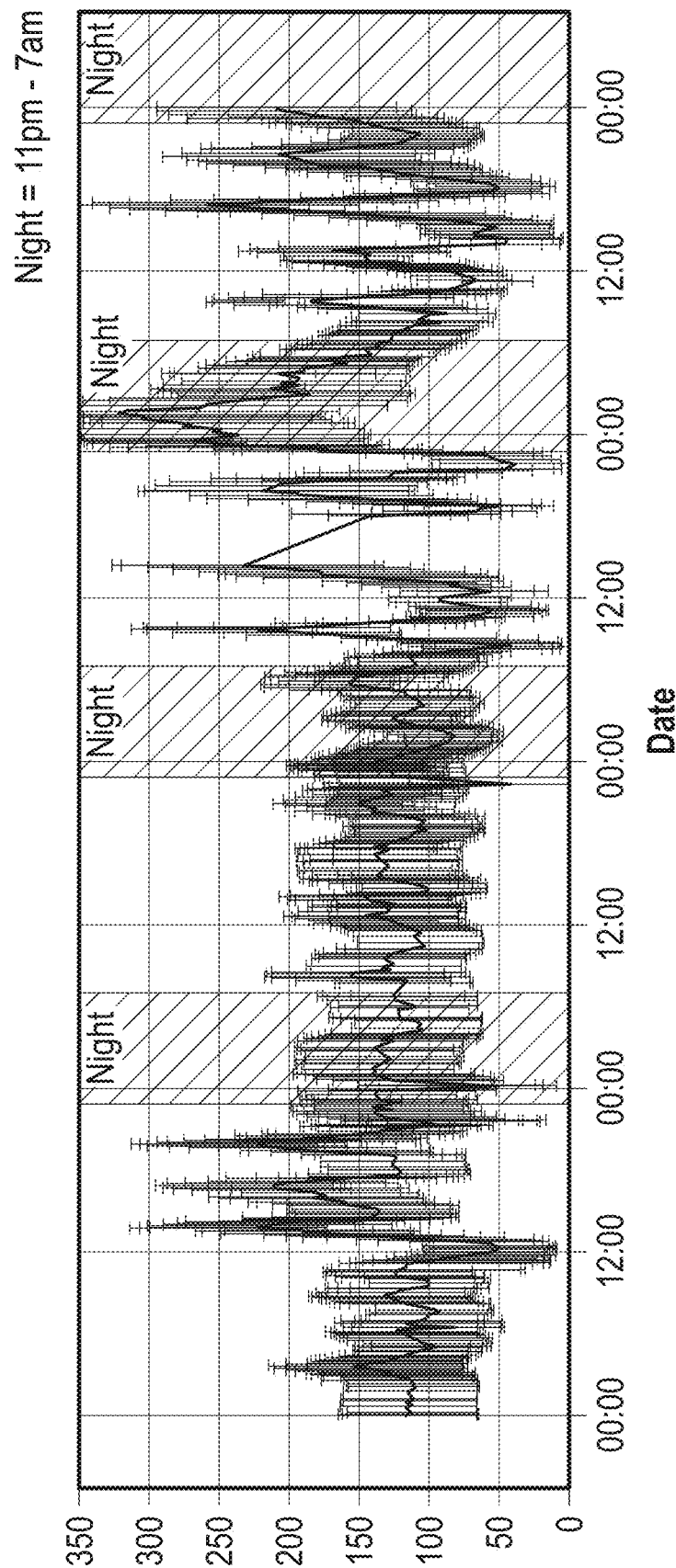

FIG. 35 illustrates healthy individual recorded glucose levels vs time, by date, with day and night hours labeled. FIG. 36 illustrates recorded glucose levels vs time for the prediabetic subject, by date, with day and night hours labeled. FIG. 37 illustrates recorded glucose levels vs time for the Type 1 diabetic subject, by date, with day and night hours labeled.

Figure 38:
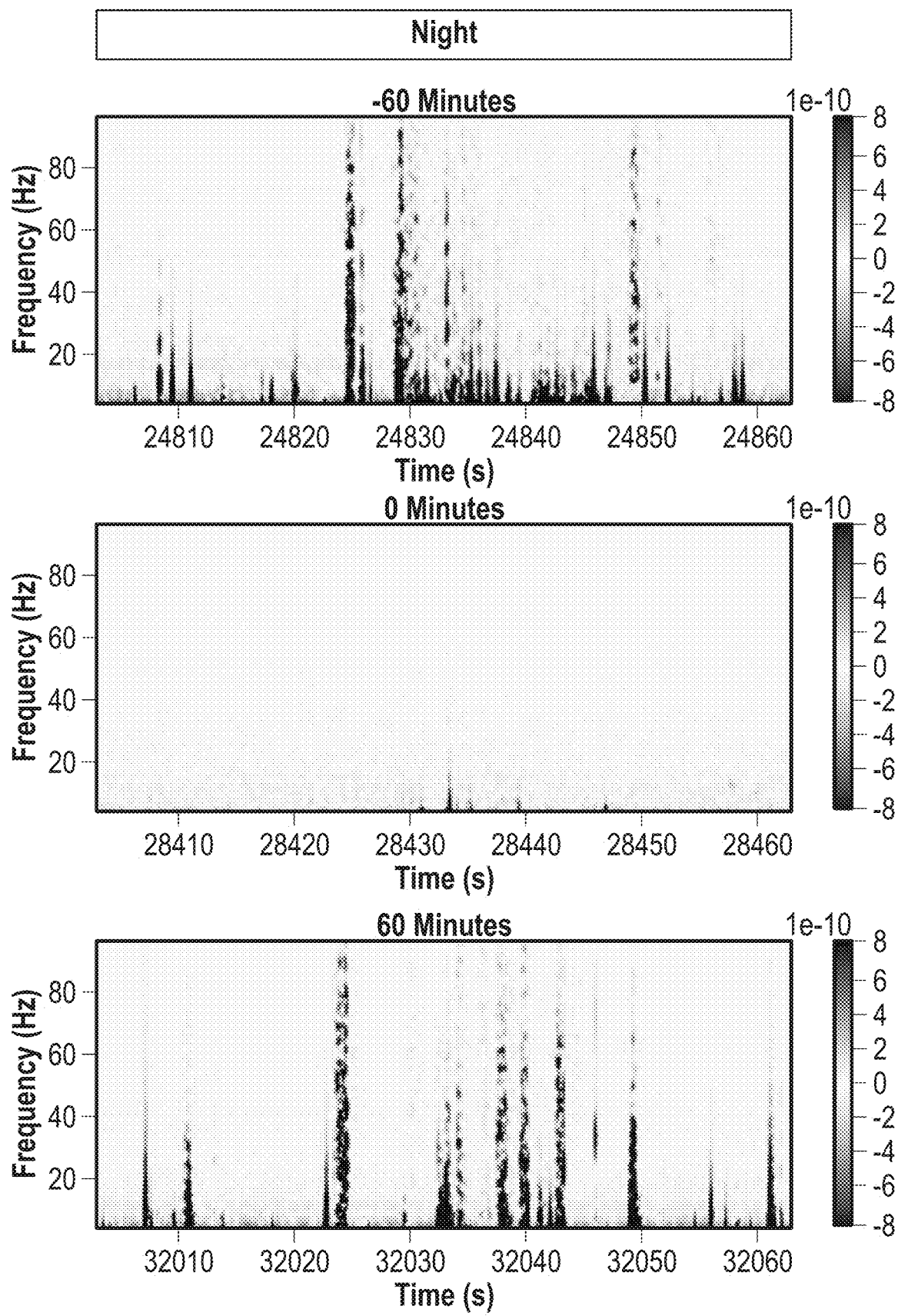
Figure 38:
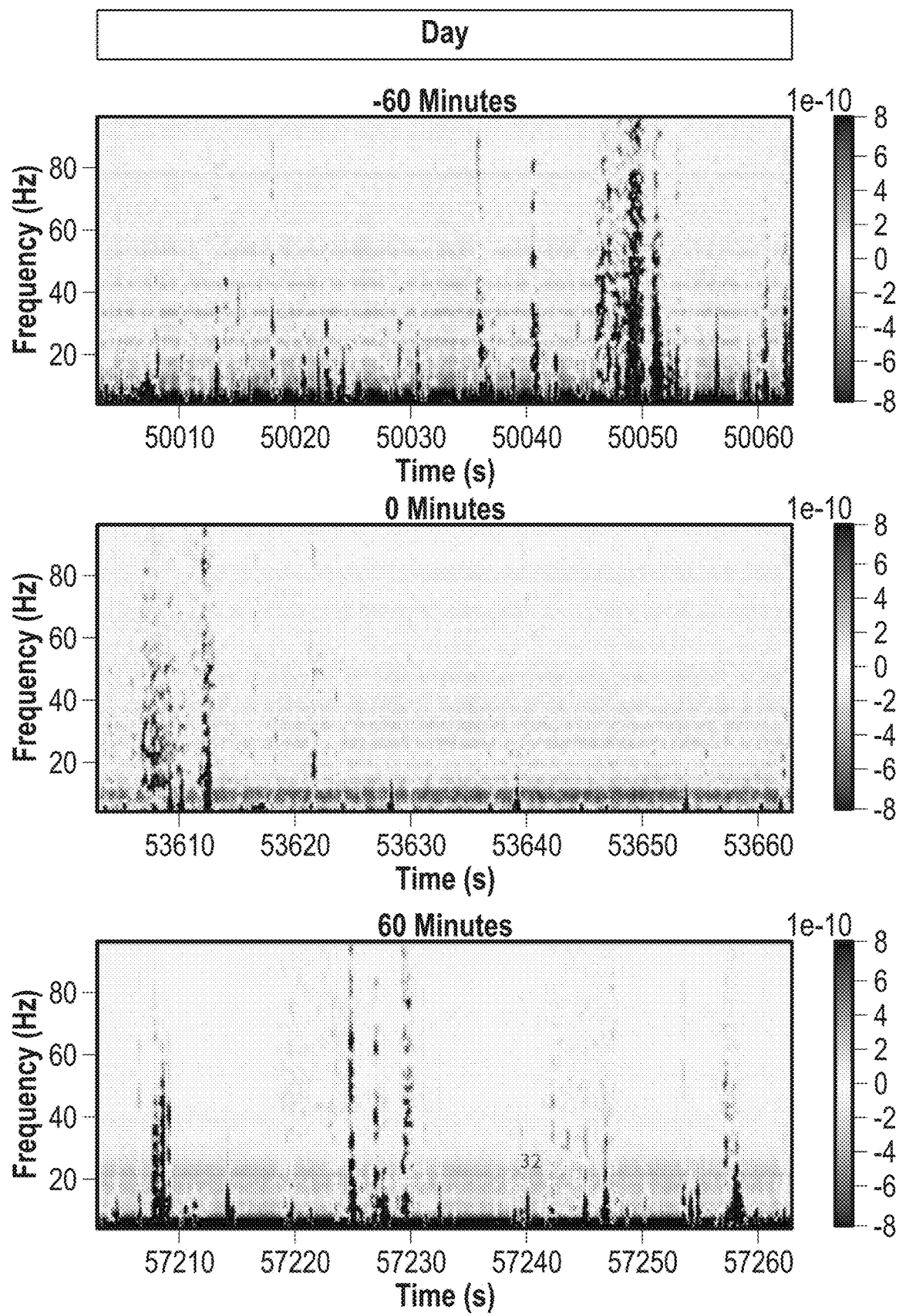

FIG. 38 shows a series of EEG plots created showing Frequency (Hz) on the y-axis (or left axis) vs Time(s) on the x-axis (bottom axis) vs Power (color scale on the right axis) of how EEG varies in the day vs night from 60 minutes before a known glucose peak to 60 minutes after a known glucose peak. The middle plot for each of day and night is the time of the peak, with 60 minutes before at the top and 60 minutes following the peak at the bottom.

Figure 39:
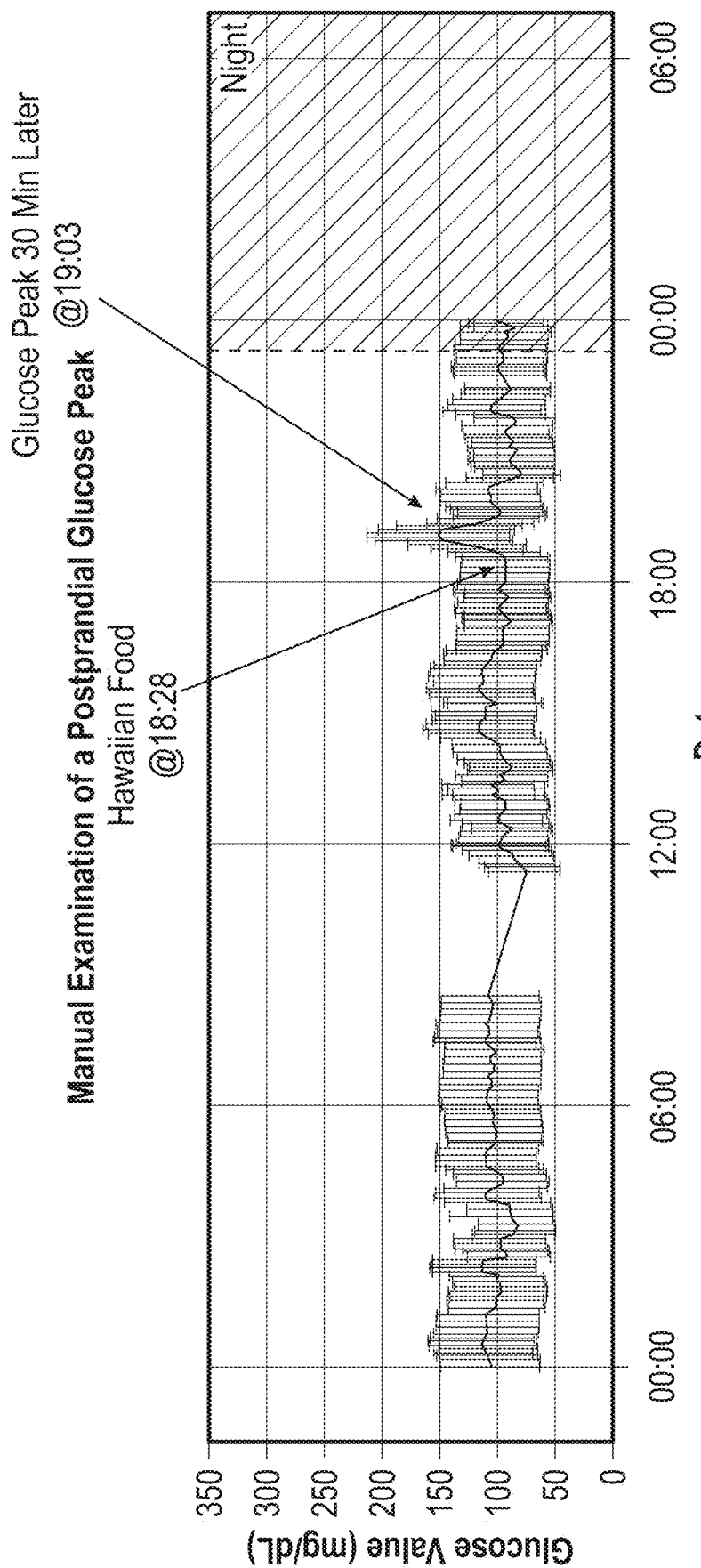

FIG. 39 illustrates an exemplary blood glucose recording (which is also representative of any sensed glucose data herein), with consumption (in this case food) at 18:28 hours and a post-meal peak 30 minutes later at 19:03 hours.

Figure 40:
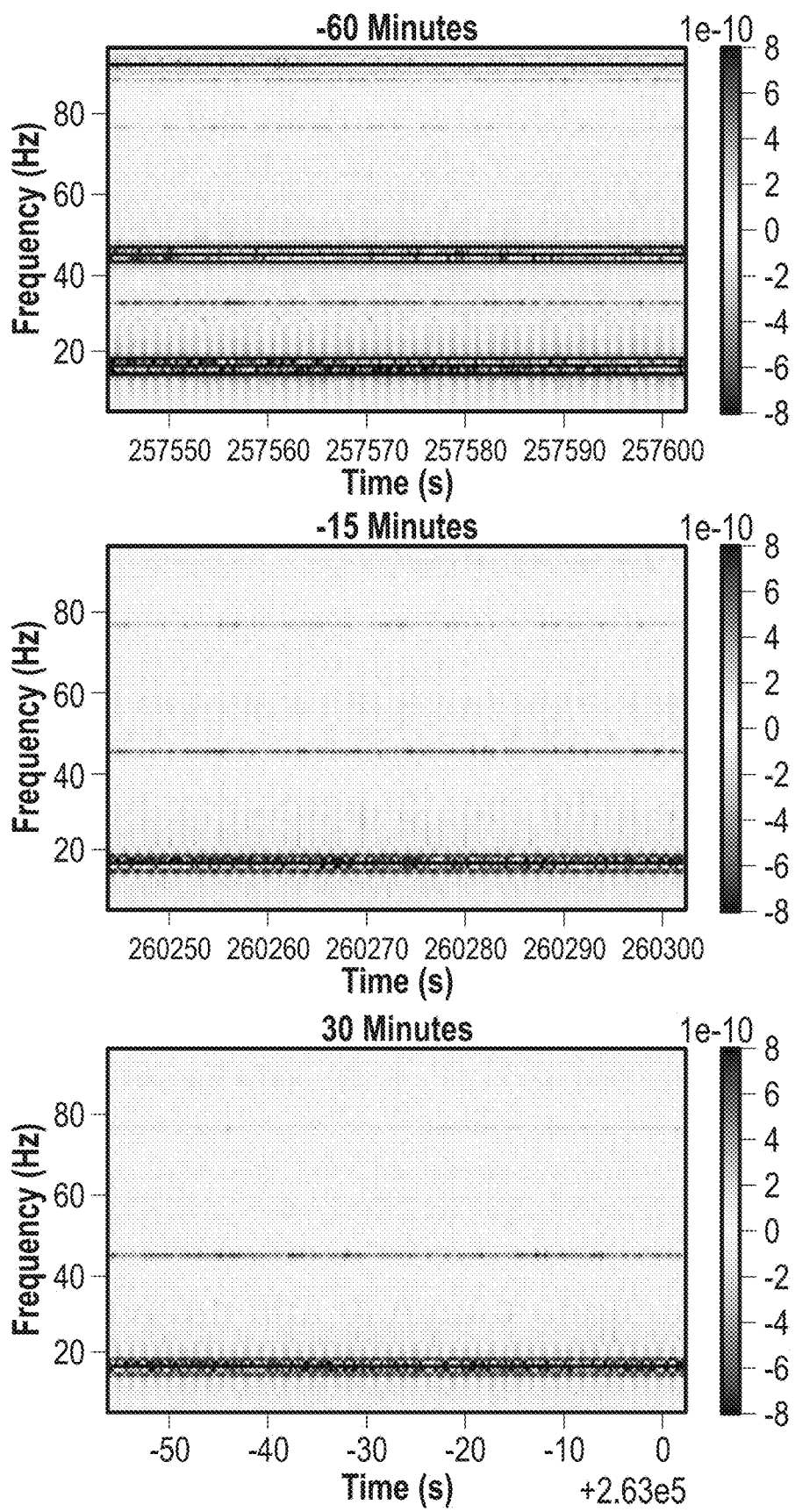
Figure 40:
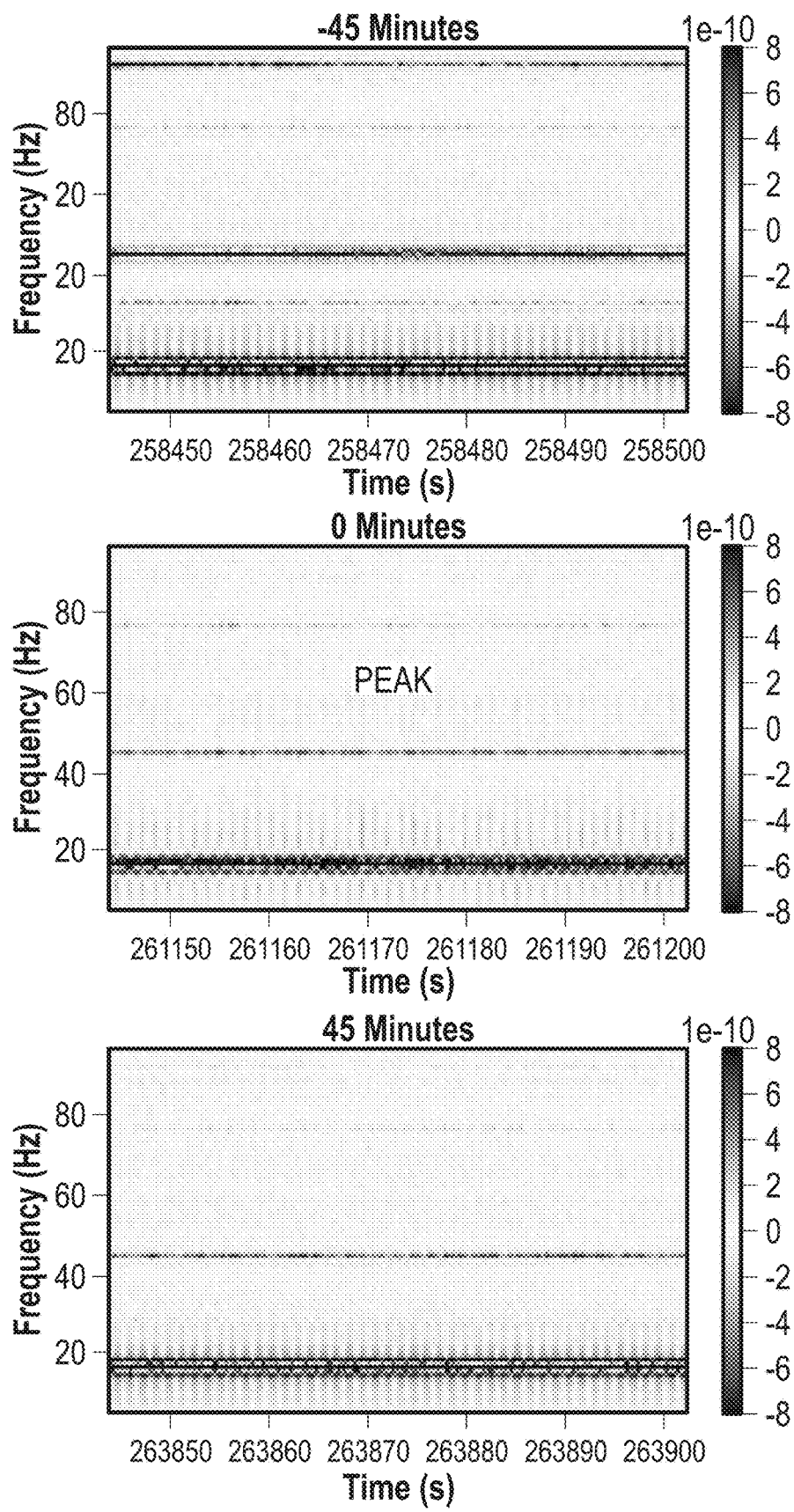
Figure 40:
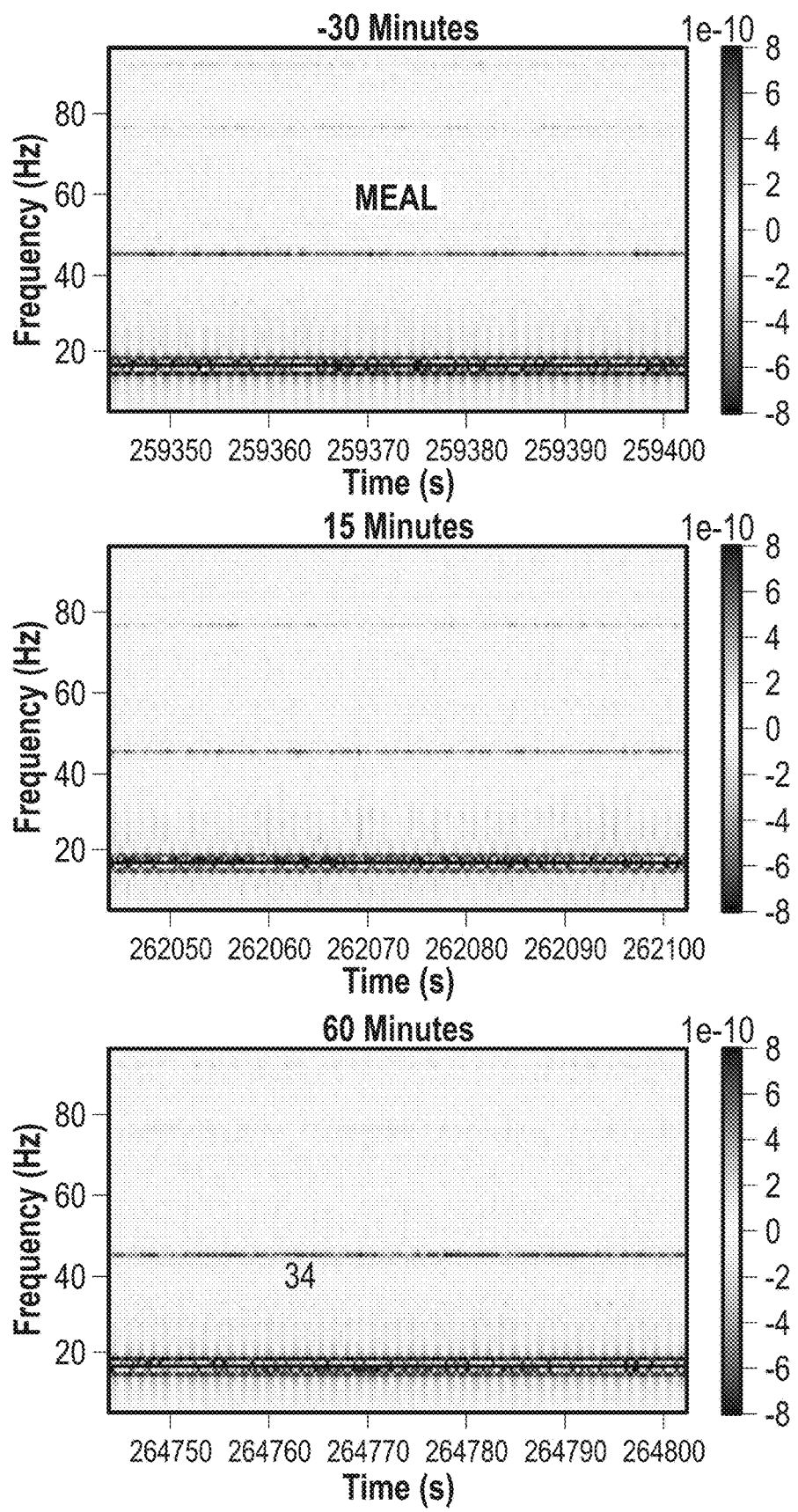

FIG. 40, similar to FIG. 38, shows a series of EEG plots with Frequency (Hz) on the y-axis vs Time(s) on the x-axis vs Power (color scale on right), from a time period spanning 60 minutes before a peak until 60 minutes after the peak, at 15 minute increments, (as labeled) with the peak being designated as time "0 minutes" (center plot in FIG. 40). The meal is labeled at 30 minutes before the peak.

FIGS. 38 and 40 illustrate an aspect of this disclosure, which includes creating or receiving (which may occur automatically) and utilizing 2-dimensional plots relating EEG data with Frequency (Hz), Time, and Power (color scale on right) as an input in any of the training methods or trained algorithms herein. In alternatives, the order of the axes may be modified. The 15-minute time increments in FIG. 40 are exemplary and not limiting in any way. For example, the time increments may be from 5 seconds to 30 minutes, for example.

In any of the examples herein, methods of predicting include sensing EEG data and predicting postprandial peaks within 5 min-90 mins of the predicted peaks.

Once an algorithm is trained on brain signal data and known postprandial peaks, the algorithm can optionally be trained to predict other blood glucose variations outside of the postprandial peaks.

The system shown in FIG. 7 is illustrative of exemplary systems and methods of using training algorithms and predicting post-meal glucose events.

One aspect of this disclosure is related to measuring or detecting 1st and 2nd order momentum of EEG data (1st and 2nd derivative) as an input to any of the methods herein. Related thereto is the use of the 1st or 2nd order momentum of EEG data to dynamically determine the optimal time window for extracting EEG information to predict glucose levels. These methods or steps may be performed by a computer executable method, which are described in more details herein.

One aspect of this disclosure is related to wearable devices and systems that are adapted to sense or record one or more different types of biosignals, and in some particular embodiments they are adapted to sense brain activity signals/data, and optionally adapted to sense additional biosignals. Any of the description that follows may be used in any of the brain activity signal/data sensing and glucose state prediction described herein (future and/or real-time), and vice versa. While the disclosure describes wearables in the context of sensing brain activity signals, it is understood that one or more concepts herein may have broader applicability outside of brain activity signal sensing (e.g., the suction ports described below) and may have applicability to devices that do not include one or more electrodes. The wearable sensing devices and systems herein may be referred to generally as wearable sensors, wearable sensing devices, sensing systems, or wearables. All of the disclosure herein related to wearable devices and systems for sensing the subject's brain activity signals/data (EEG data) is incorporated by reference into this portion to this disclosure, and vice versa.

Wearable sensors described herein are, unless indicated the contrary, considered "all-in-one," or self-contained wearable sensors, which allows them to be worn by the subject as they go about their daily life (e.g., without wires connected to a console) wherein the wearable sensors wirelessly communicate data (e.g., via Bluetooth) to a second device (which may be a subject device or other device such as a care-team device).

Figure 41:
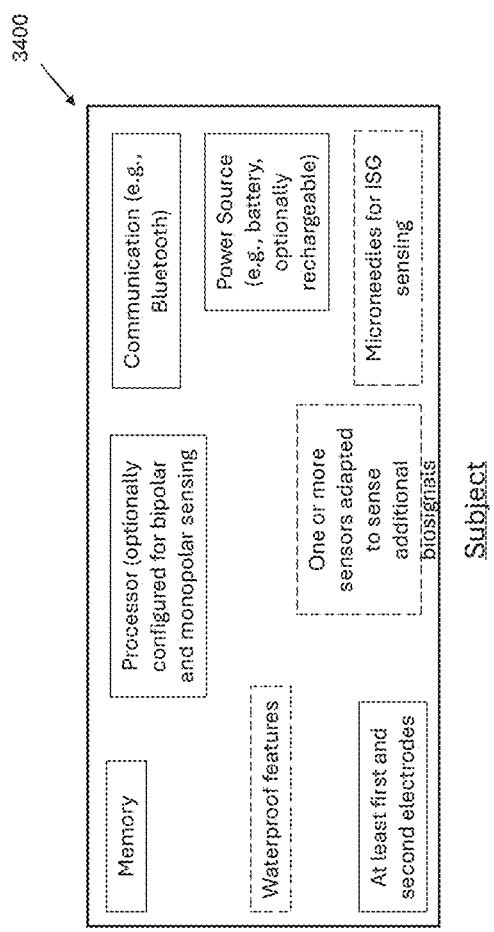
FIG. 41 illustrates an exemplary wearable sensor.

FIG. 41 illustrate a schematically illustrative wearable sensing device (i.e., wearable sensor) 3400, with optional components and features in dashed lines. Any of the features of Sensor 3400 may be incorporated with any other wearable sensor herein, and vice versa.

The wearable sensing devices herein may be configured with one or two-way wireless communication with a different device (e.g., Bluetooth), such as a subject/user device (e.g., smartphone, smartwatch). In some examples, the sensing device is adapted to continuously sense brain activity signals from the subject, for at least some continuous period or epoch of time, and continuously communicate (for at least some continuous period or epoch of time) in real or substantially real-time the raw or processed EEG data to an App on a subject device, which is described elsewhere herein.

The wearable sensing devices herein may include one or more memory units adapted to store sensed or processed brain activity signals, at least temporarily (e.g., up to 8 hours). For example, in some embodiments the data can be stored temporarily until it is communicated to a subject device, or until communication can be re-established with a user device if communication was interrupted.

Figure 42:
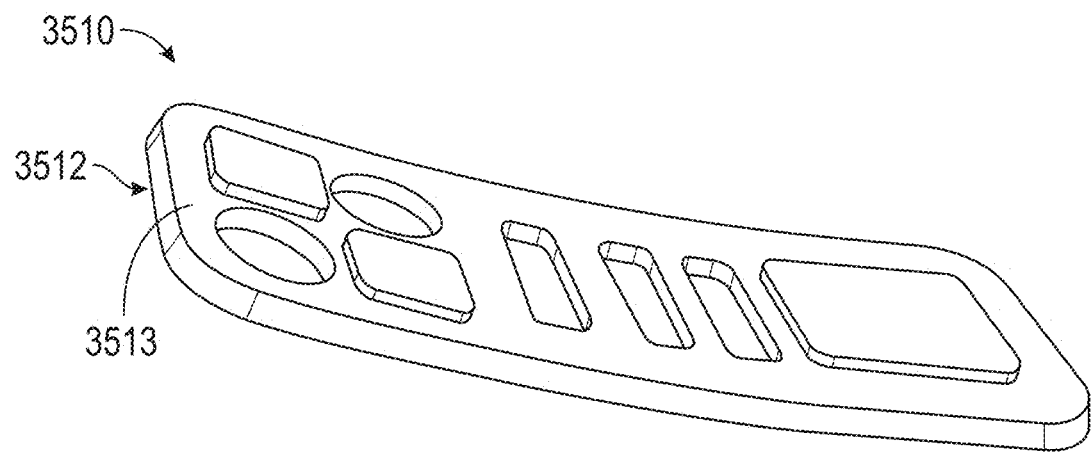
FIGS. 42 and 43 illustrates an exemplary wearable sensor.
Figure 43:
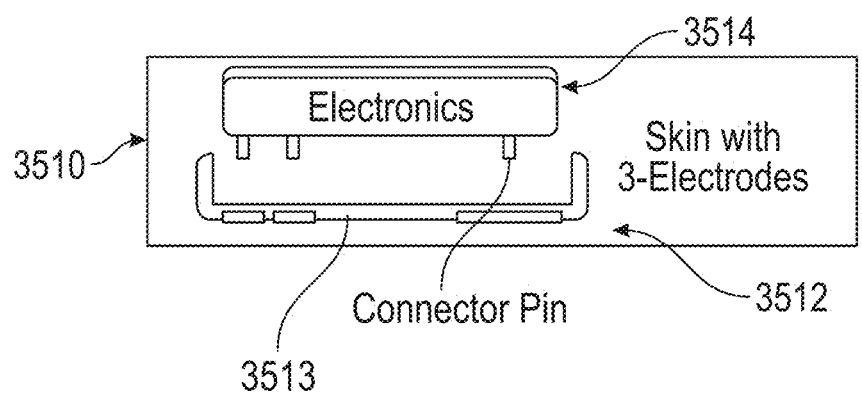
Figure 45:
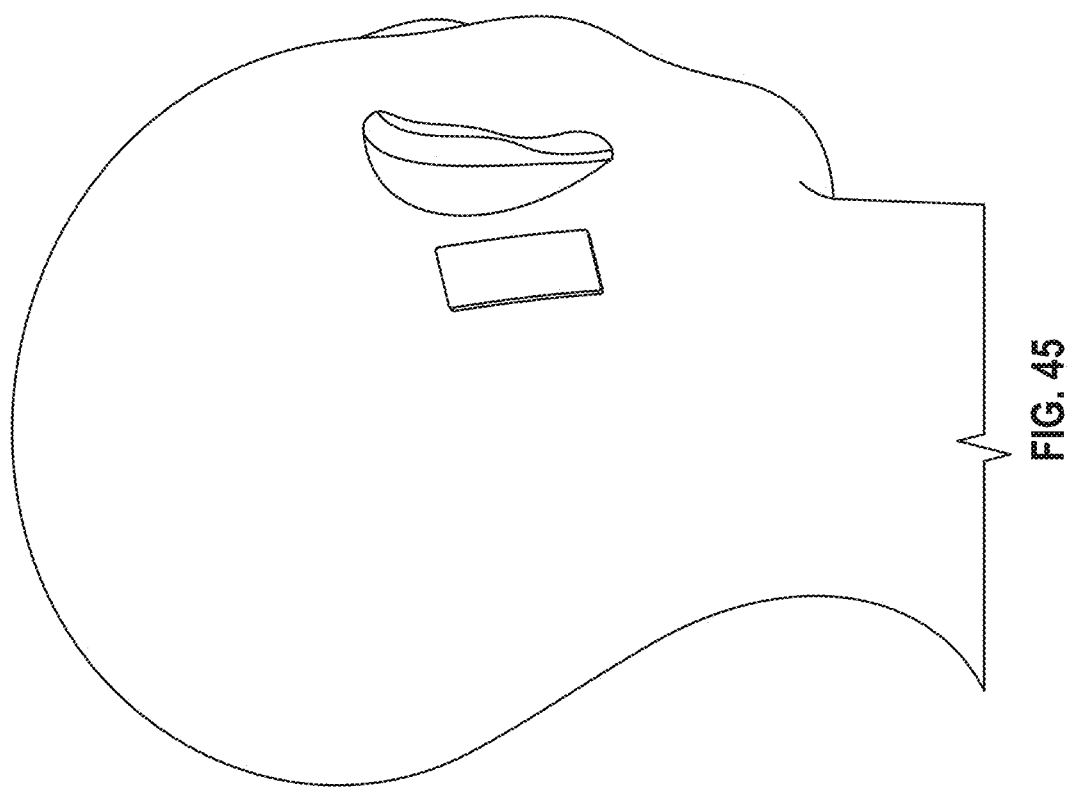
Figure 44:
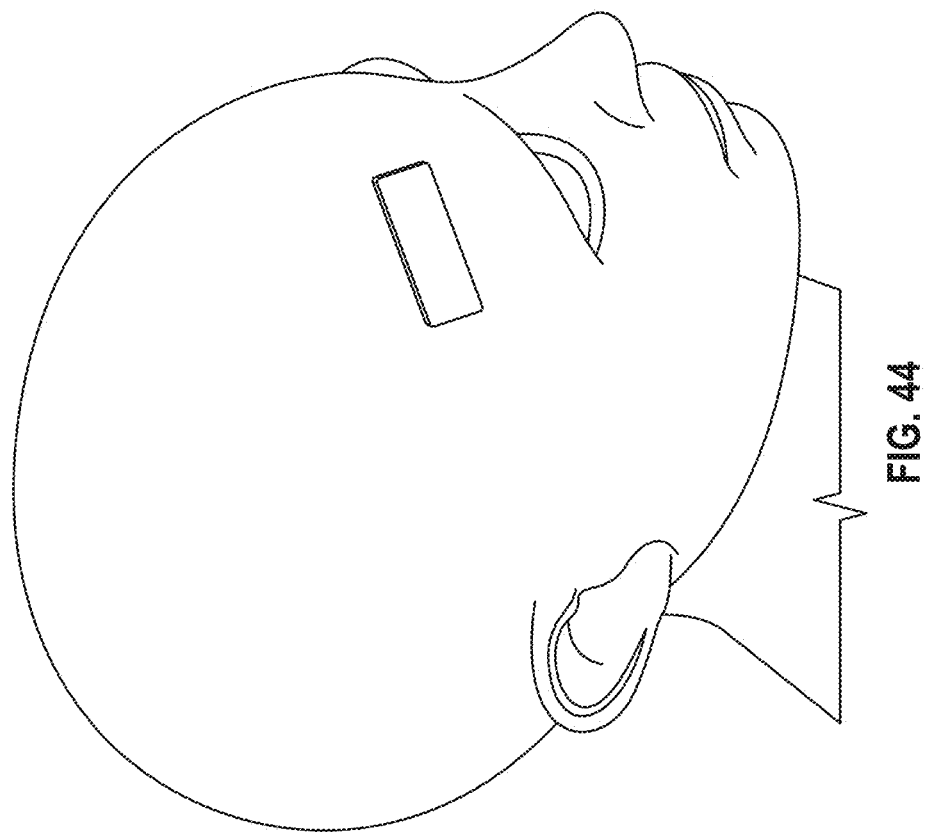

In one exemplary, non-limiting embodiment shown in FIG. 42 and FIG. 43, wearable sensing device 3510 (which may be considered wearable sensor 3510) includes a wearable sensor 3512. In this example, wearable sensor 3512 includes flexible electrode housing 3513 and a plurality of electrodes (shown) secured to the flexible electrode housing 3513. System 3510 further includes electronics member 3514 that is configured and adapted to be releasably coupled to wearable sensing device 3512 so that, when coupled, it is in communication with the plurality of electrodes. Electronics member 3514 may include connector pins as shown or other electrically conductive elements, each of which are adapted to create an electrical connection to one of the electrodes. Electronics member 3514 may be releasably secured to wearable sensor 3512 in a variety of ways, such as mechanical and/or magnetic coupling. The views of FIGS. 42 and 43 show first surfaces of each of the plurality of electrodes facing away from the flexible electrode housing 3513 so as to be positioned to be coupled to a surface of a subject, an example of which is shown in FIGS. 44 and 45 (either directly coupled or indirectly coupled to the surface of the subject). The views of FIGS. 42 and 43 also show examples of second surfaces of each of the plurality of electrodes optionally disposed within electrode wells in the flexible electrode housing 3513.

One of the plurality of electrodes may be positioned and adapted for use as a ground electrode, an example of which is shown in FIG. 42. The plurality of electrodes may also include a plurality of sensing or recording electrodes, examples of which are shown in FIG. 42 (labeled as "recording pair"). The electronics member can be adapted with a processor such that the first and second sensing electrodes can sense in either monopolar mode (each recording with the ground) or in bipolar mode (recording between the recording pair), which can provide an advantage over some devices that can only sense in bipolar mode. In monopolar mode, the third optionally larger electrode as shown is the ground, or referential electrode.

Wearable sensors herein, such as those in FIGS. 42, 43, 47A-47D, provide the ability for single or dual sensing modalities, compared with some alternative wearable devices configured for only single channel sensing.

As a mere example, first and second sensing electrodes are optionally spaced 1.0 mm-4 mm apart. A ground electrode may be spaced from the nearest of the first and second sensing electrodes a greater distance than a spacing between first and second sensing electrodes, an example of which is shown in FIGS. 35 and 36.

Any of the plurality of electrodes herein may be rigid, flexible, or comprise both rigid and flexible elements. In some non-limiting examples, sensing electrodes herein may comprise one or more of steel, gold, carbon, or silver.

Any of the electrode housings herein (e.g., 5313 in FIGS. 42 and 43) may comprise a flexible body, wherein at least a portion of the body is flexible, optionally the entirety is flexible. In some embodiments, a flexible electrode housing comprises one or more polymeric materials. In the example of FIGS. 42 and 43, the flexible electrode housing may comprise a silicone, and may consist of a silicone.

In non-limiting examples, any of the flexible electrode housings herein (e.g., 5313 in FIGS. 42 and 43) optionally has a length of 20 mm-60 mm, optionally a width of 5 mm-25 mm, and optionally a height of 1 mm to 8 mm. Dimensions in FIGS. 42 and 43 are understood to be illustrative.

The wearable sensor 3512 is adapted to be adhered to a subject's body (e.g., skin, e.g., scalp), exemplary locations for of which are shown in FIGS. 44 and 45, with FIG. 45 illustrating an exemplary behind the ear location. The sensing devices herein (e.g., 3512) may be adapted to be adhered to the subject's skin with one or more of a wet or dry adhesive, suction, or other non-permanent attachment. Some sensing devices are adapted to be adhered to the subject's skin without an adhesive, such as if using suction or other non-chemical bonding forces such as Van der Waals forces. Sensing devices herein may optionally include one or more suction ports in a flexible electrode housing (as shown in the example of FIGS. 42 and 43), wherein the suction ports may be configured as wells in the flexible electrode housing, an example of which is shown in FIG. 42. In some alternatives, not shown, the electrodes may be adapted to be adhered to the skin at least partially with suction.

Suction ports herein may be configured to suck skin in and push air out when a user pushes on the bandage to adhere it to the subject. The electrodes are also pulled towards the skin, providing electrode-skin contact (including indirect contact). Additionally, suction ports may optionally be under the electrodes so that electrodes additionally get pulled or sucked towards the skin.

While not shown, the sensing devices herein may further comprise an adhesive adapted to at least help adhere the sensing device to the subject's skin. For example, a flexible electrode housing may include an adhesive layer covering at least a portion of the flexible electrode housing. For example, an adhesive layer may cover one or more of a plurality of electrodes or a flexible electrode housing.

An exemplary advantage of the wearable system in FIGS. 42-45 is that, if desired or needed, wearable sensor 3512 can be de-coupled from electronics member 3514, and replaced with a new wearable sensor 3512. Additionally, wearable sensor 3512 may optionally be cleaned or replaced and re-coupled to electronics member 3514.

An exemplary advantage of the system in FIGS. 42-45 is that wearable sensor 3512 may comprise a flexible housing 3513, which may allow better conformability to the skin of a subject (e.g., scalp), which may facilitate better electrode-skin contact.

One aspect of this disclosure is a wearable device that comprises a plurality of optional suction adhesion ports on a first side of the device. In this aspect, the wearable may or may not include electrodes. An exemplary benefit of such a wearable is that adhesives may irritate the skin of certain subjects, and suction may be a less reactive mechanism to adhere the device to the skin. An additional benefit is the option to remove and replace the device on-demand (described in more detail below) if continuous operation is not required. Additionally, wetness from natural skin perspiration may enhance the suction and thus help adhere the device to the skin, which may help with electrode-skin contact. Furthermore, suction may allow for some amount of perspiration or other liquid to be retained between the electrode-skin interface, improving the electrical contact.

In examples in which the wearable device 3512 can be replaced, such as if the housing 3513 or electrodes deteriorate, a plurality of wearable sensors 3512 may be packaged together, similar to a package of bandages. This allows the subject to easily replace an existing wearable sensor with another without a significant interruption in EEG sensing, if that is desired. Maintaining EEG sensing as continuously as possible may be highly desirable, such as if the subject needs to or wants to regularly predict and/or manage their blood glucose levels.

In some additional examples, the electronics member is configured with a communication module (illustrated in FIG. 41), such as for Bluetooth capabilities to communicate data to a user device/App, such as one or more of a smartphone, a computer, or an insulin pump or other drug delivery device.

In some embodiments, the optional electronics member is primarily rigid and the wearable sensor 3512 is flexible. The electronics members herein may, however, optionally be at least partially or completely flexible, such as if the electronic member is a mixture of flexible and rigid components to, for example, facilitate conformability. For example only, an ASIC and a power source (e.g., battery) may be rigid, but a printed circuit board (PCB) to which they are attached may be flexible such that the whole package can optionally be curved.

Flexible electrode housings herein may be manufactured in a variety of skin tones or other colors, or they may be clear.

In some embodiments, the entire system is completely non-invasive. In some embodiments, the system may further include one or more microneedles, as illustrated in FIG. 41 to optionally sense ISG when worn about the head.

The wearable sensors herein may be waterproof, even when there is a rechargeable electronics member.

In any of the embodiments herein, the optional electronics member may optionally include one or more of a memory (which may store at a minimum of 10 hrs, for example); a signal amplifier and processor that is adapted to allow for monopolar and bipolar mode sensing; adaptation for bidirectional communication; Bluetooth capability; include one or more sensors adapted for impedance measurement to monitor adequate skin contact for recording; and/or a rechargeable power supply.

Any of the wearable systems and/or devices herein may be part of a wireless network of wearable computing devices, which may be referred to as a body area network (BAN), a wireless body area network (WBAN), a body sensor network (BSN), or a medical body area network (MBAN). The systems and devices herein may have a plurality of modes of communication that allows them to communicate with one or more different types of devices, such as other devices in a BAN.

Any of the wearable sensors herein may include one or more sensors adapted to detect or sense chewing such that the system is adapted as a chew indicator (e.g., a chew counter). For example, one or more sensors adapted to sense an indication of chew may be integrated into one or more components of wearable system 3510 or 400.

Figure 46:
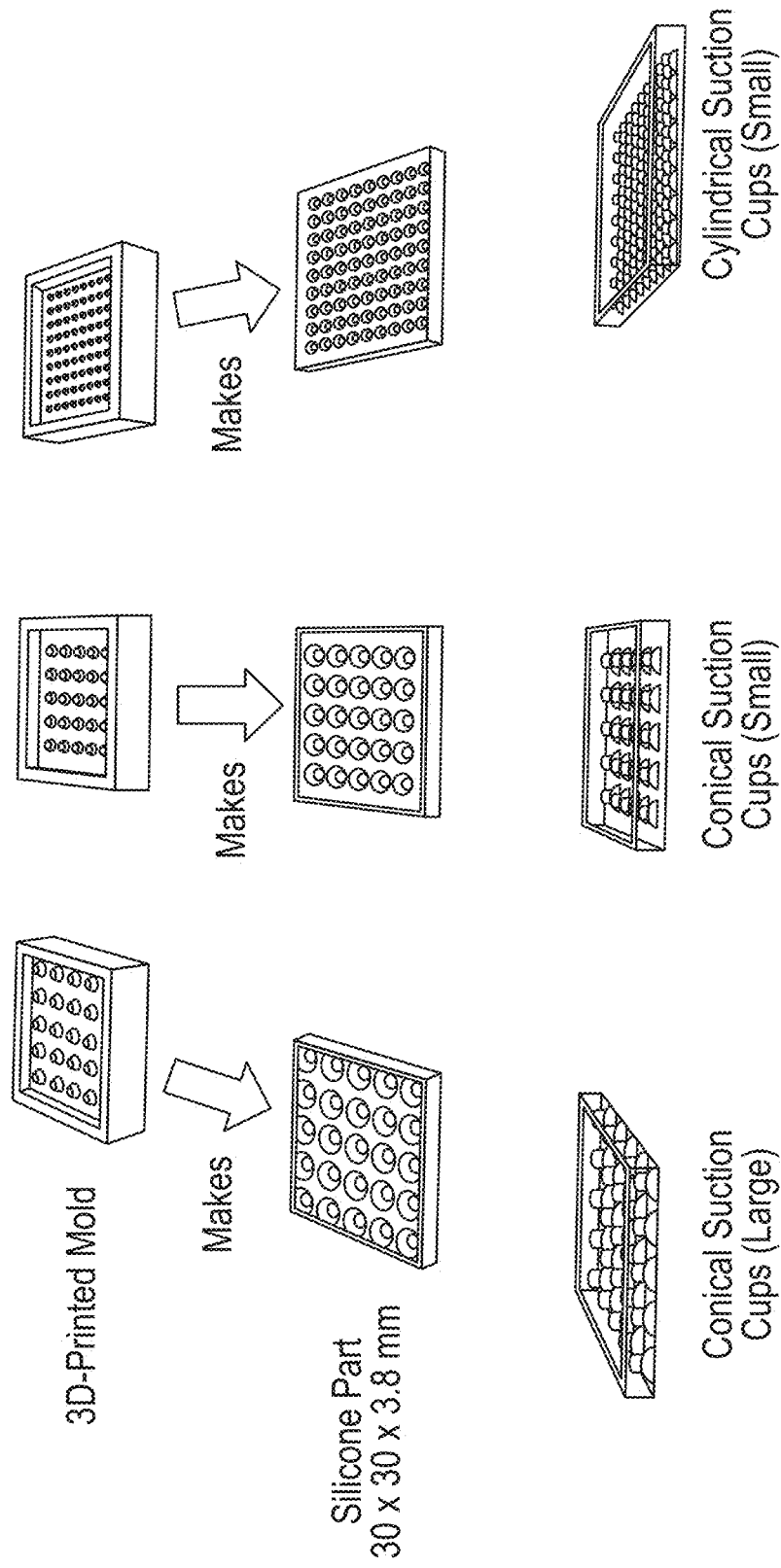
FIG. 46 illustrates exemplary steps during optional manufacturing methods of some wearable sensors herein.

FIG. 46 illustrates exemplary molds for manufacturing exemplary wearable sensing devices, including the housings herein.

In some applications, the wearable systems (e.g., an example of which is in FIGS. 42-45) may not necessarily be worn continuously, but may be worn non-continuously, such as being worn only for brief periods of time, such as (without limitation, from 30 seconds to 2 hours (including any range therein). This may be helpful if periodic EEG readings/ monitoring are all that is needed or desired, and may be referred to as an on-demand use rather than continuous use. This may be analogized to periodic finger prick glucose reading that are currently used, such as to monitor glucose levels and/or to calibrate a CGM. This approach may be useful, for example only, if a subject is primarily concerned with blood glucose levels at certain times of the day, such as after a meal when glucose levels are expected to increase. In an exemplary use, a subject may place the sensor on their body at the time of or just prior to meal-time, and leave it only for a brief period of time (5 minutes to 2 hours, for example), or long enough for the EEG data to be used to predict or monitor a prandial event. All disclosure herein related to post-prandial glucose level prediction and monitoring is incorporated into these on demand examples.

This on demand approach may also be used as an alternative to finger-prick testing, as a way to get an immediate real-time blood glucose prediction (through an App, which can present the glucose reading on the display of the user device).

Additionally, an on-demand use may be used to train an algorithm including periodically wearing the sensor while taking finger-prick glucose measurements, such as wearing the sensor for an hour before and after finger-prick measurements are obtained.

Additionally, as an example, on demand use may help a subject understand their personalized glycemic profile, such as how their glucose levels change after a meal, or certain types of food or drink.

In alternative examples, not shown, the optional electronic member (or package) may include one or more reinforcing or support elements that are adapted to reinforce or provide support to the electrode housing (e.g., housing 3513) at the location of the suction ports. The one or more reinforcing or support elements may be sized, configured and adapted to reinforce or bolster the suction port walls and help reduce the tendency of the suction ports to retract and lose their suction, which prolongs skin adhesion. In some merely exemplary embodiments, the one or more reinforcing elements may have pronged configurations, or other configurations that are adapted to provide support and reinforcement to the suction cup walls.

The disclosure that follows describes alternative wearable sensing devices (wearable sensors), but which may include one or more features from the aforementioned wearable sensing systems (e.g. more than two electrodes, one or which may be a ground electrode, and which may be configured for monopolar and/or bipolar mode sensing).

Figure 47C:
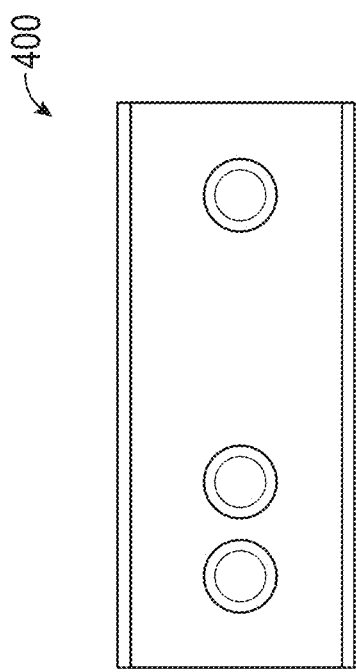
FIGS. 47A, 47B, 47C and 47D illustrate an exemplary wearable sensor.
Figure 47D:
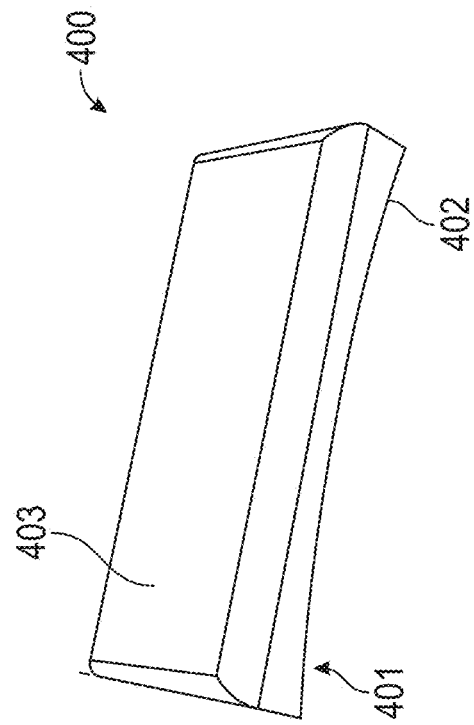

FIGS. 47A-47D illustrate a merely exemplary wearable sensing system 400. System 400 includes flexible housing 401 and a plurality of electrodes (as shown) secured to the flexible housing. A portion of each of the plurality of electrodes is within the housing (as shown in the transparent rendering in FIG. 47D), while surfaces of each of the plurality of electrodes are exposed, or facing away from the flexible housing 401, as illustrated in FIG. 47c. While FIGS. 42-45 provides an example of a system with detachable electronics, FIGS. 47A-47D provide an example of a system that is essentially an integrated system, with the electronics embedded therein and not intended to be detachable from a flexible member and reused. Certain features from the exemplary system in FIGS. 42-45, however, may still be present or incorporated into the exemplary system in FIGS. 47A-47D.

As in the example shown in FIGS. 42-45, exemplary wearable sensor 400 includes a first pair of sensing electrodes (e.g., the two electrodes to the left in the figures), and a ground electrode (the single electrode on the right in the figures). This allows the system to record in both bipolar mode (e.g., between the two sensing electrodes on the left) and monopolar mode (e.g. each of the two left electrodes referenced against the electrode on the right spaced further away as the common ground or reference electrode). The monopolar signal, while more susceptible to artifact due to the voltage measured across a greater distance between sensing electrode and the common reference electrode, has a much greater amplitude and greater sensitivity to neural signals, thus advantageous in wearable systems that record brain activity signal data from a subject. The capability to record in monopolar mode can also help reduce noise, which may be important when recording from localized regions of the head and recording relatively low power brain signals. Systems herein thus provide advantages over brain activity signal recording systems that have electrodes in close proximity and are adapted to record only in bipolar mode.

In system 400, the distance between the two sensing electrodes disposed in relatively close proximity to one another may be from 1 mm to 7 mm (measured from center of electrode to center of electrode, as shown).

In system 400, the distance between a nearest of one of the sensing electrodes and the reference ground electrode may be from 8 mm to 35 mm, an example of which is shown as 15 mm.

In system 400, flexible electrode housing 401 comprises a skin facing surface 402 configured and positioned to be placed against tissue on a head of subject (directly or indirectly), and a second side 403 spaced from the skin facing surface. The skin facing surface 402 optionally has, as is shown in the side view of FIG. 47B, a concave or generally concave shape, and optionally wherein the second exposed side is at least partially planar, as shown. The merely optional concave curved surface of the skin facing surface may be configured to improve placement behind the ear or on the scalp, but depending on the flexibility of the wearable device, the wearable may not have a curved skin facing surface. In some embodiments, the skin facing surface has a radius of curvature from 0.5 cm to 4 cm along at least a portion of the surface, optionally with a constant radius of curvature along the entire surface. It some embodiments the radius of curvature may vary to some extent along the surface of the first tissue side.

Figure 47A:
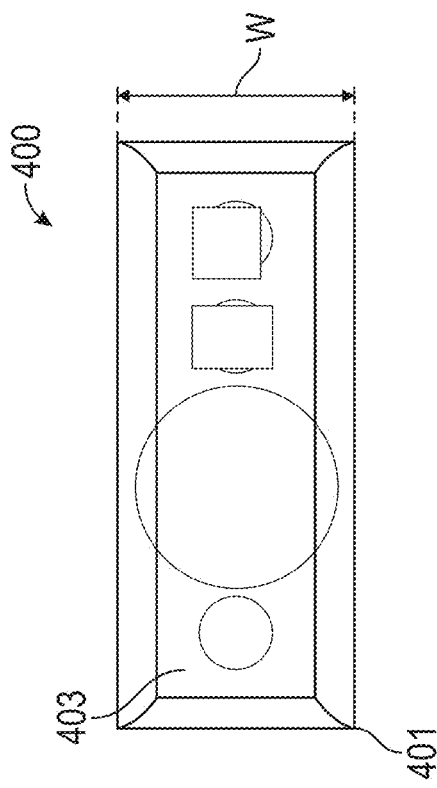
Figure 47B:
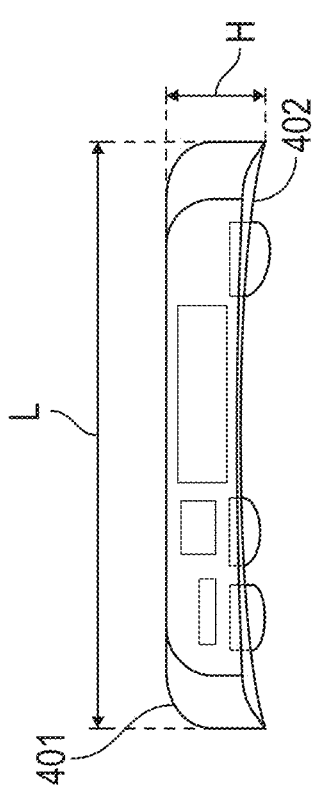

Skin facing surfaces of each of the plurality of electrodes face away from the flexible housing to facilitate placement against the tissue, either directly against tissue or indirectly against tissue, as shown in FIGS. 47B and 47C. In this particular example, surfaces of each of the plurality of electrodes face away from an optionally concave skin facing surface of the flexible housing, as shown.

Wearable sensor 400 illustrates an example where the plurality of electrodes are aligned linearly or substantially linearly along a length "L" of the flexible housing, as shown.

Wearable sensor 400 illustrates an example where the height of the flexible housing (e.g. "H" dimension labeled in FIG. 40B) may be from 3 mm to 10 mm.

Wearable sensor 400 illustrates an example where the length of the flexible housing (e.g. "L" dimension labeled in FIG. 40B) may be from 12 mm to 40 mm.

Wearable sensor 400 illustrates an example of a flexible electrode housing that has, in a top or bottom view (e.g., FIGS. 47A and 47C), a rectangular shape or generally rectangular shape. The flexible electrode housing may have other shapes, however, in top and bottom views.

As shown and as described herein, the wearable sensor may further include a power source (e.g. a battery), optionally a rechargeable power source, embedded in the electrode housing (which is optionally flexible). The electrode housing may optionally be adapted to inductively recharge a battery, and optionally via the plurality of electrodes, which can enhance water resistance of the device (i.e. a port is not required for a charging cable).

With any of the wearable sensors herein, the plurality of electrodes may be rigid, optionally gold plated.

With any of the wearable sensors herein, the plurality of electrodes may be rigid and may comprise one or more polymeric materials, optionally further comprising conductive epoxy.

With any of the wearable sensors herein, the wearable may be water resistant, and may comprise embedded epoxy to improve the water resistance.

With any of the wearable sensors herein, a flexible electrode housing may comprise a flexible overmolded wearable housing, manufactured by overmolding.

With any of the wearable sensors herein, the plurality of electrodes may extend proud of the skin facing surface or side of the electrode housing.

With any of the wearable sensors herein, a flexible overmolded wearable housing may comprise a silicone.

Sensor 400 (or any other wearable sensor herein) may include, as shown, an adhesive patch or layer disposed on a skin facing surface of the electrode housing. The system may include a removable layer (e.g. paper) that when removed from the adhesive exposes the adhesive to facilitate adhering the electrode housing to the skin of a subject. For example, an adhesive layer may be a polyester fabric, such as (without limitation) 3M™ Medical Tape 4578.

With any of the wearable sensors herein, an adhesive layer may leave exposed skin facing surfaces of the plurality of electrodes, or it may cover the skin facing surface of the electrodes. Adhesive layers may have selectively conductive regions at the location of the electrodes to create a monolithic patch (i.e., no electrode openings). To further improve skin-electrode contact, any of the wearable sensors herein may incorporate one or more spring-loaded or spring-like electrode contacts to accommodate curvature and/or anatomical differences between users.

Any of the wearable sensors herein may include a power source (e.g. battery) embedded within a flexible electrode housing (e.g., as shown in FIGS. 47A and 47B). It may also optionally include kinetic charging capabilities, such as triboelectric generators, to harvest movement energy and extend battery life.

Any of the wearable sensors herein may include an EEG ASIC embedded within a flexible electrode housing (e.g., as shown in FIGS. 47A and 47B).

Any of the wearable sensors herein may include a Bluetooth module disposed within a flexible electrode housing (e.g., as shown in FIGS. 47A and 47B), the system adapted to communicate information to an external device (e.g., a smartphone).

Any of the wearable sensors herein may include one or more memory structures disposed within a flexible electrode housing (e.g., within an EEG ASIC) adapted for on-board storage, at least temporary storage of sensed information or information indicative of sensed information.

Any of the wearable sensors herein may include a processor within a flexible electrode housing, such as within an EEG ASIC.

Wearable sensor 400 (or any other wearable sensors herein) may be configured for real-time (or near real-time) streaming of sensed brain activity signals to an external device, which optionally has stored thereon any of the Applications described herein.

Sensor 400 (or any other wearable sensors herein) and/or an Application stored on a subject device that is in communication with sensor 400, may be configured to provide an alert (e.g., a vibratory alert, audible alert) if the system detects an event, such as an abnormality or condition outside of what is expected or desired.

System 400 and any of the Apps herein may be configured for two-way communication, optionally wherein the Application is adapted to allow a user to provide input on EEG tracings/recordings or other input temporally related to EEG tracings/recordings.

One optional aspect of the disclosure herein is related to methods of manufacturing a wearable sensing system, which may optionally comprise overmolding a flexible housing at least partially around any of the wearable systems components herein, such as those shown in FIGS. 47A-47D. The electrodes are partially embedded in the overmolded housing such that surfaces of each of the plurality of electrodes are exposed to facilitate their placement against tissue to facilitate sensing brain activity signals. Forming the flexible overmold may comprise forming a curved tissue side of the overmold, and wherein the plurality of electrodes may be proud of the curved tissue side, or they may be flush or substantially flush with the curved tissue side. The method may include securing an adhesive to a tissue side of the flexible overmold.

Any of the systems herein may be adapted to provide additional functionality and benefits outside of prediction glucose states. For example, the following aspects may be incorporated into any of the devices, systems and methods of use herein: Device counters/diagnostics to provide info to the users beyond the EEG. Exemplary diagnostics include, without limitation, counters of one or more of the following occurrences: detection of noise (continuous high frequency/high amplitude signal), which can help troubleshoot EEG signals; detection of prolonged increase in overall power and area under the curve, which may, for example, indicate a neurological event such as a seizure; detection of prolonged (e.g., >60 sec) lack of EEG signal, which may, for example, indicate that a wearable sensor has come loose or off; detection of high impedance, which may, for example, indicate that the sensor may be loose or electrodes not touching skin; detection of various sleep stages (slow wave—2-4Hz, high-amplitude; high (>12 Hz) to low (<12 Hz) frequency power ratio); sudden high slope decreases or increases in band-specific or broadband power that may indicate the onset of a stressful event; the anticipation of a highly appetitive or insulin-demanding food intake; or onset of exercise/anticipation of exercise. In any of the examples herein, detecting any of these occurrences may result in an alert (of any type) to the patient or user to indicate that, for example only, the sensor is malfunctioning, needs to be placed differently or a large/significant neurological event has occurred. The alert may also provide an overall indicator of sleep quality after a night's sleep. The alerts may be communicated to the user via an App (on a smartphone) and/or via the wearable sensor (e.g., a vibratory alert if not positioned satisfactorily).

Any of the Apps herein may be adapted to initiate an output to the user to indicate a status of the wearable sensing system. For example, the status may comprise a functional characterization of the wearable sensing system, such as if the wearable sensing system is functioning (e.g. green light indicator on a display screen controlled by App) or not (e.g. red light indicator on a display screen controlled by App). The status may comprise a position indicator that indicates if the wearable sensing system is in a satisfactory position on the subject (or otherwise indicates that the position is appropriate for its use to sense brain activity signals). A position indicator may indicate if the wearable sensing system is in a satisfactory position on the subject to facilitate satisfactory EEG sensing for any of the methods or uses herein (e.g., real-time glucose monitoring and/or predictive glucose forecasting).

Any of the bidirectional communication herein optionally includes adaption so the wearable sensing system can send alerts to the patient or user (e.g., via an App) and the patient or user can also communicate marks (or other indicators) back to the wearable sensing system from the App, which marks an event on the EEG tracings/recordings.

Any of the wearable sensing systems herein may include preferential storage of events of interest if/when they are detected. Once an event is detected, EEG may be stored for an epoch of time. For example only, if the system (wearable and/or App) detects an event of prolonged overall power, a minute EEG clip may be stored (or for some other time period). A storage buffer of about 30 seconds or other time period may facilitate the preferential storage functionality, similar to a digital video recorder.

In some embodiments, the sensing systems herein may also include additional sensors adapted to sense other biosignals (as illustrated in FIG. 41), such as, without limitation, skin temperature, heart rate, heart rate variability, movement (e.g. accelerometer), peripheral oxygen saturation (spO2), gastric motility (EGG with abdomen sensor), and galvanic skin response (stress measurement), step counters, chewing counters, fall counters, convulsion counters. The sensing systems herein may also include additional sensors such as one or more of optical sensors (e.g., photoplethysmography sensors), inertial sensors (e.g., accelerometer/gyroscope/magnetometer), or electrodermal activity sensors (e.g. for skin conductance; galvanic response).

As mentioned above, systems herein may be adapted to detect or sense chewing, data for which may be sensed by the wearable sensor and communicated to a user device (e.g., a chew counter). It is known that glucose levels rise after a meal (post-prandial), and thus the precise time or timing of chewing can be used as input to any of the Apps herein to help predict an increase in BG levels. Wearable sensors adapted to be worn in or around the ear are close to the jaw (examples of which are described herein) and are thus particularly well-placed for sensing chewing. Chew sensors can be adapted to distinguish chewing from talking or teeth grinding, which are not indicators of consumption. For example, chewing may be distinguished from talking due to the relative lack of closure during talking (e.g., teeth not making contact with each other). Teeth grinding may be distinguished due to, for example only, a lack of sufficient repetitive opening and closing movements, which may occur more frequently with chewing.

Any of the wearable sensing systems herein may be adapted to measure impedance values within the sensing systems.

Any of the wearable sensors herein may also include a vibratory element that is, upon activation, adapted to cause vibrations, which can optionally be part of an alert system to the wearable.

In some embodiments herein, the systems herein may also be adapted for sleep metric measurements (e.g., duration, sleep stage measurement, etc.).

Aspects of this disclosure are related to predicting future glucose states or future glycemic events (or risks thereof). Predicting future glucose states may include predicting future blood glucose levels or risk indicators at some time in the future, such as within an hour (e.g., 2, minutes, 15 minutes, 30 minutes, 45 minutes), one or more hours, such as 1 hour, 2 hours, 3 hours, 4 hours, 5 hours, 6 hours, 7 hours, 8 hours, 9 hours, 10 hours, or more, or any range of time from 30 seconds to 10 or more in the future.

Any of the methods and systems herein that are adapted to predict a glucose state can also be considered to be configured to predict a glycemic event. For example, if a system herein is stored with thresholds for glucose values, and the system herein is configured to send an alert if a threshold is near or reached, the system or method herein is considered to be predicting a glucose state. A glycemic event as used herein may refer generally to user glucose information, and/or a glucose level that is above or below certain levels, such as above or below standard glucose levels, or other patient selected levels.

Methods and systems herein may optionally be adapted to provide one or more generalized risk levels or risk indicators for entering or having a future glycemic state within one or more certain periods of time in the future. For example only, a predicted risk level may include a plurality of risk indicators, such as low risk, medium risk, and high risk. Optional risk indicators may optionally be visually presented on a display of a device (examples provided herein, such as a smartphone or smartwatch), such as a green light on a display for time in the future where risk is low, a red light on the display for time in the future where risk is high, and a yellow light on the display for time in the future where risk is medium.

While some parts of the disclosure herein may be related to predicting a future glucose state, such as levels or risk indicators, an aspect of the disclosure herein is optionally related to predicting real-time glucose states. The phrase "real-time" as used herein refers to actual blood levels that are occurring in the subject's blood at that time. The systems and methods herein may thus optionally be adapted to predict real-time or future glucose states (such as levels), or information indicative thereof. The systems herein may thus also be considered to be continuous glucose monitors, similar to existing monitors.

Methods and systems herein may be configured to predict a glucose state. Methods and systems herein may also optionally be configured to manage one or more aspects of the predicted state, including optionally preventing a forecasted glucose state or event from occurring. Some aspects of this disclosure are therefore related to the management of blood glucose levels, wherein the term management as used herein may include one or more variety of steps or actions that provide a benefit to the subject.

A "forecasted" glucose state (or derivative thereof) as used herein refers to a predicted future glucose state as that phrase is used herein.

Management may include providing information to a subject via any of the Apps herein, such as with an App output and/or alert. For example, methods and system may be adapted to communicate insulin and/or medication needs to a user based on predicted glucose states. Additionally, for example only, automated meal and exercise recommendations, examples of which are shown in FIG. 31 may be part of management herein.

In some non-limiting examples, management of blood glucose levels includes preventing a glycemic event, such as a hypoglycemic event or a hyperglycemic event (or at least reducing the likelihood thereof). In some examples, management of blood glucose levels optionally also includes ceasing or minimizing the severity of an existing glycemic event. Methods of management herein may optionally include guiding medication and insulin (long/short acting) dosage based on a predicted glucose state (real-time or future).

It is understood that aspects of this disclosure that are related to predicting glucose levels may or may not be incorporated with aspects of this disclosure related to management of blood glucose levels.

A merely exemplary method of glucose management includes closed loop functionality, and optionally may include a pump worn on the subject that may be adapted to deliver one or more agents (e.g., glucagon, insulin, etc.), which are currently worn by some patients and used with existing CGMs. For example, one aspect of the disclosure is a method of controlling future glucose levels in a patient in response to predicting future glucose states (although other patient inputs may be used as part of the controlling process—e.g. HR, skin conductance, or any other biosignal herein). In this exemplary aspect, controlling may include delivering insulin or glucagon to a patient before a glucose level deviates from a desired range/limit. In this aspect, controlling may include delivering insulin to a patient at a time when the glucose level is still in a safe range (e.g., 70-180, 80-170, etc.). In this aspect, controlling may include maintaining glucose levels within a safe/preferred range. In this aspect, controlling may include delivering an agent (e.g. insulin) before the time at which glucose levels are predicted to deviate from a safe range. In this aspect, controlling may include delivering a particular dose of insulin based on the time the glucose levels are predicted to deviate from a safe range. In this aspect, controlling may include delivering a dose of insulin that is different from the dose that would be administered in response to a real time glucose level monitoring process, such as via a CGM.

The systems herein may optionally include a multiple-chamber pump, such as a dual chamber pump adapted to deliver insulin and glucagon to manage future glucose levels. The systems herein may be adapted and configured to integrate with Bluetooth-enabled insulin pumps (e.g., Omnipod).

Any of the systems and methods herein may optionally be adapted to deliver insulin when a hyperglycemic event is predicted (real-time or future). Any of the systems and methods herein may optionally be adapted to deliver glucagon (e.g., intranasally; with a pump, etc.) when a hypoglycemic event is predicted. As an example of Management of hypoglycemia herein, in any of the methods herein, an alert or recommendation to consume, for example, a high sugar drink.

Any of the systems and methods herein may include one or more of oral medicine delivery, subcutaneous delivery, or delivery via a pump.

Methods of predicting glucose states herein may optionally be performed on a personal device (or a care-team device), such as a smartphone, tablet, smartwatch, and which may include one or more processors thereon adapted to execute one or more methods/algorithms stored thereon. Any type of executable application may be referred to herein as an "App," and may be adapted to, in response to receiving or based on raw and/or processed EEG data, including only a subset of sensed data (or information indicative of the raw data, processed data, and/or a subset thereof) that has been sensed from the subject, cause the performance of the glucose state predictions herein. In some alternatives, one or more processing steps may take place within the wearable sensing device (e.g., scalp device or sub-scalp device), which is an example that methods herein (including portions thereof) may be performed in one or more different devices.

One or more aspects of a predicted glucose levels may optionally be visually represented or presented on a display of a device, examples of which are shown in FIG. 29, FIG. 30, and FIG. 31 (e.g., smartphone, tablet, smartwatch, electronic ophthalmic device such as a contact lens, or glasses). For example only, an executable application (an "App") may be adapted to visually present a risk indicator and/or predicted glucose levels for some time period in the future, and which may be updated (continuously or periodically) such that the forecast includes predicted levels for that particular time period in the future (e.g., 1 hour, 2 hours, 3 hours, 4 hours, etc.). Additionally, for example only, an App may be adapted to visually present or indicate a specific time at which a glycemic event is forecasted to occur, examples of which are shown in FIG. 29 with the high and low visual markers, or the App may provide a discrete time for a predicted glucose event (e.g., 4:17 pm). Additionally, for example only, an App may be adapted to present a timer with a countdown indicating the time remaining before a predicted glycemic event.

In some examples, the methods herein may optionally be adapted to provide a relatively short-term prediction of future blood glucose values in advance (such as 1 hour in advance, 2 hours in advance, 3 hours in advance, etc.), and a longer-term "risk forecast" of blood glucose hours in advance (e.g., such as 10 hours in advance, 11 hours in advance, 12 hours in advance, etc.). Any of the methods herein (e.g., an App on a personal device) may optionally be adapted to communicate an actual and/or forecast of future glucose levels and/or risk indicators to a patient/care team, optionally to one or more different devices (an example of which is described herein as a Portal, examples of which are shown in FIG. 21A and 21B). Any of the methods herein (e.g., an App on a personal device) may optionally be adapted to provide a user/patient with a relatively longer (e.g., 10+ hours) forecast of risk indicators, and optionally may be adapted to provide suggested (e.g., optimal) times of day to perform certain activities, such as exercise, eat, take medication based on the forecast (examples of which are shown in FIG. 31). Any of the methods herein (e.g., an App on a personal device) may optionally be adapted to visually present (e.g., plot) an amount (e.g., percent) of time in optimal/preferred glucose range and time spent out of the optimal/preferred range, wherein the range may be adjustable and/or personalized, optionally wherein the method (e.g. App) is adapted to allow for personalized adjustment and setting of the range via interaction with a display of the personal device.

An of the Apps herein are optionally adapted to store EEG data (raw and/or processed), and optionally until is transferred to a different device, such as an optional online portal described herein. A subject device may have more data storage, so it may be better suited to store more data, allowing a wearable sensor to have a smaller form factor.

Any of the Apps on a personal/subject device herein may be adapted to perform any of the methods herein (e.g., executable methods, such as forecasting).

One aspect of the disclosure is a computer executable method that is adapted to present interactive user input features (e.g., icons on a screen, up/down arrows, audible instructions, etc.) that allow a user (patient and/or care team member(s) to adjust a range of desired glucose levels. Any other aspect of the disclosure herein may be incorporated with this aspect.

A glycemic event as that used herein is an example of a glucose state.

Any of the methods and systems herein may optionally be adapted to provide or initiate an alert upon the occurrence of an event for which the system is adapted to initiate and/or provide an alert. For example, systems and methods herein may provide or initiate an alert if an existing glycemic event has been detected and/or when a future glycemic event has been forecast. For example, once a future glycemic event has been forecast any of the alerts herein may be triggered (audible alert, text alert, email, vibratory via the wearable sensor, alert to patient and/or caregiver/care team, etc.). Any of the methods herein (e.g., an App on a personal device) may optionally be adapted to provide or initiate an alert when glucose is trending out of range and/or is currently out of range. Any of the methods herein (e.g., an App on a personal device) may optionally be adapted to provide or initiate a relatively high frequency pitch (47-65 Hz) alert when glucose is trending out of range, which may alert a service animal to the forecast or detected glycemic event. One aspect of this disclosure is an executable method that is adapted to provide or initiate a relatively high frequency pitch (e.g. 47-65 Hz) alert when a medical event has been detected and/or forecast, such as a glucose level trending out of range, a seizure is detected or predicted, or loss of consciousness predicted, etc. In some examples, non-audible methods (e.g. low amplitude vibration (e.g. with piezo)) may be preferred, such as in public settings. Some examples may include bone conduction of an audible signal.

One or more aspects of the actual and/or forecasted blood glucose levels (or information indicative thereof or related thereto) may optionally be communicated, optionally to the subject and/or third party (e.g., caregiver, family member, examples of which are shown in FIGS. 21A and 21B). One or more aspects of the actual and/or forecasted blood glucose levels may optionally be communicated to one or more devices, which may be the same as or different than the device that predicts the actual and/or forecast blood glucose information.

The methods and systems herein may optionally be adapted to continuously stream real-time EEG data to a different device, such as any of the personal devices herein (smartphone, watch, etc.). Any of the apps herein may thus be receiving continuous or near-continuous real-time EEG data that is being sensed from the patient, and using the continuously streamed real-time EEG data to make the predictions.

The methods and systems herein may optionally be adapted to receive one or more non-EEG patient biosignals (parameters), such as any of the additional optional biosignals herein (e.g., skin conductance, heart rate, HRV, blood pressure, etc.), any of which may be additional inputs used at least partially by and with the brain signals to predict the predicted glucose states.

Any of the methods herein (e.g., an App on a personal device) may optionally also be adapted to receive one or more inputs, optionally from one or more of a subject or caregiver. In this example the inputs are different that biosignals sensed by one or more sensors on a wearable. For example, any of the methods herein (e.g., an App on a personal device) may optionally be adapted to allow for user-input of information such as insulin administration/dose, intake and/or timing of medication, food related information (when, what), exercise, stress, sleep, illness, or the intake/timing of drugs/substances that may affect blood sugar (e.g., any of the substances/medicines listed at https://www.trihealth.com/institutes-and-services/diabetes/living-w-diabetes/medications/medications-that-affect-blood-sugar), for example.

Any of the methods herein (e.g., an App on a personal device) may optionally be adapted to allow a user (patient and/or caregiver) to mark or otherwise indicate events on raw EEG tracings (or processed EEG data), such as provide an indication when a meal was consumed or the time of exercise.

Part of this disclosure includes methods that are adapted to use one or more inputs to refine or train (e.g., increase the accuracy thereof) any of the forecasting algorithms herein, and optionally the inputs may alternatively or in addition to refine or train any of the CGMs herein. For example, and without limitation, inputs include, without limitation, inputs that are input manually via a user and/or inputs received from other devices (e.g., pumps, glucose meters, and/or CGMs). For example, Apps herein may be adapted to receive information from a glucose meter and/or CGM (e.g., blood glucose readings/values) and use that information to refine a forecasting algorithm. A user may optionally input blood glucose values. Inputs in this context may further include, without limitation, what food was consumed and/or when they consumed the food; when insulin was administered and/or a dose, or any other input that is related to the life of the user that may be able to refine a forecasting method.

As mentioned above, there may be benefits to predicting glucose states for patients in an ICU setting, who have their blood glucose levels measured periodically, and typically with a finger prick and tested on a glucose meter, a process which may take 10 minutes to complete. Each result is thus roughly 10 minutes delayed. Being able to predict blood glucose levels could be incredibly helpful in an ICU setting, both from a patient care as well as hospital resource management perspective. ICU patients typically already have EEG electrodes attached, and thus brain activity data can be sensed and analyzed to forecast (or help forecast) future blood glucose levels. Any of the methods and systems described herein may thus advantageously be used in an ICU setting. Currently, insulin drips are typically provided to ICU patients, with a sliding scale of dosage as part of the current care. Management of glucose states could thus be incorporated into the ICU as well, concepts of which are described herein.

Additionally, the systems herein may be beneficial to individuals who are prediabetic and may want to benefit from being informed of their future predicted glucose levels or existing glucose levels. Additionally still, the concepts herein may be useful for subject's who may otherwise be considered healthy, and who simply want more information about their body, their health, and their overall well-being. For example, without limitation, athletes may benefit from wearing a brain activity signals sensor at one more discrete locations on the scalp and have an App that can inform them when it would be a good time to ingest carbohydrates if future blood glucose levels are predicted to start to drop just prior to the start of an athletic event, for example. Because the App may be adapted to predict future glucose levels, they may know 1-2 hours before an athletic event when an optimal or preferred time might be to ingest one or more certain types of food. An additional exemplary scenario is to check the App just prior to the start of the athletic event to check if a predicted low glucose level might occur during the event, and in that case could drink a sugary drink in advance of the low level, including at an optimal time. Additionally, since the Apps may be adapted to predict future levels, the athlete could take the wearable sensor off before the game and already be armed with the knowledge about the future glucose levels with the App by the time the athletic event begins. For example, the subject may remove the sensor, but the App can be configured to track previous predicted states, and continue to show the time when predicted levels are predicted to occur.

In this regard, one aspect of the disclosure is an App that can utilize extra-cranially sensed brain activity signals and provide information indicative of a subject's predicted glucose levels or risk levels when the subject is not even wearing a wearable brain activity signal sensor, and when they are optionally not even wearing any type of glucose monitor. Any other feature in this disclosure may be incorporated into this aspect.

Systems herein optionally include an online portal (Examples of which are shown in FIGS. 21A and 21B), which is optionally available to the subject and any other individual approved by the user (e.g. physician, caregiver, care team, family member, etc.). The portal may be adapted to display any of the information or data described herein, including any historical data on blood glucose trends and user insights on blood glucose levels. The portal may optionally be adapted to display raw EEG signals. The online portal may have signal processing and/or analyzing capabilities as well.

As a mere example, an online portal may comprise any of the following functionality or capabilities: communicates the actual and forecast of future glucose levels to patient/ care team; communicates a trend of past glucose measurements; communicates insulin and medication information to user based on real-time and forecasted blood glucose: provides alerts when glucose is trending out of range or is out of range: provides user with long-term (e.g., 10+ hour) forecast of "risk states" to suggest optimal times of day to exercise, eat meals, and take medication based on the glucose forecast; adapted to displays outside insulin pump, glucose monitor, and App information from Bluetooth linked systems; adapted to displays raw EEG tracing, with user-input markers; can display any other related health data.

As described herein, systems, devices, and methods herein may be adapted to be incorporated and used to some extent with existing glucose monitors, such as CGMs, invasive glucose monitors, and non-invasive optical glucose monitors, and/or their methods of use. For example, existing CGMs may be modified and adapted to incorporate sensed EEG data (for example only, any sensing concepts/methods in U.S. Pat. No. 6,572,542 and/or U.S. Pat. No. 8,118,741) and/or forecasting concepts herein to improve performance. For example only, CGM sensed data can be analyzed with patient EEG data, and the predictive EEG data can train the glucose data (e.g., ISG data), so that the CGM may then be adapted to use ISG readings to better predict future blood glucose states, exemplary method steps of which are shown in FIG. 49, and which may be combined with any other suitable method step herein. For example, a certain pattern of EEG-trained ISG data (readings well before an impending event) can then be used to predict a future glycemic event. It is thus understood that any existing CGM may be modified and adapted to incorporate any of the features or methods herein. For example, a CGM can be adapted to communicate with an App and make an alert that a subject should prepare to drink a sugary drink in a certain period of time, such as 1 hour in the future, or that a hypoglycemic event is likely to occur 2.5 hours in the future. Additionally, for example, a CGM could be modified to deliver insulin at a time much earlier than with previous technologies, and could deliver longer lasting insulin well in advance of a hyperglycemic event. FIG. 50 illustrates merely exemplary method steps in which sensed ISG levels can be used to manage a future glucose state of a subject.

FIG. 51 illustrates merely exemplary steps that may be included in a method of training ISG data with EEG data, which may be performed to allow a glucose monitor to sense ISG and 1) forecast information indicative of a future glucose state (e.g., FIG. 49) and/or 2) facilitate the management of a future glucose state (e.g., FIG. 50).

Additionally, and only for example, any of the EEG data and methods herein may optionally be used to help calibrate and/or recalibrate glucose monitors (e.g., CGMs) (which need recalibrating over time), which could avoid the need to use glucose meters and finger pricks to re-calibrate glucose monitors such as CGMs. FIG. 52 illustrates a merely exemplary method of calibrating or recalibrating a glucose monitor, optionally a CGM, comprising: calibrating or recalibrating a glucose monitor using at least one of EEG data sensed from the subject or information indicative of the EEG data sensed from the subject. Additionally, glucose monitors (e.g., CGMs) and/or glucose meters may similarly be used to calibrate any of the EEG forecasting methods (e.g., algorithms) herein, an example of which is shown in FIG. 53.

As described in more detail herein, however, it is conceivable that forecasting may occur without sensing any EEG data. For example, if a CGM is trained on sensed EEG data, existing CGMs may optionally be modified to be adapted with a trained model to forecast future glucose levels and/or risk indicators based on the existing process of sensing ISG levels. Additionally and for example, one or more biosignals (with or without EEG data) may be sensed/obtained and analyzed as part of the prediction process, such as, without limitation, heart rate (HR), heart rate variability, skin conductance, blood pressure, body temperature, exercise level, etc.

Figure 54:
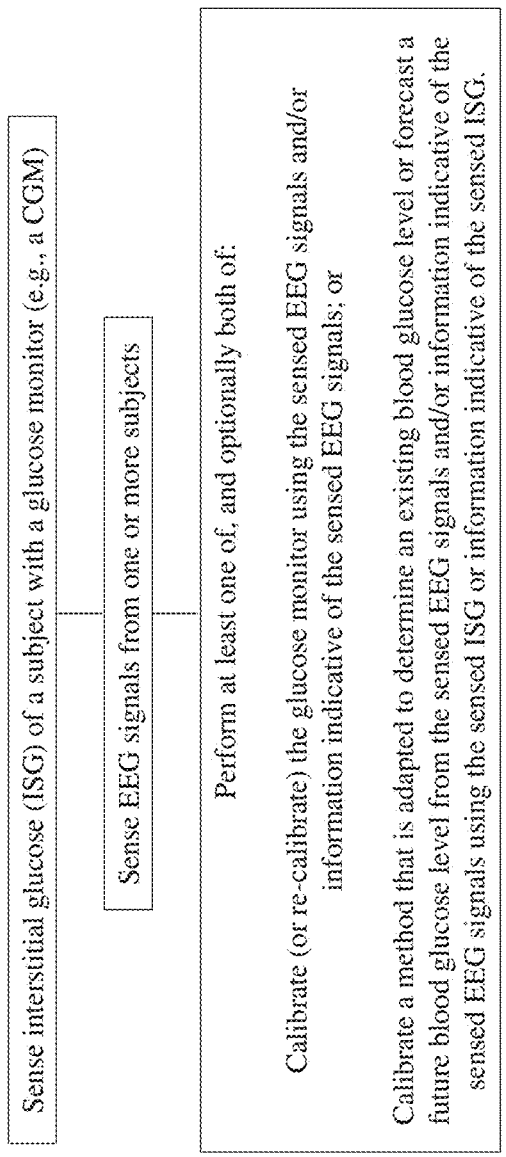
FIG. 54 illustrates an exemplary method of using ISG data and EEG data to perform at least one calibration process.

One aspect of the disclosure is an optional bi-directional calibration method and/or system, an example of which is shown in FIG. 54. In one example, a bi-directional calibration method may include sensing interstitial glucose of a subject with a glucose monitor, optionally a CGM; sensing EEG signals from one or more subjects, optionally with any of the wearable devices herein; and performing at least one of, and optionally both of: calibrating (or re-calibrating) the glucose monitor using the sensed EEG signals and/or information indicative of the sensed EEG signals; or calibrating a method that is adapted to determine an existing blood glucose level or forecast a future blood glucose level from the sensed EEG signals and/or information indicative of the sensed EEG signals using the sensed ISG or information indicative of the sensed ISG.

Additionally, as mentioned above, thresholds for CGMs are currently reset (when they need to be reset) at an office visit. Sensing EEG data and utilizing the forecasting aspects herein may even allow for resetting thresholds without requiring an office visit, such as by using an online portal.

Additionally, CGMs can be used in conjunction with any of the other heath data/biosignals (e.g., user inputs) herein (e.g., heart rate, blood pressure, skin conductance-which can be sensed easily by existing devices such as smartwatches, fitbits, etc.) or any of the wearable brain activity sensors herein to optionally predict future glucose states.

Exemplary CGMs, features and methods of use of which may be incorporated herein include those by Dexcom (e.g., G6 CGM System), Medtronic (e.g., Guardian™ Connect), Abbott (e.g., any FreeStyle Libre), and the Eversense® E3 CGM. Exemplary Glucose Meters (glucometers), features and methods of use of which may be incorporated herein: LifeScan OneTouch®, Accu-Chek®, and FreeStyle Lite by Abbott. Exemplary Insulin pumps, features and methods of use of which may be incorporated herein: Medtronic Minimed™, Pumps from Tandem, and Omnipod® pumps.

Any example, method, system, device or other aspect from any of the disclosure herein may be combined with any other portion of this disclosure unless it is expressly stated otherwise herein.

Even if not specifically indicated, one or more methods or techniques described in this disclosure (e.g. any of the computer executable methods) may be implemented, at least in part, in hardware, software, firmware or any combination thereof. For example, various aspects of the techniques or components may be implemented within one or more processors, including one or more microprocessors, digital signal processors (DSPs), application specific integrated circuits (ASICs), field programmable gate arrays (FPGAs), programmable logic circuitry, or the like, either alone or in any suitable combination. The term "processor" or "processing circuitry" may generally refer to any of the forego-ing circuitry, alone or in combination with other circuitry, or any other equivalent circuitry.

Such hardware, software, or firmware may be implemented within one device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read only memory (ROM), non-volatile RAM (NVRAM), electrically erasable programmable ROM (EEPROM), Flash memory, and the like. The instructions may be executed by a processor to support one or more aspects of the functionality described in this disclosure.

Figure 48:
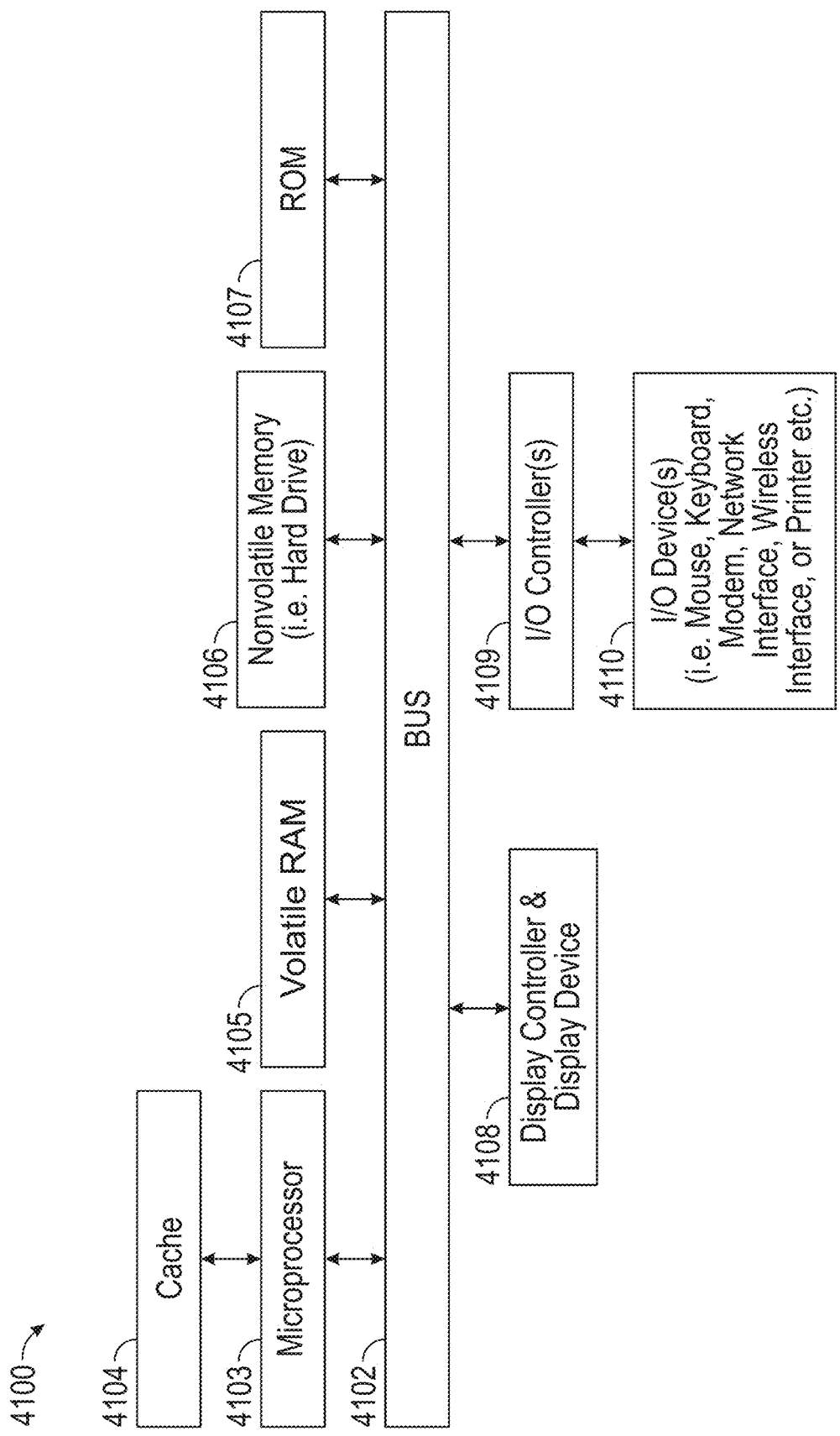
FIG. 48 is a merely exemplary block diagram of an exemplary data processing systems, any part or all of which may be used with any embodiments of any of the inventions or embodiments set forth herein.

FIG. 48 is a merely exemplary block diagram of an exemplary data processing system, any part or all of which may be used with any embodiments of any of the inventions or embodiments set forth herein. Also note that one or more of the components shown in FIG. 48 may be optional even if it is not stated as such herein. Note that while FIG. 48 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components, or perhaps more components may also be used with the present invention.

As shown in FIG. 48, exemplary computer system 4100, which is a form of a data processing system, includes a bus or interconnect 4102 which is coupled to one or more microprocessors 4103 and a ROM 4107, a volatile 41M 3505, and a non-volatile memory 4106. The microprocessor 4103 is coupled to cache memory 4104. The bus 4102 interconnects these various components together and also interconnects these components 4103, 4107, 4105, and 4106 to a display controller and display device 4108, as well as to optional input/output (I/O) devices 4110, which may be mice, keyboards, modems, network interfaces, printers, and other devices.

Typically, the input/output devices 4110 are coupled to the system through input/output controllers 4109. The volatile RAM 4105 is typically implemented as dynamic RAM (DRAM) which requires power continuously in order to refresh or maintain the data in the memory. The non-volatile memory 4106 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 48 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 4102 may include one or more buses connected to each other through various bridges, controllers, and/or adapters, as is well-known in the art. In one embodiment, the I/O controller 4109 includes a USB (Universal Serial Bus) adapter for controlling USB peripherals. Alternatively, I/O controller 4109 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology. Wireless communication protocols may include Wi-Fi, Bluetooth, ZigBee, near-field, cellular and other protocols.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures herein can be implemented using code (e.g., computer executable methods, algorithms) and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

ADDITIONAL EXAMPLES

One or more aspects from any from any of the following examples may be combined or interchanged with any other additional example unless indicated to the contrary. If an additional example is a device or system, it can be adapted to perform a method step from any of the method additional example. If an additional example is a method, it can be adapted with a device and/or system from a different additional example. Additionally, any aspect of this disclosure may be integrated into one or more of these additional examples.

A first additional example comprises a method of predicting a glucose state. The glucose state is optionally a real-time or future glucose state.

This example may include non-invasively sensing one or more brain activity signals with a wearable sensor adapted to wirelessly communicate sensed brain activity signals to a second device in wireless communication with the wearable sensor. The sensor is optionally adapted to sense single channel or dual channel signals, optionally with two sensing electrodes and a third ground electrode.

This example may include inputting the sensed brain activity signals or processed single-channel brain activity signals into a method trained to predict a glucose state of the subject based at least partially on the sensed brain activity signals or the processed brain activity signals.

This example may include predicting, using the trained model, one or more predicted glucose states of the subject that is based at least partially on the sensed brain activity signals or the processed brain activity signals.

In this example, predicting the predicted glucose state may comprise detecting a change in power over time, optionally only in a subset of frequencies within a larger range from 0 to 50 Hz.

This example may include outputting instructions to initiate a communication with the second device, the communication indicative of the one or more predicted glucose states based on and in response to the predicted glucose state. A communication may include information to a subject about the predicted glucose state (e.g., predicted blood glucose values), such as visual information on a display of a device.

This example may include one or more recommendations for action, such as at least one of when to exercise or when to consume a meal.

In this example, predicting the predicted glucose state may comprise using brain activity signals from only a subset of frequencies from within a larger range of frequencies including a delta band, a theta band, an alpha band, a beta band, and a gamma band, or only a subset of frequencies from within a larger range of frequencies from 0-50 Hz.

In this example, inputting sensed brain activity signals or processed brain activity signals into a trained model may include inputting only a subset of frequencies from within the larger range of frequencies including the delta band, the theta band, the alpha band, the beta band, and the gamma band, or inputting only a subset of frequencies from within the larger range of frequencies from 0 to 50 Hz.

This example may include filtering out, using any technique and using any of the devices herein, sensed brain activity signals that are within one or more of the delta band, the theta band, the alpha band, the beta band, or the gamma band.

This example may include predicting real-time blood glucose values or future glucose states.

In this example, a trained model may be trained on at least personal non-invasively sensed brain activity signals optionally from at least one behind the ear location and/or at least one of an O1 and O2 location (on a standard 10-20 EEG setup), and on personal glucose values of the subject.

In this example, a subset of frequencies may include one or more frequencies within the beta and gamma bands, and it may exclude frequencies within the delta, theta, and alpha bands.

In this example, a subset of frequencies may include one or more frequencies within the delta, theta, and alpha bands, and exclude frequencies in the beta and gamma bands.

In this example, predicting a predicted glucose state optionally comprises predicting one or more aspects of a prandial event, such as a post-prandial even. One or more aspects of a prandial event may comprise at least one of a glucose value at a post-prandial glucose peak, or an epoch of time until a post-prandial peak in glucose value is predicted to occur. Predicting a post-prandial event may comprise predicting a post-prandial event from 5 min-90 minutes before the post-prandial event.

In this example, non-invasively sensing may comprise using a wearable sensor that includes a ground electrode, the ground electrode spaced from a nearest of first and second sensing electrodes at a distance that is greater than a nearest distance between the first and second sensing electrodes.

In this example, a trained model may be trained on glucose values estimated using one or more of a continuous glucose monitor adapted to sense ISF, an implantable glucose sensor, finger prick measurements, or other non-invasive wearable continuous glucose monitor.

In this example, one or more wearable sensors can be worn on one or more head locations, including one or more behind the ear locations, or at least one of an O1 or O2 location, including any combination thereof.

A second additional example is a system adapted for predicting a glucose state of a subject.

In this example, the system optionally includes at least one wearable non-invasive brain activity signal sensor. In this example, one or more wearable sensors may include first and second sensing electrodes, and optionally a third ground or referential electrode. In this example, one or more wearable sensors may be worn at on one or more head locations, including one or more behind the ear locations, or at least one of an O1 or O2 location, including any combination thereof. In this example a wearable sensor may include one or more communication components or modules for wireless communication brain signals to a second device.

In this example, the system may include a second device (optionally a subject or care-team device) configured to receive information wirelessly from one or more wearable sensors. A second device may include one or more processors and a memory coupled to the one or more processors. The memory can store computer-program instructions, that, when executed by the one or more processors, causes the performance of predicting, using a trained prediction model, a predicted glucose state of the subject that is based at least partially on sensed brain activity signals or processed brain activity signals, and outputting instructions to initiate a communication indicative of the predicted glucose state based on and in response to the predicted glucose state. The instructions can also cause the performance of receiving sensed brain activity signals or processed brain activity signals sensed by one or more wearable non-invasive brain activity sensors.

In this example, one or more wearable sensors may include a power source (optionally rechargeable) and one or more processing components.

In this second additional example, predicting the predicted glucose state may include any aspect of any of the glucose state prediction methods herein.

A third additional example is a computer-executable method, stored in a non-transitory media, adapted to, when executed by one or more processors, cause the performance of predicting a predicted glucose state of the subject that is based at least partially on sensed brain activity signals or processed brain activity signals, and output instructions to initiate a communication indicative of the predicted glucose state based on and in response to the predicted glucose state.

This third additional example may include any other aspect of the disclosure herein.

A fourth additional example is a method of identifying a predictive aspect of future blood glucose levels for one or more subjects, comprising receiving glucose levels of the subject using a glucose monitor; receiving brain activity (EEG) signals non-invasively sensed with one or more sensors on the scalp of a subject; determining a temporal lag associated with a relatively higher correlation between one or more features of the brain activity signals and glucose levels; and providing a trained model executable by one or more processors that, when receiving subsequent brain signals, is adapted to predict glucose levels and that predicts glucose levels a time in advance that includes the determined temporal lag.

This fourth additional example may include any other aspect of the disclosure herein.

A fifth additional example is a method of identifying a predictive aspect of future blood glucose levels for a plurality of subjects, comprising: for a first subject, determining a first temporal lag associated with a relatively higher correlation between one or more features of the brain activity signals of the first subject and glucose levels of the first subject; for a second subject, determining a second temporal lag associated with a relatively higher correlation between one or more features of the brain activity signals of the second subject and glucose levels of the second subject; providing a trained model executable by one or more processors that, when receiving subsequent brain signals, is adapted to predict glucose levels and that predicts glucose levels a time in advance that includes the first determined temporal lag; and providing a trained model executable by one or more processors that, when receiving subsequent brain signals, is adapted to predict glucose levels and that predicts glucose levels a time in advance that includes the second determined temporal lag.

This fifth additional example may include any other aspect of the disclosure herein.

A sixth additional example is a method of predicting blood glucose levels of a subject, comprising: sensing brain activity signals of a subject during an epoch of awake time and during an epoch of asleep time; and predicting blood glucose levels of the subject, wherein predicting during the awake time relies more heavily on one or more features of the brain signals than when predicting during the sleep time, and wherein predicting during the sleep time relies more heavily on one or more features of the brain signals than when predicting during the awake time.

This sixth additional example may include any other aspect of the disclosure herein.

A seventh additional example is method of monitoring blood glucose levels of a subject while the subject is asleep, comprising: extracranially sensing brain activity signals of a subject while the subject is asleep; obtaining sensed glucose levels with a glucose monitor from worn by the subject while the subject is asleep; and predicting or estimating blood glucose levels while the subject is asleep using the sensed brain activity signals and the sensed glucose levels.

This seventh additional example may include any other aspect of the disclosure herein.

An eighth additional example is a computer-executable method, stored in a non-transitory media, adapted to, when executed by one or more processors, cause the performance of: receiving as input extracranially-sensed EEG data or information indicative of extracranially-sensed EEG from a subject; and creating a visual representation of, on a display of a device, a predicted glucose state based at least partially on the EEG data.

This eighth additional example may include any other aspect of the disclosure herein.

A ninth additional example is a method of training an EEG blood glucose prediction algorithm; comprising: obtaining or receiving an indicator of consumption by a subject; receiving or generating blood glucose measurements from the subject (optionally with a CGM); receiving or generating EEG data from the subject; and identifying one or more features of sensed EEG data from the subject that is predictive of a prandial event.

This ninth additional example may include any other aspect of the disclosure herein.

A tenth additional example is a method of estimating blood glucose levels in a subject, comprising: sensing blood glucose levels of a subject, optionally with a continuous glucose monitor or sensor; sensing EEG data from the subject; and estimating blood glucose levels using at least the sensed EEG data.

This tenth additional example may include any other aspect of the disclosure herein.

An eleventh additional example is a computer-executable trained method for predicting a glucose state of a subject, stored in a non-transitory media on a computing device, the trained method adapted to, when executed by a processor, cause the performance of: receive brain activity signals or processed brain activity signals sensed by a wearable non-invasive brain activity sensor; predict a glucose state of the subject based at least partially on the brain activity signals or processed brain activity signals; and initiate an output adapted to communicate information indicative of the predicted glucose state.

This eleventh additional example may include any other aspect of the disclosure herein.

A twelfth additional example is a method of training a prediction model to predict a glucose state of a subject, comprising: providing or receiving non-invasively sensed brain activity signals; providing or receiving sensed glucose level data from the subject; and identifying one of more features of the non-invasively sensed brain activity signals that have a relatively higher correlation with at least some of the one or more sensed glucose level data to train the prediction model with the one or more features and the glucose state, wherein the trained prediction model is adapted to receive as input subsequent non-invasively sensed brain activity signals and predict a predicted glucose state of the subject based on at least the subsequent non-invasively sensed brain activity signals.

This twelfth additional example may include any other aspect of the disclosure herein.

A thirteenth additional example is a method of predicting a glucose state of a subject, comprising: non-invasively sensing brain activity signals using one or more electrodes on a scalp of a subject; inputting the brain activity signals or processed brain activity signals into a trained computer executable model trained to predict a future glucose state of the subject; predicting a predicted future glucose state of the subject using the trained model and based at least partially on the non-invasively sensed brain activity signals or processed brain activity signals, wherein predicting the future glucose state comprises using a personalized temporal lag epoch of time determined for the subject to have a prediction accuracy relatively greater than other epochs of time; and outputting instructions to initiate a communication indicative of the predicted future glucose state based on and in response to the predicted future glucose state.

This thirteenth additional example may include any other aspect of the disclosure herein.

A fourteenth additional example is a method of predicting a glucose state of a subject, comprising: non-invasively sensing brain activity signals using a wearable sensor with a communication module adapted for wireless communication during a sleep time of the subject; inputting the brain activity signals or processed brain activity signals into a trained model trained to predict a glucose state of the subject during the sleep-time; predicting a predicted glucose state of the subject using the trained model and based at least partially on the non-invasively sensed brain activity signals or processed brain activity signals; and outputting instructions to initiate a communication indicative of the predicted glucose state based on and in response to the predicted glucose state.

This fourteenth additional example may include any other aspect of the disclosure herein.

A fifteenth additional example is a method of predicting a real-time or future glucose level of a subject in a subject, comprising: sensing glucose levels from a subject with a glucose monitor; non-invasively sensing brain activity signals from the subject; and predicting a real-time or future glucose level of the subject based at least on the non-invasively sensed brain activity signals from the subject; and outputting instructions to initiate a communication indicative of the predicted glucose level.

This fifteenth additional example may include any other aspect of the disclosure herein.

A sixteenth additional example is a method of calibrating a glucose monitor worn by a subject, comprising: sensing glucose levels from a subject with the glucose monitor; non-invasively sensing brain activity signals from the subject contemporaneously while sensing glucose levels; predicting a predicted glucose level of the subject based on the non-invasively sensed brain activity signals; and calibrating the glucose monitor based at least on the predicted glucose level.

This sixteenth additional example may include any other aspect of the disclosure herein.

A seventeenth additional example is a wearable brain activity signal sensor sized and configured to be worn by a subject.

In this example, the sensor optionally includes a flexible electrode housing. A flexible electrode housing optionally has a skin-facing surface.

In this example, the sensor may optionally include first and second sending electrodes secured to the optional flexible electrode housing and each having a skin facing surface.

In this example, the sensor may optionally further comprise an adhesive layer disposed on at least a portion of a skin-facing surface of the sensor. An adhesive layer may be positioned to contact skin when the sensor is worn by the subject.

In this example, the sensor may optionally include first and second sensing electrodes and optionally a ground electrode spaced apart from first and second sensing electrodes.

In this example, a skin-facing surface of the sensor may optionally be concave in at least a portion of the skin-facing surface.

In this example, the sensor may optionally include an electronics member that is configured and sized to be releasably coupled with an electrode housing. An electronics member optionally includes a plurality of electrode couplers each sized and positioned to be placed in electrical communication with one of first and second electrodes when the electronics member is coupled with the electrode housing.

In this example, the sensor may optionally include a wireless communication module, such as Bluetooth. A communication module may be embedded within an optionally flexible electrode housing.

In this example, the sensor may optionally include a processor, optionally embedded within a flexible electrode housing, wherein a processor may be in communication with a plurality of electrode in the sensor.

In this example, the sensor optionally may include a flexible electrode housing, the flexible electrode housing having a skin-facing surface, the flexible electrode housing flexible to facilitate conformability between the sensor and the subject's skin; only one pair of first and second sensing electrodes secured to the flexible electrode housing and spaced apart at a first distance therebetween; and a ground electrode secured to the flexible electrode housing and spaced from the first and second sensing electrodes, the ground electrode spaced from a nearest of the first and second sensing electrodes at a second distance greater than the first distance, the first and second sensing electrodes and the ground electrode each having skin-facing surfaces, the sensor configured to operate in a monopolar sensing mode between each of the first and second sensing electrodes and the ground electrode, and in a bipolar sensing mode between the first and second sensing electrodes.

In this example, a first distance between sensing electrodes is optionally from 1 mm and 8 mm.

In this example, a second distance between a ground electrode and a nearest sensing electrode is optionally from 8 mm to 35 mm.

In this example, the sensor optionally includes an electronics member configured and sized to be releasably coupled with an electrode housing, an electronics member including a plurality of electrode couplers each sized and positioned to be placed in electrical communication with an electrode when the electronics member is coupled with an electrode housing.

In this example, an optional electronics member optionally has a length less than a length of an electrode housing.

In this example, an optional electronics member optionally has a length from 10 mm to 50 mm.

In this example, an optional electronics member optionally has a width less than a width of the flexible electrode housing.

In this example, an optional electronics member optionally comprises a processor and a communications module, the processor arranged to be in communication with a first sensing electrode, a second sensing electrode, and a ground electrode when the electronics member is coupled with an electrode housing, optionally wherein an electronics member further comprises a power source, optionally rechargeable.

In this example, at least a portion of a sensor skin-facing surface, optionally of an electrode housing, is optionally concave.

In this example, a sensor may further comprise an adhesive layer disposed on at least a portion of the skin-facing surface, an adhesive layer positioned to contact skin when the sensor is worn by the subject.

In this example, a sensor may further comprise a processor and a communications module embedded within an optional flexible electrode housing, the processor optionally in communication with a first sensing electrode, a second sensing electrode, and a ground electrode.

In this example, the sensor optionally has a length from 15 mm to 60 mm, optionally a width from 5 mm to 30 mm, and optionally a height from 1 mm to 10 mm.

In this example, the sensor optionally has a length from 15 mm to 60 mm.

In this example, the sensor optionally has a width from 5 mm to 30 mm.

In this example, the sensor optionally has a height from 1 mm to 10 mm.

In this example, the sensor is optionally sized and configured to be worn at a behind the ear location (optionally M1, M2, A1 or A2 in some figures herein).

In this example, the sensor is optionally sized and configured to be worn on a region of a subject that is not visible when viewing the face of the subject.

In this example, a plurality of electrodes, including an optional ground electrode, are optionally aligned along a length of an electrode housing.

In this example, the sensor optionally further includes one or more additional types of biosignal sensors, optionally such as one or more of an inertial sensor, an electrodermal activity sensor, or a photoplethysmography sensor.

In this example, the sensor optionally is adapted to provide a vibratory alert to the wearer.

This seventeenth additional example may include any other aspect of the disclosure herein.

An eighteenth additional example is method of manufacturing a wearable sensor, comprising: providing a plurality of electrodes including first and second electrodes each having skin-facing surfaces; and forming a flexible overmold disposed partially about the first and second electrodes to secure the relative positions of the plurality of electrodes relative to each other, and wherein the skin-facing surfaces of each of the plurality of electrodes are positioned to face skin.

This eighteenth additional example may include any other aspect of the disclosure herein.

A nineteenth additional example is a package including a plurality of wearable brain activity sensors therein, each adapted to be adhered to a subject to sense brain activity signals, each of the plurality of wearable brain activity sensors comprising: a flexible electrode housing with a skin-facing surface, and a plurality of electrodes secured to the flexible electrode housing, wherein each of the plurality of electrodes has at least one exposed surface, each of the flexible electrode housings sized and configured to be releasably coupled to an electronics member to facilitate electrical communication between each of the exposed surfaces of the plurality of electrodes and a processor of the electronics member.

This nineteenth additional example may include any other aspect of the disclosure herein.

A twentieth additional example is a package including a plurality of wearable brain activity sensors therein, each adapted to be adhered to a subject to sense brain activity signals, each of the plurality of wearable brain activity sensors comprising: an electrode housing with a skin-facing surface, and a plurality of electrodes secured to the flexible electrode housing, wherein each of the plurality of electrodes has at least one exposed surface, each of the flexible electrode housings sized and configured to be releasably coupled to an electronics member to facilitate electrical communication between each of the at least one exposed surface of the plurality of electrodes and a processor of the electronics member.

This twentieth additional example may include any other aspect of the disclosure herein.

It is understood that any device, component, system, and/or method step of this Detailed Description may be combined with any other suitably combinable device, component, system, and/or method step of this Detailed Description.

The invention claimed is:

1. A system adapted for predicting a glucose state of a subject, comprising:
   a wearable non-invasive brain activity signal sensor ("wearable sensor") that includes sensing electrodes consisting of first and second sensing electrodes and a third reference electrode and adapted for single channel or dual channel sensing, the wearable sensor sized and configured to be secured at a behind the ear location and on skin of a subject, the wearable sensor including a wireless communication component, a power source and one or more processing components;
   a subject device configured to receive information wirelessly from the wearable sensor, the subject device including:
   one or more processors;
   a memory coupled to the one or more processors, the memory storing computer-program instructions, that, when executed by the one or more processors, cause the performance of:
      receiving or generating sensed brain activity signals or processed brain activity signals sensed by the wearable non-invasive brain activity sensor;
      predicting, using a trained prediction model, a predicted glucose state of the subject that is based at least partially on the sensed brain activity signals or the processed brain activity signals,
         wherein predicting the predicted glucose state comprises predicting based on at least brain activity data from only a subset of frequencies within a larger range of frequencies that includes a delta band, a theta band, an alpha band, a beta band, and a gamma band, and
         wherein predicting the predicted glucose state further comprises predicting the glucose state at one or more future epochs of time, wherein the one or more future epochs of time comprise a personal future epoch of time for the subject that has greater predictive accuracy of glucose state than other future epochs of time for the subject; and
      outputting instructions to initiate a communication indicative of the predicted glucose state based on and in response to the predicted glucose state.

2. The system of claim 1, wherein the system is further configured to filter out sensed brain activity signals that are within one or more of the delta band, the theta band, the alpha band, the beta band, or the gamma band, that are outside of the subset of frequencies.

3. The system of claim 2, wherein the wearable sensor includes one or more filtering components to filter out frequencies outside of the subset of frequencies.

4. The system of claim 2, wherein the subject device includes one or more filtering components to filter out frequencies outside of the subset of frequencies.

5. The system of claim 1, wherein predicting the predicted glucose state further comprises predicting real-time blood glucose values.

6. The system of claim 5, wherein predicting real-time blood glucose values comprises predicting the real-time blood glucose values while the subject is asleep.

7. The system of claim 6, wherein the computer-program instructions further cause the performance of comparing the predicted real time glucose values to sensed glucose values sensed from a continuous glucose monitor adapted to sense interstitial glucose and worn by the subject at a location different than the wearable sensor while the subject is asleep, and initiate instructions to cause the continuous glucose monitor to be calibrated based on the predicted real time glucose values.

8. The system of claim 1, wherein predicting glucose values comprises predicting glucose values from 15 minutes to 13 hours from when the non-invasively sensed brain activity signals were sensed by the wearable sensor.

9. The system of claim 1, wherein a personalized lag time has an accuracy of at least 90% accuracy for the subject.

10. The system of claim 1, wherein the subset of frequencies includes one or more frequencies within the beta and gamma bands, and wherein the subset excludes frequencies within the delta, theta, and alpha bands.

11. The method of claim 1, wherein the subset of frequencies includes one or more frequencies within the delta, theta, and alpha bands, and wherein the subset excludes frequencies within the gamma and beta bands.

12. The system of claim 1, wherein predicting the predicted glucose state comprises predicting one or more aspects of a post-prandial event.

13. The system of claim 12, wherein the one or more aspects of the post-prandial event comprises at least one of a glucose value at a post-prandial glucose peak, or an epoch of time until a post-prandial peak in glucose value is predicted to occur.

14. The system of claim 12, wherein predicting the one or more aspects of the post-prandial event comprises predicting the one or more aspects of the post-prandial event from 5 min-90 minutes before the post-prandial event.

15. The system of claim 1, wherein predicting the predicted glucose state further comprises,
   predicting a real-time glucose state while the subject is asleep, and
   while the subject is awake, predicting the glucose state at the one or more future epochs of time.

16. The system of claim 1, wherein the predicted glucose state is one of a predicted blood glucose level or a predicted interstitial glucose level.

17. The system of claim 1, wherein predicting the predicted glucose state comprises detecting a change in power over time in the subset of frequencies.

18. The system of claim 1, wherein the trained model is a model trained on personal non-invasively sensed brain activity signals from a behind the ear location and on glucose values estimated using one or more of a continuous glucose monitor adapted to sense interstitial fluid glucose, an implantable glucose sensor, finger prick blood measurements, or a non-invasive wearable glucose monitor adapted to monitor glucose.

19. The system of claim 1, wherein the computer-program instructions are adapted to train the trained prediction model, comprising:
   receiving or generating the sensed brain activity signals or processed brain activity signals sensed by the wearable sensor;

providing or receiving personal sensed glucose data from a glucose monitor worn by the subject; and based on the sensed brain activity signals or processed brain activity signals, and the personal sensed glucose data from the glucose monitor, identifying or determining the one or more future epochs of time for the subject that have greater predictive accuracy of glucose state than other future epochs of time for the subject.

20. A system adapted for predicting a glucose state of a subject, comprising:

a wearable non-invasive brain activity signal sensor ("wearable sensor") that includes sensing electrodes consisting of first and second sensing electrodes and a third reference electrode and adapted for single channel or dual channel sensing, the wearable sensor sized and configured to be secured at a behind the ear location and on skin of a subject, the wearable sensor including a wireless communication component, a power source and one or more processing components;

a subject device configured to receive information wirelessly from the wearable sensor, the subject device including:

one or more processors;

a memory coupled to the one or more processors, the memory storing computer-program instructions, that, when executed by the one or more processors, causes the performance of:

receiving or generating sensed brain activity signals or processed brain activity signals sensed by the wearable sensor;

predicting, using a trained prediction model, a predicted glucose state of the subject that is based at least partially on the sensed brain activity signals or the processed brain activity signals, wherein predicting the predicted glucose state comprises predicting based on at least brain activity data from only a subset of frequencies within a larger range of frequencies that includes a delta band, a theta band, an alpha band, a beta band, and a gamma band, and wherein predicting the predicted glucose state comprises at least one of, predicting the glucose state at one or more future epochs of time that comprise a personal future epoch of time that has have greater predictive accuracy of glucose state for the subject than other future epochs of time for the subject, predicting the glucose state with brain activity signals or processed brain activity signals from one or more personal wearable sensor locations on the subject's head that have greater predictive accuracy of the glucose state for the subject when the wearable sensor is properly worn than other wearable sensor locations on the subject's head when the wearable sensor is properly worn, or predicting the glucose state with one or more brain signal frequencies that comprise personal brain signal frequencies that have greater predictive accuracy of glucose state for the subject than other brain signal frequencies; and outputting instructions to initiate a communication indicative of the predicted glucose state based on and in response to the predicted glucose state.

21. The system of claim 20, wherein the computer-program instructions are adapted to further cause the performance of, in response to an on-demand glucose state prediction request that follows a period that is free of predicting a glucose state based on the sensed brain activity signals or the processed brain activity signals, predicting the predicted glucose state of the subject, wherein the on-demand glucose state prediction request is communicated by the subject to the subject device.

22. The system of claim 20, wherein the computer-program instructions are adapted to train the trained prediction model, comprising:

receiving or generating the sensed brain activity signals or processed brain activity signals sensed by the wearable sensor;

providing or receiving personal sensed glucose data from a glucose monitor worn by the subject; and based on the sensed brain activity signals or processed brain activity signals, and the personal sensed glucose data from the glucose monitor, performing at least one of identifying or determining the one or more personal future epochs of time that have greater predictive accuracy of glucose state than other future epochs of time for the subject, identifying or determining the one or more personal wearable sensor locations on the subject's head that have greater predictive accuracy of the glucose state for the subject than other wearable sensor locations on the subject's head when the wearable sensor is properly worn, or identifying or determining the personal brain signal frequencies that have greater predictive accuracy of glucose state for the subject than other brain signal frequencies.

23. The system of claim 20, wherein the computer-program instructions further cause the performance of comparing the predicted glucose state to sensed glucose values sensed from a continuous glucose monitor adapted to sense interstitial glucose and worn by the subject at a location different than the wearable sensor, and initiate instructions to cause the continuous glucose monitor to be calibrated based on the predicted glucose state.

24. A system adapted for predicting a glucose state of a subject, comprising:

a wearable non-invasive brain activity signal sensor ("wearable sensor") that includes a plurality of sensing electrodes and a reference electrode, the wearable sensor sized and configured to be secured at a behind the ear location and on skin of a subject, the wearable sensor including a wireless communication component, a power source and one or more processing components;

a subject device configured to receive information wirelessly from the wearable sensor, the subject device including:

one or more processors;

a memory coupled to the one or more processors, the memory storing computer-program instructions, that, when executed by the one or more processors, cause the performance of:

receiving or generating sensed brain activity signals or processed brain activity signals sensed by the wearable sensor;

predicting, using a trained prediction model, a predicted glucose state of the subject that is based at least partially on the sensed brain activity signals or the processed brain activity signals, wherein predicting the predicted glucose state comprises predicting based on at least brain activity data from only a subset of frequencies within a larger range of frequencies that includes a delta band, a theta band, an alpha band, a beta band, and a gamma band, and wherein predicting the predicted glucose state further comprises predicting the glucose state at one or more future epochs of time, wherein the one or more future epochs of time comprise a personal future epoch of time for the subject that has greater predictive accuracy of glucose state than other future epochs of time for the subject; and outputting instructions to initiate a communication indicative of the predicted glucose state based on and in response to the predicted glucose state.

25. The system of claim 24, wherein the trained model is a model trained on at least personal non-invasively sensed brain activity signals from a behind the ear location and on personal glucose values of the subject.

26. The system of claim 24, wherein predicting the predicted glucose state further comprises predicting real-time blood glucose values of the subject.

* * * * *